US008754209B2

(12) United States Patent
Sim et al.

(10) Patent No.: US 8,754,209 B2
(45) Date of Patent: Jun. 17, 2014

(54) INDAZOLE DERIVATIVES OR PHARMACEUTICALLY ACCEPTABLE SALTS THEREOF AS PROTEIN KINASE INHIBITORS FOR PROLIFERATIVE DISEASES TREATMENT, AND A PHARMACEUTICAL COMPOSITION CONTAINING THE SAME AS AN ACTIVE INGREDIENT

(75) Inventors: Tae Bo Sim, Daegu (KR); Jung Beom Son, Seoul (KR); Hwan Kim, Goyang-si (KR); Dong Sik Park, Busan (KR); Hwan Geun Choi, Seoul (KR); Young Jin Ham, Seoul (KR); Jung Mi Hah, Seoul (KR); Kyung Ho Yoo, Seoul (KR); Chang Hyun Oh, Seoul (KR); So Ha Lee, Seoul (KR); Jae Du Ha, Daejeon (KR); Sung Yun Cho, Daejeon (KR); Byoung Mog Kwon, Daejeon (KR); Dong Cho Han, Daejeon (KR)

(73) Assignees: Korea Institute of Science and Technology, Daejeon (KR); Korea Research Institute of Chemical Technology, Daejeon (KR); Korea Research Institute of Bioscience and Biotechnology, Daejeon (KR)

( * ) Notice: Subject to any disclaimer, the term of this patent is extended or adjusted under 35 U.S.C. 154(b) by 131 days.

(21) Appl. No.: 13/132,772

(22) PCT Filed: Dec. 4, 2009

(86) PCT No.: PCT/KR2009/007247
§ 371 (c)(1),
(2), (4) Date: Sep. 14, 2011

(87) PCT Pub. No.: WO2010/064875
PCT Pub. Date: Jun. 10, 2010

(65) Prior Publication Data
US 2012/0130069 A1 May 24, 2012

(30) Foreign Application Priority Data
Dec. 5, 2009 (KR) .................. 10-2008-0122999

(51) Int. Cl.
*C07D 413/14* (2006.01)
*C07D 413/12* (2006.01)
*C07D 417/12* (2006.01)
*C07D 401/12* (2006.01)
*C07D 405/12* (2006.01)
*C07D 403/12* (2006.01)
*C07D 409/12* (2006.01)
*C07D 231/56* (2006.01)

(52) U.S. Cl.
CPC ............ *C07D 413/14* (2013.01); *C07D 413/12* (2013.01); *C07D 401/12* (2013.01); *C07D 417/12* (2013.01); *C07D 405/12* (2013.01); *C07D 403/12* (2013.01); *C07D 409/12* (2013.01); *C07D 231/56* (2013.01)
USPC ........... 544/111; 544/130; 544/140; 544/371; 544/238; 546/199; 548/362.5; 548/248; 548/200

(58) Field of Classification Search
CPC .. C07D 231/56; C07D 409/12; C07D 403/12; C07D 405/12; C07D 413/12; C07D 417/12; C07D 401/12; C07D 413/14
USPC ............... 514/233.8; 544/140, 111, 130, 371, 544/238; 546/199; 548/362.5, 248, 200
See application file for complete search history.

(56) References Cited

U.S. PATENT DOCUMENTS 7,517,902 B2 4/2009 Halley et al.
2006/0004000 A1* 1/2006 D'Orchymont et al. ... 514/232.5

FOREIGN PATENT DOCUMENTS

| CN | 1980918 A | 6/2007 |
| WO | 03/051847 | 6/2003 |
| WO | 2006/003276 A1 | 1/2006 |

OTHER PUBLICATIONS

Cancer and Metastasis Reviews (1998), 17(1), 91-106.*
Science (1999), vol. 286, 531-537.*
G. Manning et al., "The Protein Kinase Complement of the Human Genome", Science, vol. 298, Dec. 2002, pp. 1912-1934.
Joseph Avurch et al., "Ras Activation of the Raf Kinase: Tyrosine Kinase Recruitment of the MAP Kinase Cascade", Recent Progress in Hormone Research, 2001, pp. 127-155.
M. Caraglia et al., "Targeting Raf-kinase: molecular rationales and translational issues", Annals of Oncology, vol. 17, 2006, pp. vii124-vii127.
Anton Yuryev et al., "Isoform-Specific Localization of A-Raf in Mitochondria", Molecular and Cellular Biology, vol. 20 No. 13, Jul. 2000, pp. 4870-4878.
Nancy H. Tran et al., "B-Raf and Raf-1 Are Regulated by Distinct Autoregulatory Mechanisms", Journal of Biological Chemistry, vol. 280 No. 16, Apr. 2005, pp. 16244-16253.
Claudia Wellbrock et al., "The Raf Proteins Take Centre Stage", Molecular Cell Biology, vol. 5, Nov. 2004, pp. 875-885.

(Continued)

Primary Examiner — Rebecca Anderson
(74) Attorney, Agent, or Firm — Staas & Halsey LLP

(57) ABSTRACT

Disclosed are novel indazole derivatives represented by the following Chemical Formula 1 or pharmaceutically acceptable salts, hydrates or solvates thereof, and pharmaceutical compositions for the prevention or treatment of proliferative diseases, containing the same as an active ingredient. Having potent inhibitory effect against protein kinase, such as b-raf, KDR, Fms, Tie2, SAPK2a and Ret, inducing diseases caused by abnormal cell proliferation, the novel indazole derivatives can be used for the prevention or treatment of diseases caused by abnormal cell proliferation.

8 Claims, 1 Drawing Sheet

(56) References Cited

OTHER PUBLICATIONS

Rama K. Jaiswal et al., "Nerve Growth Factor-mediated Activation of the Mitogen-activated Protein (MAP) Kinase Cascade Involves a Signaling Complex Containing B-Raf and HSP90", The Journal of Biological Chemistry, vol. 271 No. 39, 1996, pp. 23626-23629.

Helen Davies et al., "Mutations of the BRAF gene in human cancer", Nature, vol. 417, Jun. 2002, pp. 949-954.

David A. Tuveson et al, "BRAF as a potential therapeutic target in melanoma and other malignancies", Cancer Cell, vol. 4, Aug. 2003, pp. 95-98.

P.A. Norreys et al., "RAFI RAS oncogenes and mismatch-repair status", Nature, vol. 418, Aug. 2002, pp. 934.

Giuliana Salvatore et al. "Analysis of BRAF Point Mutation and RET/PTC Rearrangement Refines the Fine-Needle Aspiration Diagnosis of Papillary Thyroid Carcinoma", The Journal of Clinical Endocrinology & Metabolism, vol. 89, 2004, pp. 5175-5180.

Paul T.C. Wan et al., "Mechanism of Activation of the RAF-ERK Signaling Pathway by Oncogenic Mutations of B-Raf", Cell, vol. 116, Mar. 2004, pp. 855-867.

James Tsai et al., "Discovery of a selective inhibitor of oncogenic B-Raf kinase with potent antimelanoma activity", PNAS, vol. 105 No. 8, Feb. 2008, pp. 3041-3046.

Clara Montagut et al., "Elevated CRAF as a Potential Mechanism of Acquired Resistance to BRAF Inhibition in Melanoma", Cancer Research, Jun. 2008, pp. 4853-4861.

Michael S. Lyons et al., "Isolation of the Zebrafish Homologues for the *tie-1* and *tie-2* Endothelium-Specific Receptor Tyrosine Kinases", Developmental Dynamics, 1998, pp. 133-140.

Nina Jones et al., "Identification of Tek/Tie2 Binding Partners", The Journal of Biological Chemistry, vol. 274 No. 43, Oct. 1999, pp. 30896-30905.

Kevin G. Peters et al. "Functional Significance of Tie2 Signaling in the Adult Vasculature", The Endocrine Society, 2002, pp. 51-71.

Jason Witherington et al., "6-Heteroaryl-pyrazolo[3,4-*b*]pyridines: Potent and Selective Inhibitors of Glycogen Sythase Kinase-3 (GSK-3)", Bioorganic & Medicinal Chemistry Letters 13, 2003, pp. 3059-3062.

\* cited by examiner

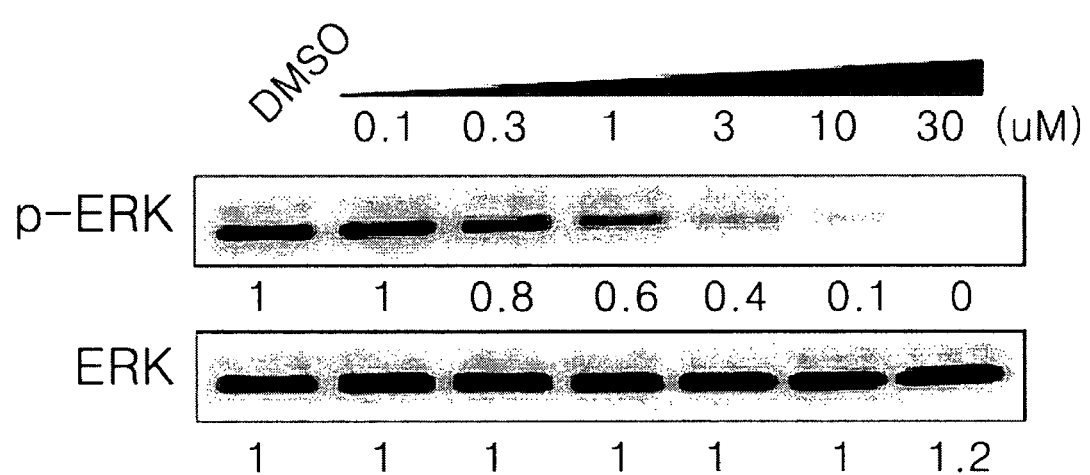

INDAZOLE DERIVATIVES OR PHARMACEUTICALLY ACCEPTABLE SALTS THEREOF AS PROTEIN KINASE INHIBITORS FOR PROLIFERATIVE DISEASES TREATMENT, AND A PHARMACEUTICAL COMPOSITION CONTAINING THE SAME AS AN ACTIVE INGREDIENT

CROSS REFERENCE TO RELATED APPLICATIONS

This application is a national phase application, under 35 U.S.C. 371, of international application No. PCT/KR2009/007247, filed on Dec. 4, 2009, which claimed priority to Korean Patent Application No. 10-2008-0122999, filed on Dec. 5, 2008.

TECHNICAL FIELD

The present invention relates to novel indazole derivatives, pharmaceutically acceptable salts thereof, preparation methods thereof and pharmaceutical compositions for the prevention and treatment of proliferative diseases containing the same as an active ingredient.

BACKGROUND ART

The protein kinase which catalyzes the phosphorylation of the hydroxyl group positioned in the tyrosine and serine/threonine residue of a protein manages the role of being important to the proliferation, differentiation, survival, migration, and invasion of a cell. The protein kinase is one of the most important commanders for controlling the signal transduction system within an organism. The signal transduction system in the living cell should be properly and smoothly turned on and put out for the maintenance of homeostasis of an organism. But the collapsed signal transduction system caused by the mutation or the overexpression of the specific protein kinases induces the various disease such as a cancer, an inflammation, a metabolic disease, a brain disorder and so forth. 518 kinds of human protein kinases have been identified or proposed so far, which is corresponding to about 1.7% of the human total gene exist. It bisects in the tyrosine protein kinase (over 90 kinds) and serine/threonine protein kinase. The tyrosine protein kinase can be classified into 20 subfamilies composed of 58 kinds which are receptor tyrosine kinases and 10 subfamilies composed of 32 kinds that belong to cytoplasm/non-receptor tyrosine kinases (Manning et al., Science, 2002, 298, 1912). The extracellular domain of the receptor tyrosine kinases can accommodate their ligands such as the growth factor and the kinase domain of them located in a cytoplasm can phosphorylate specific tyrosines. Once a ligand is binding to extracellular domain of a receptor tyrosine kinase, the receptor tyrosine kinase is dimerized and specific tyrosines in the cytoplasm domain become autophosphorylated. In turn, a signaling is progressed through the successive phosphorylation of downstream proteins in the cytoplasm and nucleus and this successive signaling eventually render transcription factors which cause cancer become activated and overexpressed. The Raf which belongs to serine/threonine (Ser/Thr) protein kinase family is responsible for transducing signal generated from activated growth factor receptor in cell membrane to the nucleus. The first identified rafgene is oncogenic v-raf (Mark G E et al., 1984). The signal transduction system derived from mitogen activated protein kinase (MAPK) is essential for cell proliferation, division, survival, death and invasion as well as transcription regulation and development. The MAPK signaling system works mainly by the sequential phosphorylation process of MAPK kinase kinase (MAPKKK), MAPK kinase (MAPKK), and MAPK. The Raf, MEK, and ERK (extracellular signal-regulated kinase) are corresponding to MAPK kinase kinase (MAPKKK, MAP3K), MAPK kinase (MAPKK, MAP2K) and MAPK respectively.

The Ras, a small GTP binding protein activated by signal from growth factor receptor render Raf-MEK-ERK sequentially phosphorylated and ultimately sequential MAPK signaling is transduced to the nucleus. Raf family kinase consists of A-raf, B-raf, and c-raf (raf-1). Raf-1 has most extensively been studied up on these three Raf isoforms. Ras tumor genes (especially k-Ras) which are constitutively active turned out to be implicated with pancreatic cancer (approximately 90%), rectal cancer (approximately 45%), liver cancer (approximately 30%), three non small cell lung cancer (approximately 35%), kidney cancer (approximately 10%) and other various solid tumors. The Raf-1 in conjunction with activated Ras could be activated once serine 338 of Raf-1 is phosphorylated (Avruch, J. et al., Recent Progress in Hormone Research, 2001, 56, 127). In contrast, the 14-3-3 protein combined with Raf-1 of which serin 259 is phosphorylated makes Raf-1 inactivated. Raf is also involved in NF-kB (nuclear factor kappa-light-chain-enhancer of activated B cells) signaling pathway and plays an important role in the immune response and inflammation (Caraglia, M. et al., Annals of Oncology, 2006, 17, 124). Raf phosphorylates inactive IKBs (Inhibitor of KB) protein and induces NFkB to be located in the nucleus and ultimately up-regulates transcription factors which inhibit cell death.

The dissimilar mechanism for the antiapoptotic of Raf is as follows. Raf binds to Bcl-2 to form Raf-Bcl-2 dimer and does the location shift to a mitochondria. If it makes Bad protein phosphorylated in that place, then the antiapoptotic function of Bcl-2 operates. The Raf is immunoprecipitated with Bcl-2-(Yuryev, A. et al., Mol. Cell. Biol. 2000, 20, 4870). Three subtypes (A-Raf, B-Raf, C-Raf/Raf-1) of the Raf protein bear the N-terminal control domain and preserved three domains (CR1, CR2, CR3) in the C-terminus kinase domain. CR1 includes the Ras binding domain in which a cystein is abundant. And CR2 has binding site for 14-3-3 protein i.e. a serine 259 of Raf-1. CR3 contains the catalytic domain (Tran et al., J Biol Chem, 2005, 280, 16244) and owns auto-phosphorylation site to be fully activated. For example, the phosphorylation of the threonine 491 and serine 494 of Raf-1 (Wellbrock, C. Nature Reviews Molecular Cell Biology, 2004, 5, 875) enables Raf-1 to be maximally activated.

Three subtypes of the Raf protein are overexpressed in different tissues. C-Raf is ubiquitously expressed in nearly all tissues, on the other hands, A-Raf is mainly expressed in urogenital apparatus (kidney, uterus and the prostate gland) and B-Raf is mainly found in a nerve, a spleen, and the blood forming organ (Jaiswal, R. K. et al, J. Biol. Chem., 1966, 271, 23626) (B-Raf (SEQ. ID NO. 1)).

B-Raf mutation is linked with about 7% of all of the human cancer. Especially, the mutation of B-Raf is observed in the frequency in which it is high in the melanoma (about 70%) that is a kind of the skin cancer. The B-raf-V600E mutant species in which the valine 600 positioned in Exon 15 is replaced by glutamic acid due to point mutation is mainly (about 90%) found in melanoma (Davies, H. et al, Nature 2002, 417, 949) (B-raf-V600E (SEQ. ID. NO. 2)). In vitro kinase activity of B-raf-V600E is about 500 times higher than that of wild type B-Raf. Accordingly, B-raf-V600E makes MAPK kinase signal transduction system be overactivated and induces various types of cancers. The reason why the kinase activity of B-raf-V600E is higher compared with wild type B-raf is as follows. The point-mutated glutamic acid 600 positioned in the B-Raf activation segment acts like phosphate group between phosphorylation sites (threonine 598 through serine 601). This phosphate mimicking induces conformation change which lead B-Raf kinase domain to be constitutively activated (Tuveson, D. A., Cancer Cell, 2003, 4, 95). The meantime till now identified B-raf mutant species are about 40. These mutations are significantly occurred in the activation segment and G-loop in which a glycine is abundant. The generation frequency of other mutant species except V600E is remarkably low. In the colorectal cancer, about 10% of the B-Raf mutant species are generated in the G-loop of the kinase domain (Rajagopalan et al., Nature 2002 418, 934).

The autologous suppression (auto-inhibition) domain exists in the N-terminal of B-Raf. However, B-Raf becomes always active once the activated H-Ras binds to B-Raf. This is formed through the phosphorylation of the serine-445, which corresponds to the phosphorylation of C-Raf serine-338. The B-Raf V600E mutant species interrupts the autologous suppression of B-Raf and renders B-Raf to beconstitutively active.

Moreover, the B-Raf-V600E mutant species is detected at the frequency in which it is high in the papillary thyroid cancer (about 50%) (Salvatore, G. J. Clin. Endocrinol. Metab. 2004, 89, 5175). The B-Raf-V600E mutant species is also implicated with the colon carcinoma (about 20%) and uterine cancer (about 30%). Meantime, the overactivivty of C-Raf is observed in the kidney cancer (renal cell carcinoma) and liver cancer (HCC) in about 50% and almost 100% frequency respectively without the expression of the mutant species.

Sorafenib (the BAY 43-9006/the trademark Nexavar) developed by Bayer and Onyx company strongly suppresses C-Raf, wild typeB-Raf, or the mutant species B-Raf. Moreover, sorafenib impedes the kinase activity of several receptor tyrosine kinases including the platelet-derived growth factor receptor, the vascular endothelial growth factor (vascular endothelial growth factor receptor 1/2/3), the fibroblast growth factor receptor, Flt-3, c-Kit, RET, and so forth. Sorafenib suppresses kinase activity through the mechanism in which it stabilizes DGF motif of the kinase domain to have the deactivated conformation (inactive conformation) (Wan, P. T. et. al. Cell, 2004, 116, 855). Sorafenib gained the approval from FDA as a therapeutic agent for advanced renal cell carcinoma in 2005. However, the clinical benefits of Sorafenib treatment is caused by the complex suppression of several kinases including the vascular endothelial growth factor (vascular endothelial growth factor receptor 1/2/3) than soley Raf impediment. In the phase II clinical investigation, The MTD (maximum tolerated dose) of Sorafenib was 400 mg twice a day. The administration of 600 mg Sorafenib twice a dayinduces the skin toxicity side effect of the grade 3. The skin of hand and foot gets stripped off and the common side effect of Sorafenib is the erythema, and hand-foot syndrome of the edema symptom. Meantime, sorafenib received the approval as the hepatocellular carcinoma (HCC) therapeutic agent in 2008. Moreover, in the phase II clinical trial, Sorafenib demonstrated reasonable efficacy against the thyroid cancer, metastatic prostate cancer, and breast cancer. In the meanwhile, Sorafenib revealed a mild therapeutic efficacy against the melanoma that is a kind of skin cancer. Meantime, PLX4-720, 7-azaindole derivative developed by Plexxikon induces the apoptosis of the melanoma cell line such as 1205Lu (raf-V660E overexpression cell strain) (Tsai, J. et. al. PNAS, 2008, 105, 3041). PLX-4720 strongly impedes the kinase activity of Raf-V660E with an $IC_{50}$ value of 13 nM and exhibits good anti-proliferative activity ($IC_{50}$=0.5 μM) against the A375 melanoma cell line (raf-V660E overexpression cell strain). CHIR-265 developed by the Norvatis/Chiron strongly inhibits several kinases like B-Raf-V600E ($IC_{50}$=19 nM), KDR ($IC_{50}$=70 nM), PDGFR-b ($IC_{50}$=30 nM), and c-Kit ($IC_{50}$=20 nM). CHIR-265 is under phase I clinical investigation for melanoma treatment. Recently, the resistance problem of the Raf inhibitors comes to the front. Montagut and collegues did culture of M14 cell strain (human body melanoma cell line) that bears the B-Raf-V600E mutant species in the presence of Raf inhibitor (AZ628) and obtained the clones which resist against Raf inhibitor (AZ628). They explained the mechanism for resistance occurence of Raf inhibitor on the basis of this experiment. If B-Raf is inhibited, the protein expression level of C-Raf increases and the drug inhibitory activity against B-Raf-V600E falls down. But the susceptibility of the geldanamycin, HSP90 inhibitor increases on the melanoma cell line which resists against the Raf inhibitor (AZ628). Therefore, HSP90 inhibition can override the resistance problem of the Raf inhibitor (Montagut, C. Cancer Research, 2008, 68, 4853).

VEGFR-2 (Vascular endothelial growth factorreceptor-2) also referred to as KDR/Flk-1 (kinase insert domain-containing receptor/fetal liver kinase) belongs to the class III family of receptor tyrosine kinases and is deeply implicated with angiogenesis process that ultimately leads to new blood vessels formation from pre-existing vessels. Angiogenesis is associated with pathological conditions such as cancer, rheumatoid arthritis, diabetic retinopathy, and neovascular glaucoma. It has widely been known that VEGFR-2 inhibition suppress angiogenesis and VEGFR-2 has been regarded as an attractive molecular target for cancer therapeutics.

VEGF is mainly generated in the blood vessel endothelial cell, the hemopoietic cell, and the stromal cell in the hypoxic state and by the stimulation of TGF, interleukin, and cell growth factors like PDGF. VEGF binds to the VEGF receptor (VEGFR)-1, -2, and -3. The signal specificity of VEGFR is more delicately controlled by a neurophilin, the heparan sulfate, the coreceptor (assisted receptor) including cadherin and integrin.

The biological function of VEGF is mediated through the type III RTK, the VEGFR-1 (Flt-1), the VEGFR-2 (KDR/Flk-1), and VEGFR-3 (Flt-4). VEGFR becomes closely related to the Fms, Kit, and PDGFR. Whereas VEGF-A unite combines with VEGFR-1 and -2, VEGF-C binds to VEGF-2 and -3. Whereas VEGF-A and -B preferentially need for the angiogenesis, VEGF-C and -D are essential to the lymphangiogenesis. The new blood vessels make pass role for supplying nutrient and oxygen to a tumor and play a role for the cancer cell metastasis, which are essential to proliferation and invasion of cancer cell. In case of normal cell, the angiogenesis is made to be balanced within an organism by the mutual regulation of the angiogenesis accelerated substance (angiogenic stimulator) and suppression of angiogenesis material (angiogenic suppressor) but in case of cancer cell, this balance is broken and VEGFR is activated by VEGF (vascular endothelial growth factor) which most reaches the big effect to the vascular endothelial cell. The small molecule inhibitors which suppress the receptor tyrosine kinases such as VEGFR have been variously studied and developed as there is high possibility that these anti-angiogenicagents can be used for treating most of the solid tumors. In addition, they have the advantage of expecting therapeutic efficacy with relatively lower side effect compared with cyto-toxic anti-cancer agents.

A lot of small molecule VEGFR-2 inhibitors have been identified and pursued and some of these are currently under clinical investigation (Schenone et al., *Curr. Med. Chem.* 2007; 14:2495.). Sorafenib and Sunitinb that are multi-targeted tyrosine kinase inhibitors including VEGFR-2 inhibition have already been launched.

Another receptor tyrosine kinase related to angiogenesis is Tie-2 expressed predominantly on vascular endothelium. Tie-2 has also been found in haematopoietic cells. Angiopoietins, Ang1 and Ang 2 were discovered as Tie-2 ligand (Davis et al., *Cell* 1996; 87:1161.). Ang 1 binding to extracellular domain of Tie-2 leads to auto-phosphorylation of Tie-2 kinase domain but curiously does not activate MAPK nor does it stimulate mitogenesis. It seems likely that Ang 2 plays crucial functions in the lymphatic vascular system. It has already been proved Tie-2 inhibition with dominant-negative Tie-2 receptor reduces tumor angiogenesis and growth in mice (Lin et al., *Proc. Natl. Acad. Sci. USA* 1998; 95:8829.).

The RET (rearranged during transfection) protooncogen primarily expressed in the nervous and excretory systems belongs to receptor tyrosine kinase family. N-terminal extracellular domain of RET is composed of four cadherin-like repeats, a calcium-binding site, nine N-glycosylation sites, and a cysteine-rich region (Airaksinen et al., *Nat. Rev. Neurosci.* 2002; 3:383.). At least 12 tyrosine autophosphorylation sites are located in the cytoplasmic domain of RET isoforms (Liu, *J. Biol. Chem.* 1996; 271:5309.). For instance, there are 16 tyrosines in the intracellular kinase domain of RET9 isoform. GFUGFR-α complex binding to extracellular portion of RET renders kinase domain of RET autophosphorylated and activated (Aiaksinen et al., *Nat. Rev. Neurosci.* 2002; 3:383.). GNDF ((glial-derived neurotropic factor) family ligands, GFL is composed of GDNF, artemin, neurturin, and persephin. GNDF family receptor-, GFR-α composed of four subtypes (GFR-α 1-4) represents glycosylphosphatidylinositol-anchored coreceptors. It has been reported that RET plays important roles in the development of parasympathetic and enteric nervous systems and kidney in mice (Pachnis et al., Development1993; 119:1005.). RET lose of function caused by germline mutation is implicated with Hirschsprung's disease (Manie et al., *Trends Genet.* 2001; 17:580.) that is defined as congenital aganglionosis of the distal intestines. In contrast, gain of function RET mutation is found to be associated with human cancers such as multiple endocrine neoplasia type 2A (MEN2A), MEN2B, and familial medullary thyroid carcinoma (FMTC). In particular, RET turns out to be a promising molecular target of thyroid cancer therapeutics (Cote and Gagel, *N. Engl. J. Med.* 2003; 349:1566.). Bcr-Abl that is a oncogenic fused tyrosine kinase is generated by abberant translocation of Bcr (breakpoint cluster region) gene located on chromosome 22 and Abl (V-abl Abelson murine leukemia viral oncogene homolog) gene from chromosome 9. This characteristic chromosomal translocation is referred to as Philadelphia chromosome (Nowell and Hungerford, *J. Natl. Cancer Inst.* 1960; 25:85.). The size of Bcr-Abl fused protein is determined by the breakpoint of Bcr compartment. Out of three isoform (190, 210, 230 kDa) of Bcr-Abl implicated with leukemia, p210Bcr-Abl has proved to be sufficient for causing CML (chronic myeloid leukemia). Gleevec (Imatinib mesylate) of which chemotype is phenylaminopyrimidine (PAP) has opened new era in drug discovery field as Gleevec is the first drug for molecularly targeted therapeutics. Unfortunately, Gleevec recently suffers from acquired drug resistance mainly due to several kinds of point mutations that have emerged in the kinase domain of Abl. Next generation of Gleevec is significantly required to override Gleevec resistance by inhibiting all of clinically relevant point mutants including T3151-Bcr-Abl even though the second generation of Gleevec such as Nilotinib and Dasatinib has already launched on the market. Nilotinib and Dasatinib are unfortunately inactive on including T3151-Bcr-Abl that turned out to be clinically the most serious point mutant.

DISCLOSURE

Technical Problem

Accordingly, it is an object of the present invention to provide indazole derivatives or pharmaceutically acceptable salts thereof which inhibit protein kinases such as RAF, KDR, FMS, Ret, Tie-2, and SAPK and possess anti-proliferative activities for cancer therapeutics.

It is another object of the present invention to provide methods for the preparation of novel indazole derivatives or pharmaceutically acceptable salts thereof.

It is further object of the present invention to provide a pharmaceutical composition for the prevention or treatment of proliferative diseases containing indazole derivatives or pharmaceutically acceptable salts thereof as an active ingredient.

Technical Solution

In order to accomplish the above objects, the present invention provides novel indazole derivatives, pharmaceutically acceptable salts thereof, methods for the preparation of novel indazole derivatives. In another aspect of the present invention, the present invention provides a pharmaceutical composition containing novel indazole derivatives or pharmaceutically acceptable salts thereof as an active ingredient.

Advantageous Effects

The indazole derivatives of the present invention are found to have potent inhibitory activity against protein kinase, such as b-raf, KDR, Fms, Tie2, SAPK2a and Ret, inducing diseases caused by abnormal cell proliferation, the novel indazole derivatives can be used for the prevention or treatment of diseases caused by abnormal cell proliferation.

DESCRIPTION OF DRAWINGS

FIG. 1 provides a image of the western blotting of the novel indazole compound according to the present invention.

BEST MODE

The present invention provides novel indazole derivatives, represented by the following chemical Formula 1, and pharmaceutically acceptable salts thereof:

[Chemical Formula 1]

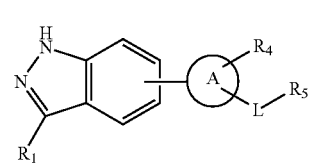

wherein,

R₁ is HOCH₂— or

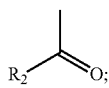

R₂ is hydrogen, hydroxy, C₁-C₃ alkoxy or R³—(CH₂)ₙ—NH—;
R₃ is hydrogen, dimethylamine, morpholin, phenyl, heteroaryl, phenyl which is substituted with CF₃, or C₃-C₆ cycloalkyl;
A is 5-6 membered aryl or heteroaryl which is substituted with R₄ and LR₅;
R₄ is hydrogen or C₁-C₃ alkyl;
L is —NH— or —C(O)NH—;
R₅ is hydrogen, —C(O)—R₆, —C(O)NH—R₆ or —S(O)₂—R₆;
R₆ is one selected from a group consisting of phenyl, benzyl, 5 or 6 membered heteroaryl, naphthalenyl and benzothienyl, wherein each one substituted one or two substituents selected from a group consisting of hydrogen, —CH₃, —CF₃, —OCH₃, —Br, —Cl, —NO₂,

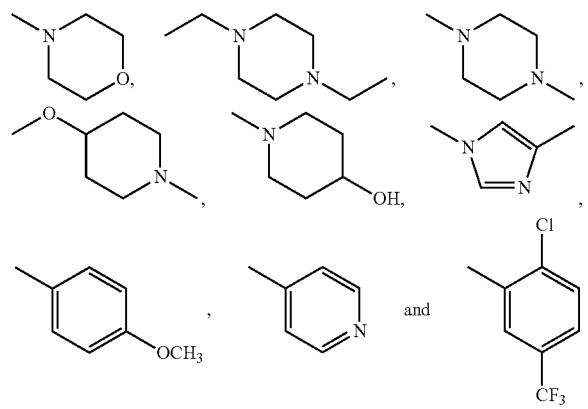

n is 0, 1 or 2.

Preferably, 5 or 6 membered of R₆ heteroaryl is thienyl, furanyl, oxazolyl, isoxazolyl, thiazolyl, pyrazolyl, isothiazolyl, pyridyl, pyridazinyl or pyrazinyl.

More preferably, R₆ is phenyl, (trifluoromethyl)phenyl, 4-nitro-3-(trifluoromethyl)phenyl, 3-(4-methyl-1H-imidazole-1-yl)-5-(trifluoromethyl)phenyl, 4-(1-methylpiperidine-4-yloxy)-3-(trifluoromethyl)phenyl, 3,4-dichlorophenyl, 4-chloro-3-(trifluoromethyl)phenyl, 3,5-bis(trifluoromethyl)phenyl, 3,4-dimethoxyphenyl, 3-morpholino-5-(trifluoromethyl)phenyl, 2,3-dichloro phenyl, 2,4-dimethylphenyl, 4-((4-ethylpiperazin-1-yl)methyl)-3-(trifluoro methyl)phenyl, 4-(4-methylpiperazin-1-yl)-3-(trifluoromethyl)phenyl, 3-(4-hydroxypiperadin-1-yl)-5-(trifluoromethyl)phenyl, 4-(1-methylpiperadin-4-yloxy)-3-(trifluoromethyl)phenyl, benzyl, 3,4-dimethoxybenzyl, thienyl, 5-bromothienyl, pyrazinyl, furanyl, 2,5-dimethylfuranyl, 5-(4-methoxypenyl)furanyl, 5-(2-chloro-5-(trifluoromethyl)phenyl)furanyl, isoxazolyl, 5-methyl isoxazolyl, pyrazolyl, 1-(4-methoxyphenyl)-5-(trifluoromethyl)-1H-pyrazolyl, pyridazinyl, pyridinyl, 3-chloropyridinyl, thiazolyl, 4-(2-(pyridin-4-yl)thiazolyl, naphthalenyl, 4,7-dimethoxy naphthalenyl, benzo[b]thiophenyl, pyrimidinyl, imidazolyl, pyrrolyl, dihydropyrrolyl, oxazolyl, triazolyl, thiadiazolyl, benzimidazolyl, quinolinyl, tetrahydroquinolinyl, benzothiazolyl, benzothiazophenyl, benzodioxolyl, indazolyl, indolyl, indylyl, dihydroindylyl or dihyrobenzofuranyl.

Particular examples of indazole derivatives according to the present invention as follows:
1) ethyl 6-(4-aminophenyl)-1H-indazole-3-carboxylate;
2) ethyl 6-(4-(3-(trifluoromethyl)benzamido)phenyl)-1H-indazole-3-carboxylate;
3) ethyl 6-(4-(5-bromothiophene-2-carboxamido)phenyl)-1H-indazole-3-carboxylate;
4) ethyl 6-(4-(pyrazine-2-carboxamido)phenyl)-1H-indazole-3-carboxylate;
5) ethyl 6-(4-(benzo[b]thiophene-2-carboxamido)phenyl)-1H-indazole-3-carboxylate;
6) ethyl 6-(4-(2,5-dimethylfuran-3-carboxamido)phenyl)-1H-indazole-3-carboxylate;
7) ethyl 6-(4-(5-methylisoxazole-3-carboxamido)phenyl)-1H-indazole-3-carboxylate;
8) ethyl 6-(4-(1-(4-methoxyphenyl)-5-(trifluoromethyl)-1H-pyrazole-4-carboxamido)phenyl)-1H-indazole-3-carboxylate;
9) ethyl 6-(4-(4-nitro-3-(trifluoromethyl)benzamido)phenyl)-1H-indazole-3-carboxylate;
10) ethyl 6-(4-(pyridazine-4-carboxamido)phenyl)-1H-indazole-3-carboxylate;
11) ethyl 6-(4-(2-(3,4-dimethoxyphenyl)acetamido)phenyl)-1H-indazole-3-carboxylate;
12) ethyl 6-(4-(5-(4-methoxyphenyl)furan-2-carboxamido)phenyl)-1H-indazole-3-carboxylate;
13) ethyl 6-(4-(3-chloroisonicotinamido)phenyl)-1H-indazole-3-carboxylate;
14) ethyl 6-(4-(thiazole-4-carboxamido)phenyl)-1H-indazole-3-carboxylate;
15) ethyl 6-(4-(4,7-dimethoxy-1-naphthamido)phenyl)-1H-indazole-3-carboxylate;
16) ethyl 6-(4-(5-(2-chloro-5-(trifluoromethyl)phenyl)furan-2-carboxamido)phenyl)-1H-indazole-3-carboxylate;
17) ethyl 6-(4-(2-(pyridin-4-yl)thiazole-4-carboxamido)phenyl)-1H-indazole-3-carboxylate;
18) ethyl 6-(4-(3-(4-methyl-1H-imidazol-1-yl)-5-(trifluoromethyl)benzamido)phenyl)-1H-indazole-3-carboxylate;
19) ethyl 6-(4-(4-(1-methylpiperidin-4-yloxy)-3-(trifluoromethyl)benzamido)phenyl)-1H-indazole-3-carboxylate;
20) ethyl 6-(4-(3-(3,4-dichlorophenyl)ureido)phenyl)-1H-indazole-3-carboxylate;
21) ethyl 6-(4-(3-(4-chloro-3-(trifluoromethyl)phenyl)ureido)phenyl)-1H-indazole-3-carboxylate;
22) ethyl 6-(4-(3-(3,5-bis(trifluoromethyl)phenyl)ureido)phenyl)-1H-indazole-3-carboxylate;
23) ethyl 6-(4-(3-(3-(trifluoromethyl)phenyl)ureido)phenyl)-1H-indazole-3-carboxylate;
24) N-methyl-6-(4-(3-(trifluoromethyl)benzamido)phenyl)-1H-indazole-3-carboxamide;
25) 6-(4-(5-(4-methoxyphenyl)furan-2-carboxamido)phenyl)-N-methyl-1H-indazole-3-carboxamide;
26) 6-(4-(5-bromothiophene-2-carboxamido)phenyl)-N-methyl-1H-indazole-3-carboxamide;
27) 6-(4-(benzo[b]thiophene-2-carboxamido)phenyl)-N-methyl-1H-indazole-3-carboxamide;
28) 6-(4-(3-(3,5-bis(trifluoromethyl)phenyl)ureido)phenyl)-N-methyl-1H-indazole-3-carboxamide;
29) N-methyl-6-(4-(3-(3-(trifluoromethyl)phenyl)ureido)phenyl)-1H-indazole-3-carboxamide;
30) N-(2-morpholinoethyl)-6-(4-(3-(trifluoromethyl)benzamido)phenyl)-1H-indazole-3-carboxamide;

31) 6-(4-(5-bromothiophene-2-carboxamido)phenyl)-N-(2-morpholinoethyl)-1H-indazole-3-carboxamide;
32) 6-(4-(benzo[b]thiophene-2-carboxamido)phenyl)-N-(2-morpholinoethyl)-1H-indazole-3-carboxamide;
33) 6-(4-(2,5-dimethylfuran-3-carboxamido)phenyl)-N-(2-morpholinoethyl)-1H-indazole-3-carboxamide;
34) 6-(4-(1-(4-methoxyphenyl)-5-(trifluoromethyl)-1H-pyrazole-4-carboxamido)phenyl)-N-(2-morpholinoethyl)-1H-indazole-3-carboxamide;
35) 6-(4-(5-bromothiophene-2-carboxamido)phenyl)-N-(3-(trifluoromethyl)phenyl)-1H-indazole-3-carboxamide;
36) 6-(4-(3-(3,4-dichlorophenyl)ureido)phenyl)-N-(2-morpholinoethyl)-1H-indazole-3-carboxamide;
37) N-methyl-6-(4-(pyridazine-4-carboxamido)phenyl)-1H-indazole-3-carboxamide;
38) 5-methyl-N-(4-(3-(methylcarbamoyl)-1H-indazol-6-yl)phenyl)isoxazole-3-carboxamide;
39) N-methyl-6-(4-(3-(4-methyl-1H-imidazol-1-yl)-5-(trifluoromethyl)benzamido)phenyl)-1H-indazole-3-carboxamide;
40) N-methyl-6-(4-(4-(1-methylpiperidin-4-yloxy)-3-(trifluoromethyl)benzamido)phenyl)-1H-indazole-3-carboxamide;
41) N-(4-(3-(methylcarbamoyl)-1H-indazol-6-yl)phenyl)thiazole-4-carboxamide;
42) methyl 5-(4-aminophenyl)-1H-indazole-3-carboxylate;
43) methyl 5-(4-(3-(4-chloro-3-(trifluoromethyl)phenyl)ureido)phenyl)-1H-indazole-3-carboxylate;
44) ethyl 6-(3-aminophenyl)-1H-indazole-3-carboxylate;
45) ethyl 6-(3-(3-(trifluoromethyl)benzamido)phenyl)-1H-indazole-3-carboxylate;
46) ethyl 6-(3-(5-methylisoxazole-3-carboxamido)phenyl)-1H-indazole-3-carboxylate;
47) ethyl 6-(3-(benzo[b]thiophene-2-carboxamido)phenyl)-1H-indazole-3-carboxylate;
48) ethyl 6-(3-(2-(3,4-dimethoxyphenyl)acetamido)phenyl)-1H-indazole-3-carboxylate;
49) ethyl 6-(3-(5-bromothiophene-2-carboxamido)phenyl)-1H-indazole-3-carboxylate;
50) N-(2-morpholinoethyl)-6-(3-(3-(trifluoromethyl)benzamido)phenyl)-1H-indazole-3-carboxamide;
51) methyl 6-(3-aminophenyl)-1H-indazole-3-carboxylate;
52) methyl 6-(3-(3-morpholino-5-(trifluoromethyl)benzamido)phenyl)-1H-indazole-3-carboxylate;
53) ethyl 6-(5-amino-2-methylphenyl)-1H-indazole-3-carboxylate;
54) ethyl 6-(3-(3-(2,3-dichlorophenyl)ureido)phenyl)-1H-indazole-3-carboxylate;
55) ethyl 6-(3-(3-(3,4-dichlorophenyl)ureido)phenyl)-1H-indazole-3-carboxylate;
56) methyl 6-(3-(3-(2,4-dimethyl phenyl)ureido)phenyl)-1H-indazole-3-carboxylate;
57) ethyl 6-(5-(3-(4-chloro-3-(trifluoromethyl)phenyl)ureido)-2-methylphenyl)-1H-indazole-3-carboxylate;
58) 6-(3-(3-(4-chloro-3-(trifluoromethyl)phenyl)ureido)phenyl)-N-(2-morpholinoethyl)-1H-indazole-3-carboxamide;
59) 6-(3-(3-morpholino-5-(trifluoromethyl)benzamido)phenyl)-N-(2-morpholinoethyl)-1H-indazole-3-carboxamide;
60) 6-(3-(3-(2,3-dichlorophenyl)ureido)phenyl)-N-(2-morpholinoethyl)-1H-indazole-3-carboxamide;
61) 6-(3-(3-(2,3-dichlorophenyl)ureido)phenyl)-N-ethyl-1H-indazole-3-carboxamide;
62) 6-(3-(3-(3,4-dichlorophenyl)ureido)phenyl)-N-ethyl-1H-indazole-3-carboxamide;
63) 6-(3-(3-(2,4-dimethyl phenyl)ureido)phenyl)-N-ethyl-1H-indazole-3-carboxamide;
64) 6-(5-(3-(4-chloro-3-(trifluoromethyl)phenyl)ureido)-2-methylphenyl)-N-(2-morpholinoethyl)-1H-indazole-3-carboxamide;
65) 6-(5-(3-(4-chloro-3-(trifluoromethyl)phenyl)ureido)-2-methylphenyl)-N-(2-(dimethylamino)ethyl)-1H-indazole-3-carboxamide;
66) 6-(5-(3-(4-chloro-3-(trifluoromethyl)phenyl)ureido)-2-methylphenyl)-N-cyclopropyl-1H-indazole-3-carboxamide;
67) 6-(2-methyl-5-(3-(trifluoromethyl)benzamido)phenyl)-N-(2-morpholinoethyl)-1H-indazole-3-carboxamide;
68) ethyl 6-(3-(3-(trifluoromethyl)phenylsulfonamido)phenyl)-1H-indazole-3-carboxylate;
69) ethyl 6-(3-(3-(4-((4-ethylpiperazin-1-yl)methyl)-3-(trifluoromethyl)phenyl)ureido)phenyl)-1H-indazole-3-carboxylate;
70) methyl 6-(3-(3-(4-(4-methylpiperazin-1-yl)-3-(trifluoromethyl)phenyl)ureido)phenyl)-1H-indazole-3-carboxylate;
71) ethyl 6-(2-methyl-5-(3-(4-(4-methylpiperazin-1-yl)-3-(trifluoromethyl)phenyl)ureido)phenyl)-1H-indazole-3-carboxylate;
72) 5-(4-(3-(4-chloro-3-(trifluoromethyl)phenyl)ureido)phenyl)-N-(2-morpholinoethyl)-1H-indazole-3-carboxamide;
73) N-methyl-6-(2-methyl-5-(3-(4-methyl-1H-imidazol-1-yl)-5-(trifluoromethyl)benzamido)phenyl)-1H-indazole-3-carboxamide;
74) ethyl 6-(2-methyl-5-(3-(3-(4-methyl-1H-imidazol-1-yl)-5-(trifluoromethyl)phenyl)ureido)phenyl)-1H-indazole-3-carboxylate;
75) N-methyl-6-(2-methyl-5-(3-(3-(4-methyl-1H-imidazol-1-yl)-5-(trifluoromethyl)phenyl)ureido)phenyl)-1H-indazole-3-carboxamide;
76) ethyl 6-(3-(3-(4-hydroxypiperidin-1-yl)-5-(trifluoromethyl)benzamido)phenyl)-1H-indazole-3-carboxylate;
77) 6-(3-(3-(4-hydroxypiperidin-1-yl)-5-(trifluoromethyl)benzamido)phenyl)-N-(2-morpholinoethyl)-1H-indazole-3-carboxamide;
78) methyl 6-(3-(4-(1-methylpiperidin-4-yloxy)-3-(trifluoromethyl)benzamido)phenyl)-1H-indazole-3-carboxylate;
79) 1-(4-chloro-3-(trifluoromethyl)phenyl)-3-(3-(3-(hydroxymethyl)-1H-indazol-6-yl)phenyl)urea;
80) ethyl-6-(5-(3-(trifluoromethyl)phenylcarbamoyl)thiophen-3-yl)-1H-indazole-3-carboxylate; or
81) 6-(4-(2,5-dimethylfuran-3-carboxamido)phenyl)-N-(2-morpholinoethyl)-1H-indazole-3-carboxamide hydrochloride.

The indazole derivatives of the present invention, represented by the Chemical Formula 1, may be used in the form of pharmaceutically acceptable salts. Useful are acid addition salts having pharmaceutically acceptable free acids. The free acids may be inorganic or organic. Examples of useful inorganic free acids include hydrochloric acid, nitric acid, phosphoric acid, sulfuric acid, perchloric acid, bromic acid. As organic acids, acetic acid, methane sulfonic acid, ethane sulfonic acid, p-toluenesulfonic acid, fumaric acid, maleic acid, malonic acid, phthalic acid, succinic acid, lactic acid, citric acid, gluconic acid, tartaric acid, salicylic acid, malic acid, oxalic acid, benzoic acid, embonate, aspartic acid or glutamic acid may be used.

Also, indazole derivatives of the present invention, represented by Chemical Formula 1, may be in the form of conventionally producible salts, hydrates, and solvates thereof as well as pharmaceutically acceptable salts.

Addition salts according to the present invention may be prepared using a conventional method. For example, they may be prepared by dissolving the compound of Chemical Formula 1 in a water-miscible organic solvent, such as acetone, methanol, ethanol or 1,4-dioxane and adding an excess of organic acids or an excess of free base so as to precipitate or crystallize salts. A preparation method of the free base is described in example 81.

Further, the present invention provides the methods for the preparation of novel indazole derivatives or pharmaceutically acceptable salts thereof. Preferably, indazole derivatives or pharmaceutically acceptable salts thereof described by said Chemical Formula 1 can be prepared by the methods described in below reaction Formulas, but the methods are not restricted by the reaction Formulas. Especially, men in the art could understand that indazole derivatives or pharmaceutically acceptable salts thereof described by said Chemical Formula 1 can be prepared by plural ways using well known technology in the art.

In accordance with an embodiment of the present invention, the method for the preparation of intermediate of Chemical Formula 5, as illustrated by the following Reaction Scheme 1, comprises preparing the compound of Chemical Formula 3 by 3 step-reaction from the compound of Chemical Formula 2 (Step 1);

preparing the compound of Chemical Formula 4 by esterification from the compound of Chemical Formula 3 of Step 1 (Step 2); and preparing the compound of Chemical Formula 5 by protection of functional group of compound of the Chemical Formula 4 of Step 2 (Step 3):

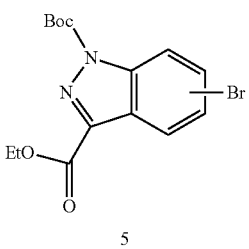

wherein, Boc is tertiary-butoxycarbonyl.

In accordance with another embodiment of the present invention, the method for the preparation of novel indazole derivatives of Chemical Formula 1a, as illustrated by the following Reaction Scheme 2, comprises preparing the compound of Chemical Formula 7 by Suzuki cross-coupling reaction from the compound of Chemical Formula 5 and 6 (Step 1);

preparing the compound of Chemical Formula 8 by deprotection and reduction of the compound of Chemical Formula 7 of Step 1 (Step 2);

preparing the compound of Chemical Formula 9 by substitution of the compound of Chemical Formula 8 of Step 2 (Step 3);

preparing the compound of Chemical Formula 10 by hydrolysis of the compound of Chemical Formula 9 of Step 3 (Step 4); and preparing the compound of Chemical Formula 1a by coupling reaction (amidation) the compound of Chemical Formula 10 of Step 4 with amine ($R_3$—$(CH_2)_n$—NH) (Step 5):

[Reaction Scheme 1]

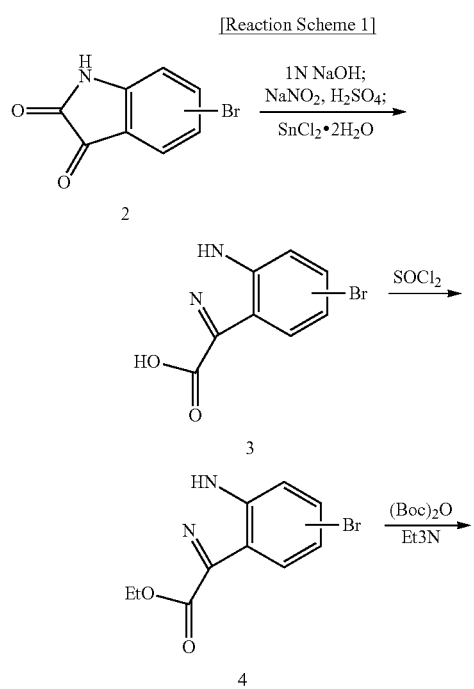

[Reaction Scheme 2]

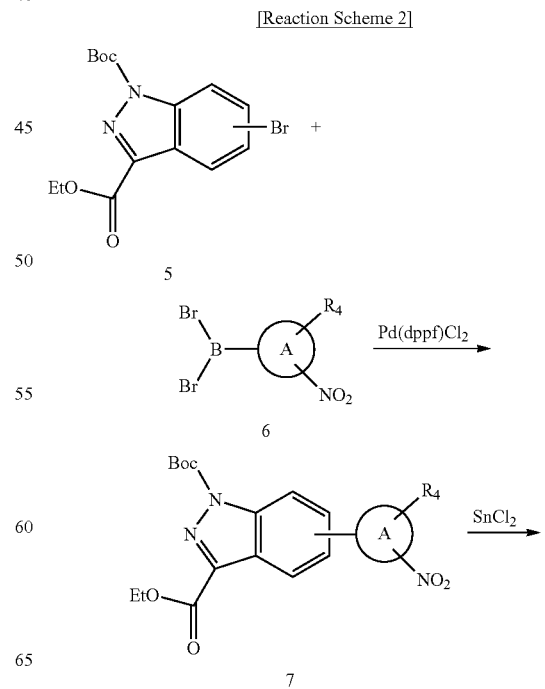

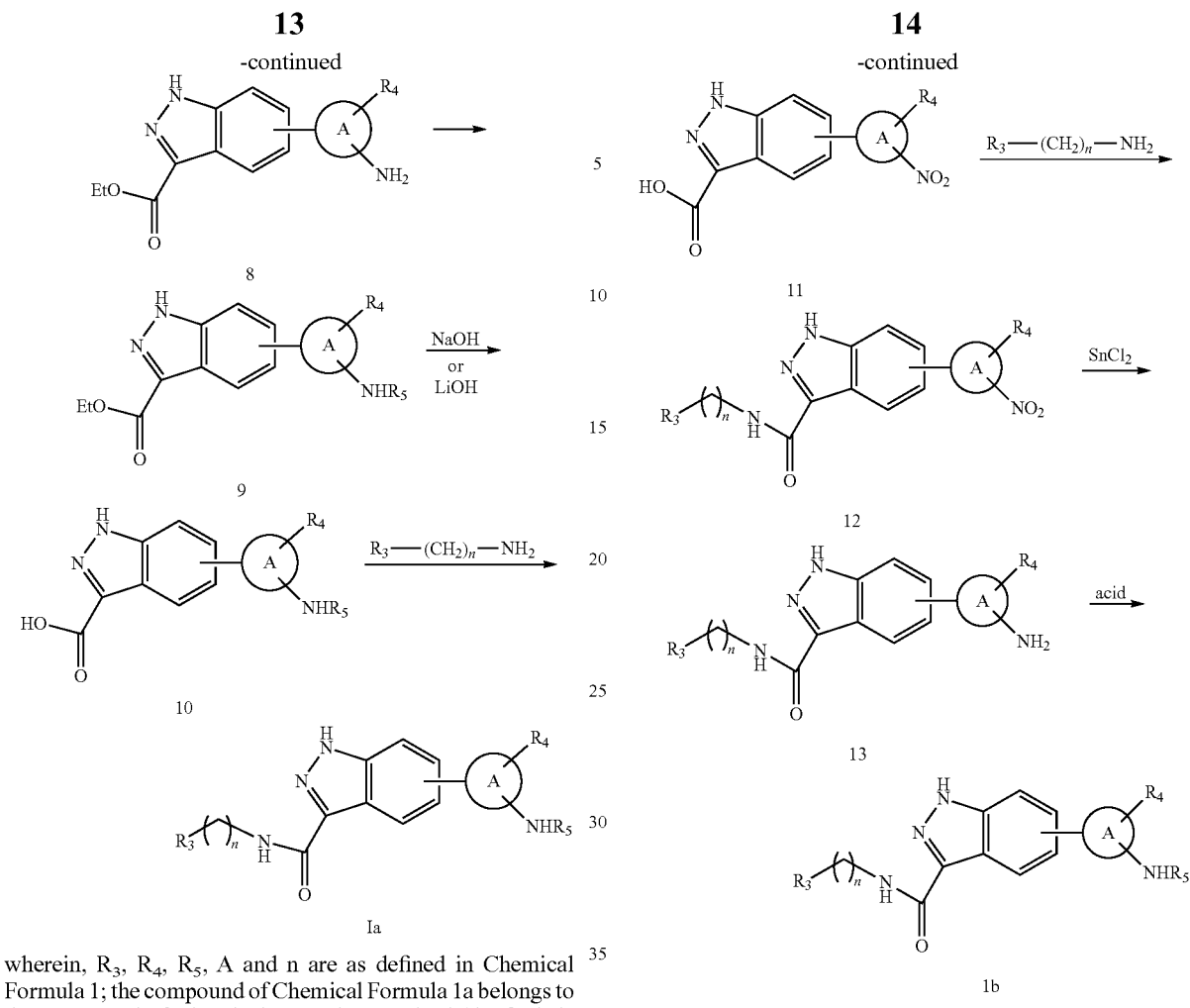

wherein, $R_3$, $R_4$, $R_5$, A and n are as defined in Chemical Formula 1; the compound of Chemical Formula 1a belongs to the compound of Chemical Formula 1; and Pd (dppf)Cl$_2$ is 1,1'-bis (dephenylphosphin)ferrocenedichloro palladium.

In accordance with further embodiment of the present invention, the method for the preparation of novel indazole derivatives of Chemical Formula 1b, as illustrated by the following Reaction Scheme 3, comprises preparing the compound of Chemical Formula 11 by deprotection and hydrolysis of the compound of Chemical Formula 7 (Step 1);

preparing the compound of Chemical Formula 12 by coupling reaction (amidation) the compound of Chemical Formula 11 of Step 1 with amine ($R_3$—($CH_2$)$_n$—NH) (Step 2);

preparing the compound of Chemical Formula 13 by reduction of the compound of Chemical Formula 12 of Step 2 (Step 3); and preparing the compound of Chemical Formula Ib by coupling reaction the compound of Chemical Formula 13 of Step 3 with carboxylic acid (Step 4):

[Reaction Scheme 3]

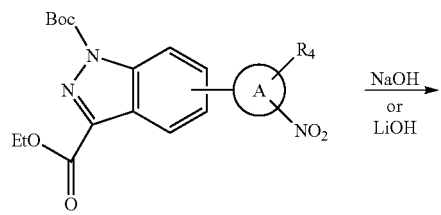

wherein, $R_3$, $R_4$, $R_5$, A and n are as defined in Chemical Formula 1 and the compound of Chemical Formula 1b belongs to the compound of Chemical Formula 1.

Further, the present invention provides a pharmaceutical composition for prevention or treatment of diseases caused by abnormal cell proliferation, containing a indazole derivatives represented by Chemical Formula 1 or a pharmaceutically acceptable salt thereof as an active ingredient. Having potent inhibitory effect against protein kinase, such as b-raf, KDR, Fms, Tie2, SAPK2a and Ret, inducing diseases caused by abnormal cell proliferation, the novel indazole derivatives can be used for the prevention or treatment of diseases caused by abnormal cell proliferation.

The diseases caused by abnormal cell proliferation is selected from a group consisting of stomach cancer, lung cancer, liver cancer, colorectal cancer, pancreatic cancer, brain cancer, bone cancer, melanoma cancer, breast cancer, nodular sclerosing adenosis, uterine cancer, cervical cancer, head and neck cancer, esophageal cancer, thyroid cancer, parathyroid cancer, renal cell cancer, osteosarcoma, prostatic carcinoma, urethra cancer, bladder cancer, blood cancer, lymphoma, psoriasis and fibroadenoma.

The blood cancer is selected from a group consisting of leukemia, multiple myeloma and myelodysplastic syndrome.

The lymphoma is Hodgkin's disease or non-Hodgkin's lymphoma.

MODE FOR INVENTION

A better understanding of the present invention may be obtained through the following examples which are set forth to illustrate, but are not to be construed as the limit of the present invention.

Example 1

Preparation of ethyl 6-(4-aminophenyl)-1H-indazole-3-carboxylate

Step 1: Preparation of 6-bromo-1H-indazole-3-carboxylic acid

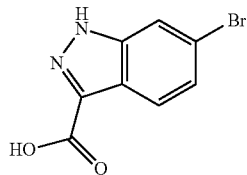

The solution of 6-bromoisatin (10 g, 22 mmol) in 1N aqueous NaOH solution (48 Ml) was stirred at 50° C. for 1 h. The mixture was cooled to 0° C. Sodium nitrite (3 g, 22 mmol) solution in water (11 Ml) was added dropwise for 15 min at 0° C. The mixture was added to the solution of water (90 Ml) and sulfuric acid (4.6 Ml) at 0° C. for 15 min. The mixture was added to the solution of conc. hydrochloric acid (40 Ml) and SnCl$_2$.2H$_2$O (24 g, 53 mmol). After 1 h, the mixture was filtered and washed with water. The solid was dried through air flow to give the titled compound (8.98 g).

$^1$H NMR (300 MHz, DMSO-d$_6$) δ 13.76 (bs, 1H), 7.87 (s, 1H), 7.55 (d, J=8 Hz, 1H), 7.27 (d, J=8 Hz, 1H), 2.44 (s, 3H).

Step 2: Preparation of ethyl 6-bromo-1H-indazole-3-carboxylate

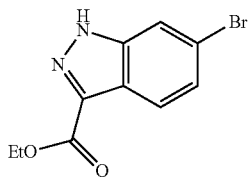 [SMILES: CCOC(=O)c1n[nH]c2cc(Br)ccc12]

To a stirred solution of 6-bromo-1H-indazole-3-carboxylic acid (5 g, 21 mmol) in ethanol (160 Ml), thionyl chloride (8 Ml, 104 mmol; SOCl$_2$) was added. The mixture was refluxed for 3 h, cooled to room temperature, and concentrated under reduced pressure. Ethyl acetate was added. The organic layer was washed with saturated sodium bicarbonate solution, dried over magnesium sulfate, and concentrated under reduced pressure. The residue was purified by flash column chromatography (silica gel, DCM:MeOH=9:1) to give ethyl 6-bromo-1H-indazole-3-carboxylate (2.8 g).

$^1$H NMR (300 MHz, CDCl$_3$) δ14.04 (br s, 1H), 8.00 (d, J=8.4 Hz, 1H), 7.91 (d, J=1.2 Hz, 1H), 7.45 (dd, J=1.5, 8.7 Hz, 1H), 4.39 (q, J=7.2 Hz, 2H), 1.35 (t, J=7.2 Hz, 3H).

Step 3: Preparation of 1-tert-butyl 3-ethyl 6-bromo-1H-indazole-1,3-dicarboxylate

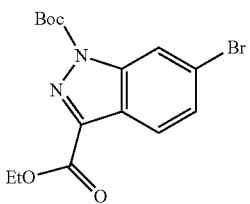 [SMILES: CCOC(=O)c1nn(C(=O)OC(C)(C)C)c2cc(Br)ccc12]

To a stirred solution of ethyl 6-bromo-1H-indazole-3-carboxylate (1.68 g, 6.6 mmol) in dichloromethane (44 Ml), was added N,N-dimethylaminopyridine (20 mg, 0.66 mmol), triethylamine (0.26 Ml, 7.3 mmol), and (Boc)$_2$O (0.76 Ml, 1.65 mmol) successively at 0° C. After 1 h, the mixture was warmed to room temperature for 3 h and dichloromethane was added. The organic layer was washed with water, dried over magnesium sulfate, and concentrated under reduced pressure. The residue was purified by flash column chromatography (silica gel, Hex/EA=4:1) to give 1-tert-butyl 3-ethyl 6-bromo-1H-indazole-1,3-dicarboxylate (2.2 g).

$^1$H NMR (400 MHz, DMSO-d$_6$) δ8.29 (d, J=1.6 Hz, 1H), 8.06 (d, J=8.8 Hz, 1H), 7.67 (dd, J=1.6, 8.8 Hz, 1H), 4.47 (q, J=7.2 Hz, 2H), 1.41 (t, J=7.2 Hz, 3H).

Step 4: Preparation of 1-tert-butyl 3-ethyl 6-(4-nitrophenyl)-1H-indazole-1,3-dicarboxylate

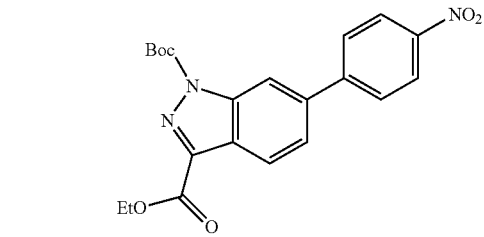 [SMILES: CCOC(=O)c1nn(C(=O)OC(C)(C)C)c2cc(-c3ccc([N+](=O)[O-])cc3)ccc12]

The mixture of 1-tert-butyl 3-ethyl 6-bromo-1H-indazole-1,3-dicarboxylate (1.3 g), p-nitrophenyl boronic acid (666 mg), Pd (dppf)Cl$_2$ (92 mg), and potassium carbonate (1 g) in N,N-dimethylformamide/water (4:1, 20 Ml) was stirred at room temperature for 24 h. Ethyl acetate and water were added. The organic layer was separated, washed with water, dried over magnesium sulfate, and concentrated under reduced pressure. The residue was purified by flash column chromatography (silica gel, EA only) to give 1-tert-butyl 3-ethyl 6-(4-nitrophenyl)-1H-indazole-1,3-dicarboxylate (1.3 g).

$^1$H NMR (400 MHz, DMSO-d$_6$) δ8.48 (s, 1H), 8.38 (d, J=8.8 Hz, 2H), 8.29 (d, J=8.4 Hz, 1H), 8.06 (d, J=8.8 Hz, 2H), 7.93 (dd, J=1.6, 8.4 Hz, 1H), 4.48 (q, J=7.2 Hz, 2H), 1.42 (t, J=7.2 Hz, 3H).

Step 5: Preparation of ethyl 6-(4-aminophenyl)-1H-indazole-3-carboxylate

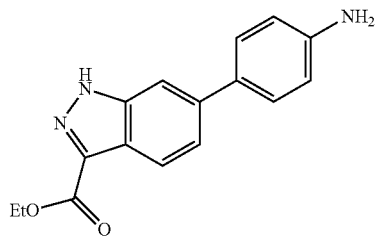 [SMILES: CCOC(=O)c1n[nH]c2cc(-c3ccc(N)cc3)ccc12]

To a stirred solution of 1-tert-butyl 3-ethyl 6-(4-nitrophenyl)-1H-indazole-1,3-dicarboxylate (879 mg, 2.14 mmol) in ethanol (40 Ml), was added SnCl$_2$ (2.4 g, 10.7 mmol) and the mixture was stirred at 80° C. for 3 h. The mixture was cooled to room temperature and saturated sodium bicarbonate aqueous solution was added. The organic layer was extracted three times and the combined organic layer was dried over sodium sulfate and concentrated under reduced pressure. The residue was triturated in ethyl acetate and hexane to give ethyl 6-(4-aminophenyl)-1H-indazole-3-carboxylate (442 mg).

$^1$H NMR (400 MHz, DMSO-d$_6$) δ13.80 (s, 1H), 8.03 (d, J=8.4 Hz, 1H), 7.66 (s, 1H), 7.53 (dd, J=1.2, 8.4 Hz, 1H), 7.44 (d, J=8.4 Hz, 2H), 6.67 (d, J=8.4 Hz, 1H), 5.30 (s, 2H), 4.39 (q, J=7.2 Hz, 2H), 1.38 (t, J=7.2 Hz, 3H).

Example 2

Preparation of ethyl 6-(4-(3-(trifluoromethyl)benzamido)phenyl)-1H-indazole-3-carboxylate

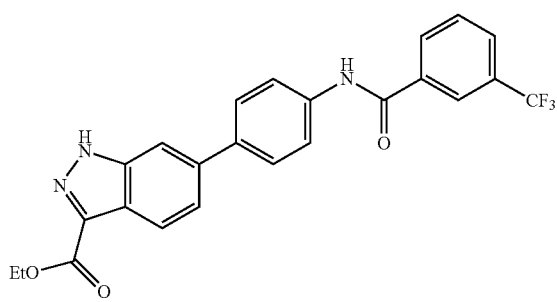

To a stirred solution of ethyl 6-(4-aminophenyl)-1H-indazole-3-carboxylate (40 mg), 3-trifluoromethyl-benzoic acid (35.2 mg), triethylamine (40 and HOBt (25 mg) in N,N-dimethylformamide, was added EDCI (40.6 mg). The mixture was stirred at 70° C. for 12 h. The mixture cooled to room temperature and ethyl acetate and water were added. The mixture was extracted with ethyl acetate three times. The combined organic layer was washed with saturated sodium bicarbonate solution, dried over sodium sulfate, and concentrated under reduced pressure. The residue was triturated by ethylacetate/hexane to give ethyl 6-(4-(3-(trifluoromethyl) benzamido)phenyl)-1H-indazole-3-carboxylate (46.6 mg).

$^1$H NMR (400 MHz, DMSO-d$_6$) δ 13.98 (s, 1H), 10.62 (s, 1H), 8.34 (s, 1H), 8.30 (d, J=8 Hz, 1H), 8.13 (d, J=8.8 Hz, 1H), 7.99 (d, J=8 Hz, 1H), 7.93 (d, J=8.8 Hz, 2H), 7.86 (s, 1H), 7.81 (t, J=7.2 Hz, 1H), 7.80 (d, 8.8 Hz, 2H), 7.65 (br d, J=8.8 Hz, 1H), 4.41 (q, J=6.8 Hz, 2H), 1.40 (t, J=6.8 Hz, 3H).

Example 3

Preparation of ethyl 6-(4-(5-bromothiophene-2-carboxamido)phenyl)-1H-indazole-3-carboxylate

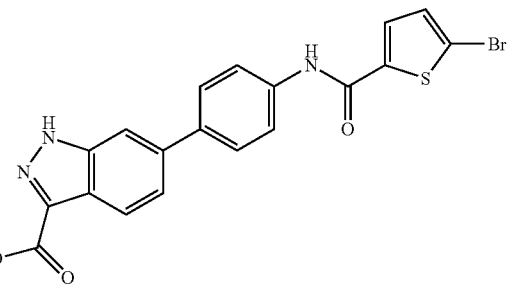

The titled compound was prepared by repeating the procedure described in example 2.

$^1$H NMR (400 MHz, DMSO-d$_6$) δ13.98 (brs, 1H), 10.42 (s, 1H), 8.12 (d, J=8.4 Hz, 1H), 7.90 (d, J=4 Hz, 1H), 7.85 (d, J=8.4 Hz, 2H), 7.84 (s, 1H), 7.78 (d, J=8.4 Hz, 2H), 7.65 (d, J=8.4 Hz, 1H), 7.39 (d, J=4 Hz, 1H), 4.41 (q, J=7.2 Hz, 2H), 1.40 (t, J=7.2 Hz, 3H).

Example 4

Preparation of ethyl 6-(4-(pyrazine-2-carboxamido) phenyl)-1H-indazole-3-carboxylate

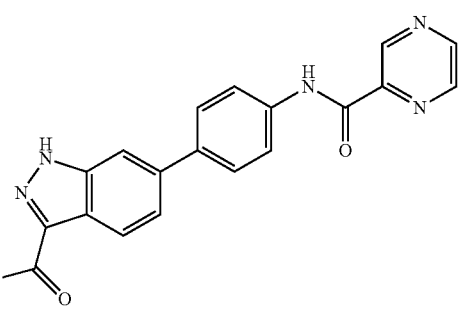

The titled compound was prepared by repeating the procedure described in example 2.

$^1$H NMR (400 MHz, DMSO-d$_6$) δ13.99 (brs, 1H), 10.91 (s, 1H), 9.33 (s, 1H), 8.95 (s, 1H), 8.84 (s, 1H), 8.12 (d, J=8.4 Hz, 1H), 8.06 (d, J=8.4 Hz, 2H), 7.86 (s, 1H), 7.80 (d, J=8.4 Hz, 2H), 7.66 (d, J=8.4 Hz, 1H), 4.41 (q, J=7.2 Hz, 2H), 1.40 (t, J=7.2 Hz, 3H).

Example 5

Preparation of ethyl 6-(4-(benzo[b]thiophene-2-carboxamido)phenyl)-1H-indazole-3-carboxylate

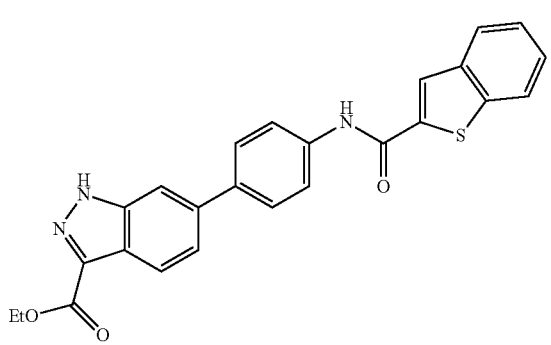 [SMILES: CCOC(=O)c1n[nH]c2cc(-c3ccc(NC(=O)c4cc5ccccc5s4)cc3)ccc12]

The titled compound was prepared by repeating the procedure described in example 2.

¹H NMR (400 MHz, DMSO-d₆) δ 13.99 (s, 1H), 10.73 (s, 1H), 8.41 (s, 1H), 8.13 (d, J=8.8 Hz, 1H), 8.07 (d, J=8.8 Hz, 1H), 8.03 (d, J=6.8 Hz, 1H), 7.93 (d, J=8.8 Hz, 2H), 7.86 (s, 1H), 7.81 (d, J=8.8 Hz, 2H), 7.66 (d, J=8.4 Hz, 1H), 7.53-7.48 (m, 2H), 4.42 (q, J=8.8 Hz, 2H), 1.40 (t, J=8.8 Hz, 3H).

Example 6

Preparation of ethyl 6-(4-(2,5-dimethylfuran-3-carboxamido)phenyl)-1H-indazole-3-carboxylate

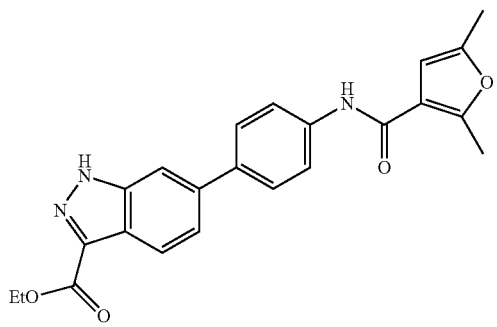 [SMILES: CCOC(=O)c1n[nH]c2cc(-c3ccc(NC(=O)c4cc(C)oc4C)cc3)ccc12]

The titled compound was prepared by repeating the procedure described in example 2.

¹H NMR (400 MHz, DMSO-d₆) δ14.01 (brs, 1H), 9.72 (s, 1H), 8.11 (d, J=8.8 Hz, 1H), 7.86 (d, J=8.8 Hz, 2H), 7.83 (s, 1H), 7.74 (d, J=8.8 Hz, 2H), 7.64 (dd, J=1.2, 8.8 Hz, 1H) 6.69 (s, 1H), 4.41 (q, J=6.8 Hz, 2H), 2.52 (s, 3H), 2.28 (s, 3H), 1.39 (t, J=6.8 Hz, 3H).

Example 7

Preparation of ethyl 6-(4-(5-methylisoxazole-3-carboxamido)phenyl)-1H-indazole-3-carboxylate

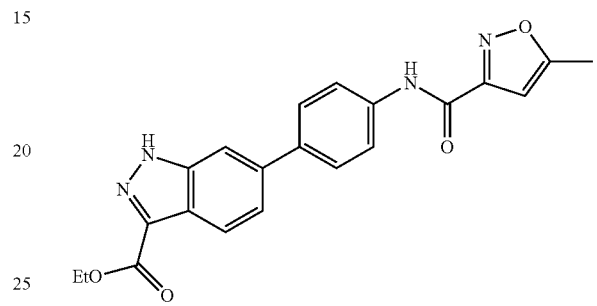

The titled compound was prepared by repeating the procedure described in example 2.

¹H NMR (400 MHz, DMSO-d₆) δ13.96 (brs, 1H), 10.79 (s, 1H), 8.12 (d, J=11.2 Hz, 1H), 7.93 (d, J=11.6 Hz, 2H), 7.85 (s, 1H), 7.77 (d, J=11.6 Hz, 2H), 7.65 (d, J=11.2 Hz, 1H), 6.69 (s, 1H), 4.41 (q, J=9.6 Hz, 2H), 1.39 (t, J=9.6 Hz, 3H).

Example 8

Preparation of ethyl 6-(4-(1-(4-methoxyphenyl)-5-(trifluoromethyl)-1H-pyrazole-4-carboxamido)phenyl)-1H-indazole-3-carboxylate

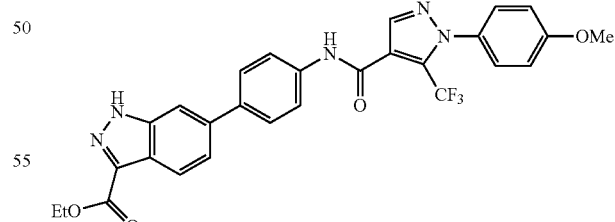

The titled compound was prepared by repeating the procedure described in example 2.

¹H NMR (400 MHz, DMSO-d₆) δ13.88 (br s, 1H), 10.65 (s, 1H), 8.29 (s, 1H), 8.12 (d, J=10.8 Hz, 1H), 8.03 (d, J=11.2 Hz, 2H), 7.84 (s, 1H), 7.78 (d, J=11.2 Hz, 2H), 7.65 (d, J=9.6

Hz, 1H), 7.47 (d, J=11.6 Hz, 2H), 7.13 (d, J=12 Hz, 2H), 4.41 (q, J=9.6 Hz, 2H), 3.86 (s, 3H), 1.40 (t, J=9.6 Hz, 3H).

2H), 7.87 (s, 1H), 7.82 (d, J=11.6 Hz, 2H), 7.66 (dd, J=2, 11.6 Hz, 1H), 4.41 (q, J=9.2 Hz, 2H), 1.40 (t, J=9.2 Hz, 3H).

Example 9

Preparation of ethyl 6-(4-(4-nitro-3-(trifluoromethyl)benzamido)phenyl)-1H-indazole-3-carboxylate

Example 11

Preparation of ethyl 6-(4-(2-(3,4-dimethoxyphenyl)acetamido)phenyl)-1H-indazole-3-carboxylate

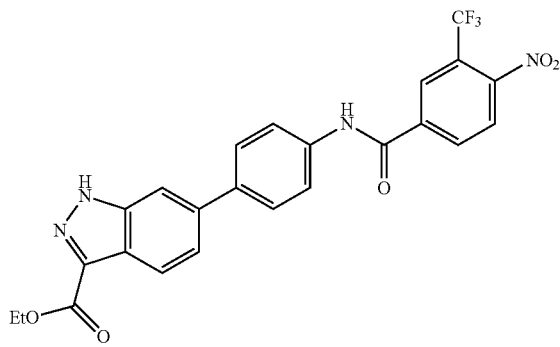 [SMILES: CCOC(=O)c1n[nH]c2cc(-c3ccc(NC(=O)c4ccc([N+](=O)[O-])c(C(F)(F)F)c4)cc3)ccc12]

The titled compound was prepared by repeating the procedure described in example 2.

$^1$H NMR (300 MHz, DMSO-d$_6$) δ13.99 (s, 1H), 10.81 (s, 1H), 8.53 (s, 1H), 8.51 (d, J=8.4 Hz, 1H), 8.35 (d, J=8.4 Hz, 1H), 7.93 (d, J=8.1 Hz, 2H), 7.88 (s, 1H), 7.86 (d, J=8.1 Hz, 2H), 7.67 (d, J=8.4 Hz, 1H), 4.41 (q, J=6.9 Hz, 2H), 1.39 (t, J=6.9).

The titled compound was prepared by repeating the procedure described in example 2.

$^1$H NMR (400 MHz, DMSO-d$_6$) δ13.95 (br s, 1H), 10.24 (br s, 1H), 8.10 (d, J=11.6 Hz, 1H), 7.80 (s, 1H), 7.72 (br s, 4H), 7.61 (dd, J=1.6, 11.6 Hz, 1H), 6.96 (d, J=2.4 Hz, 1H), 6.91 (d, J=11.2 Hz, 1H), 6.86 (dd, J=2.4, 10.8 Hz, 1H), 4.41 (q, J=9.6 Hz, 2H), 3.75 (s, 3H), 3.72 (s, 3H), 3.60 (s, 2H), 1.39 (t, J=9.6 Hz, 3H).

Example 10

Preparation of ethyl 6-(4-(pyridazine-4-carboxamido)phenyl)-1H-indazole-3-carboxylate

Example 12

Preparation of ethyl 6-(4-(5-(4-methoxyphenyl)furan-2-carboxamido)phenyl)-1H-indazole-3-carboxylate

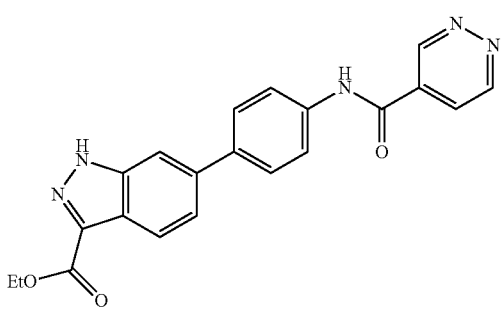 [SMILES: CCOC(=O)c1n[nH]c2cc(-c3ccc(NC(=O)c4ccnnc4)cc3)ccc12]

The titled compound was prepared by repeating the procedure described in example 2.

$^1$H NMR (400 MHz, DMSO-d$_6$) δ13.94 (br s, 1H), 10.92 (br s, 1H), 9.68 (s, 1H), 9.51 (dd, J=1.6, 7.2 Hz, 1H), 8.16 (d, J=7.2 Hz, 1H), 8.13 (d, J=11.6 Hz, 1H), 7.92 (d, J=11.6 Hz,

The titled compound was prepared by repeating the procedure described in example 2.

$^1$H NMR (400 MHz, DMSO-d$_6$) δ13.99 (br s, 1H), 10.26 (s, 1H), 8.12 (d, J=11.6 Hz, 1H), 7.92 (d, J=12 Hz, 4H), 7.86 (s, 1H), 7.80 (d, J=12 Hz, 2H), 7.67 (d, J=11.6 Hz, 1H), 7.42

(d, J=4.8 Hz, 1H), 7.07 (d, J=12.8 Hz, 2H), 7.03 (d, J=5.2 Hz, 1H), 4.41 (q, J=9.2 Hz, 2H), 3.83 (s, 3H), 1.40 (t, J=9.2 Hz, 3H).

Example 13

Preparation of ethyl 6-(4-(3-chloroisonicotinamido)phenyl)-1H-indazole-3-carboxylate

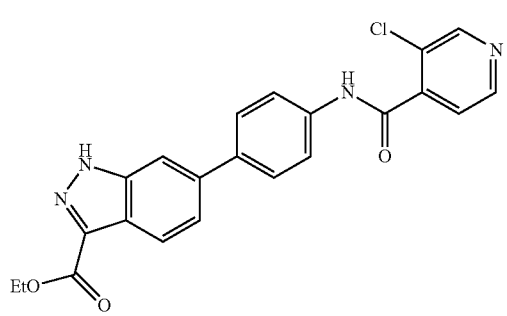 [SMILES: CCOC(=O)c1n[nH]c2cc(-c3ccc(NC(=O)c4ccncc4Cl)cc3)ccc12]

The titled compound was prepared by repeating the procedure described in example 2.

$^1$H NMR (400 MHz, DMSO-d$_6$) δ13.99 (s, 1H), 10.85 (s, 1H), 8.81 (s, 1H), 8.69 (d, J=6.4 Hz, 1H), 8.13 (d, J=11.6 hz, 1H), 7.82 (m, 5H), 7.70 (d, J=6.4 Hz, 1H), 7.65 (d, J=10 Hz, 1H), 4.41 (q, J=9.6 Hz, 2H), 1.40 (t, J=9.6 Hz, 3H).

Example 14

Preparation of ethyl 6-(4-(thiazole-4-carboxamido)phenyl)-1H-indazole-3-carboxylate

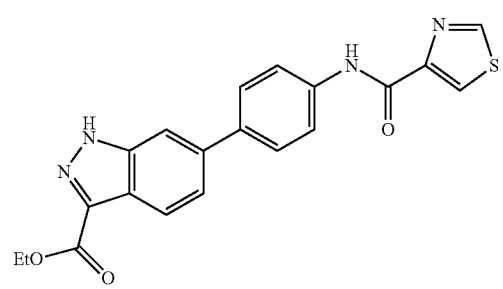 [SMILES: CCOC(=O)c1n[nH]c2cc(-c3ccc(NC(=O)c4cscn4)cc3)ccc12]

The titled compound was prepared by repeating the procedure described in example 2.

$^1$H NMR (400 MHz, DMSO-d$_6$) δ 13.97 (br s, 1H), 10.51 (s, 1H), 9.29 (d, J=2.4 Hz, 1H), 8.54 (d, J=2.8 Hz, 1H), 8.12 (d, J=11.2 Hz, 1H), 8.01 (d, J=11.6 hz, 2H), 7.85 (s, 1H), 7.77 (d, J=11.6 Hz, 2H), 7.65 (dd, J=1.6, 11.2 Hz, 1H), 4.41 (q, J=9.6 Hz, 2H), 1.39 (t, J=9.2 Hz, 3H).

Example 15

Preparation of ethyl 6-(4-(4,7-dimethoxy-1-naphthamido)phenyl)-1H-indazole-3-carboxylate

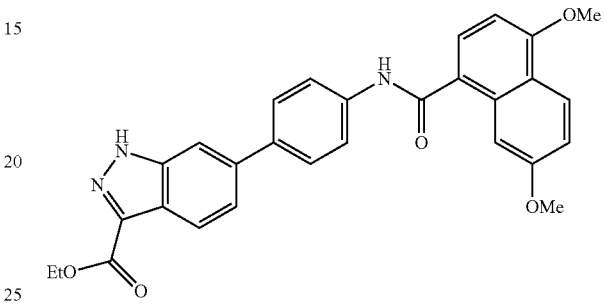

The titled compound was prepared by repeating the procedure described in example 2.

$^1$H NMR (400 MHz, DMSO-d$_6$) δ1.40 (t, 3H), 3.82 (s, 3H), 4.03 (s, 3H), 4.42 (q, 2H), 6.94 (dd, 1H), 7.23 (dd, 1H), 7.66 (dd, 1H), 7.79 (m, 4H), 7.85 (s, 1H), 7.94 (dd, 2H), 8.14 (m, 2H), 10.53 (s, 1H).

Example 16

Preparation of ethyl 6-(4-(5-(2-chloro-5-(trifluoromethyl)phenyl)furan-2-carboxamido)phenyl)-1H-indazole-3-carboxylate

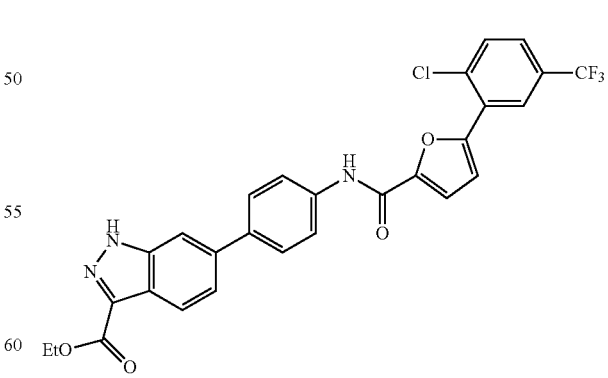

The titled compound was prepared by repeating the procedure described in example 2.

¹H NMR (400 MHz, DMSO-d₆) δ 1.40 (t, 3H), 4.42 (q, 2H), 7.51 (m, 2H), 7.65 (dd, 1H), 7.80 (dd, 3H), 7.86 (dd, 2H), 7.91 (dd, 2H), 8.12 (dd, 1H), 8.49 (s, 1H), 10.52 (s, 1H).

Example 17

Preparation of ethyl 6-(4-(2-(pyridin-4-yl)thiazole-4-carboxamido)phenyl)-1H-indazole-3-carboxylate

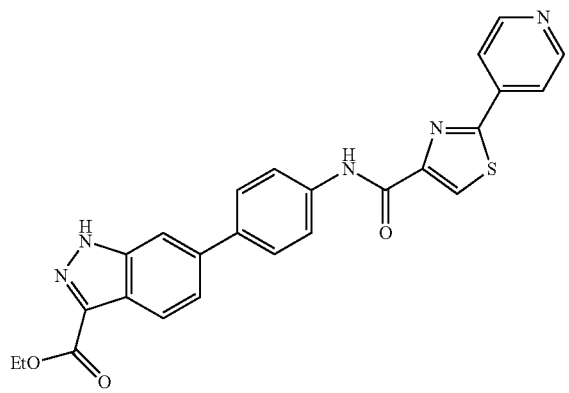 [SMILES: CCOC(=O)c1n[nH]c2cc(-c3ccc(NC(=O)c4csc(-c5ccncc5)n4)cc3)ccc12]

The titled compound was prepared by repeating the procedure described in example 2.

¹H NMR (400 MHz, DMSO-d₆) δ 1.40 (t, 3H), 4.42 (q, 2H), 7.66 (dd, 1H), 7.83 (d, 2H), 7.92 (s, 1H), 8.03 (dd, 2H), 8.13 (m, 3H), 8.67 (s, 1H), 8.79 (dd, 2H), 10.45 (s, 1H).

Example 18

Preparation of ethyl 6-(4-(3-(4-methyl-1H-imidazol-1-yl)-5-(trifluoromethyl)benzamido)phenyl)-1H-indazole-3-carboxylate

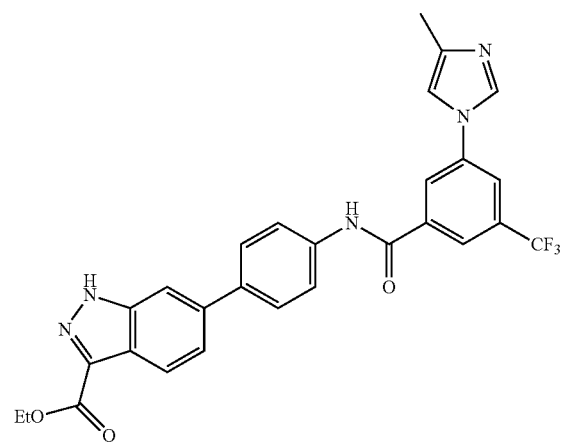 [SMILES: CCOC(=O)c1n[nH]c2cc(-c3ccc(NC(=O)c4cc(-n5cnc(C)c5)cc(C(F)(F)F)c4)cc3)ccc12]

The titled compound was prepared by repeating the procedure described in example 2.

¹H NMR (400 MHz, DMSO-d₆) δ13.96 (br s, 1H), 10.65 (s, 1H), 8.48 (s, 1H), 8.42 (s, 1H), 8.26 (s, 1H), 8.20 (s, 1H), 8.14 (d, J=8.8 Hz, 1H), 7.93 (d, J=8.4 Hz, 2H), 7.87 (s, 1H), 7.83 (d, J=8.4 Hz, 2H), 7.73 (s, 1H), 7.67 (d, J=8.8 Hz, 1H), 4.42 (q, J=7.2 Hz, 2H), 2.20 (s, 3H), 1.40 (t, J=7.2 Hz, 3H).

Example 19

Preparation of ethyl 6-(4-(4-(1-methylpiperidin-4-yloxy)-3-(trifluoromethyl)benzamido)phenyl)-1H-indazole-3-carboxylate

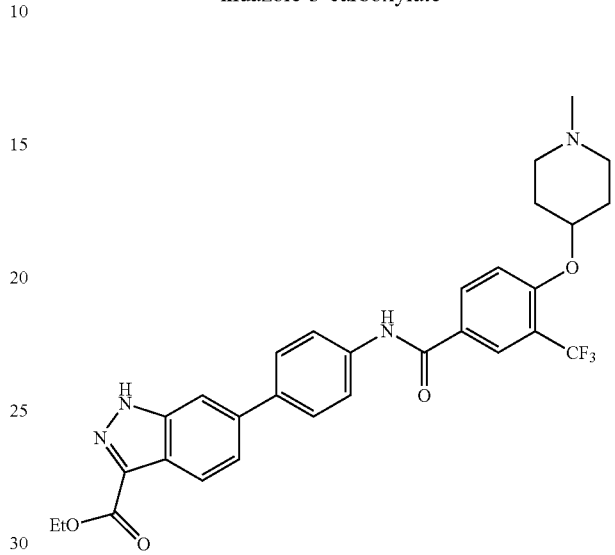

The titled compound was prepared by repeating the procedure described in example 2.

¹H NMR (400 MHz, DMSO-d₆) δ14.01 (s, 1H), 10.43 (s, 1H), 8.27 (s, 1H), 8.25 (d, J=8.4 Hz, 1H), 8.13 (d, J=8.8 Hz, 1H), 7.91 (d, J=8.4 Hz, 2H), 7.85 (s, 1H), 7.80 (s, 1H), 7.78 (d, J=8.4 Hz, 2H), 7.57 (d, J=9.2 Hz, 1H), 7.48 (d, J=9.2 Hz, 1H), 4.79 (m, 1H), 4.41 (q, J=7.2 Hz, 2H), 2.31 (m, 4H), 2.18 (s, 3H), 1.97 (m, 2H), 1.75 (m, 2H), 1.40 (t, J=6.8 Hz, 3H).

Example 20

Preparation of ethyl 6-(4-(3-(3,4-dichlorophenyl)ureido)phenyl)-1H-indazole-3-carboxylate

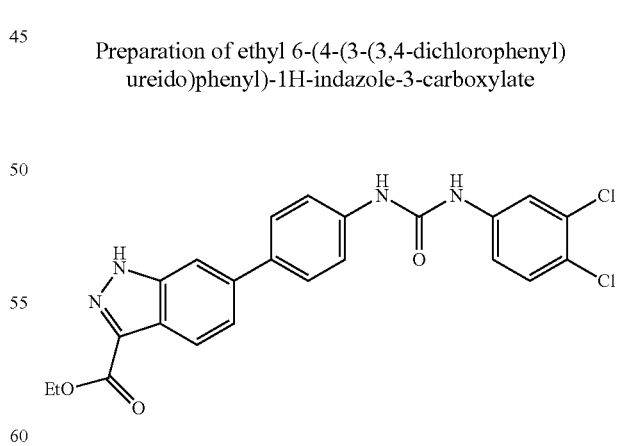

The mixture of ethyl 6-(4-aminophenyl)-1H-indazole-3-carboxylate (40 mg) and 3,4-dichlorophenylisocyanate in tetrahydrofuran (3 Ml; THF) was stirred at room temperature for 24 h. Ethyl acetate and saturated sodium bicarbonate solution were wadded. The aqueous layer was extracted with ethyl acetate and the combined organic layer was dried over magnesium sulfate and concentrated under reduced pressure. The residue was triturated by THF/hexane to give ethyl 6-(4-(3-(3,4-dichlorophenyl)ureido)phenyl)-1H-indazole-3-carboxylate (17.4 mg).

$^1$H NMR (400 MHz, DMSO-d$_6$) δ 1.39 (t, 3H), 4.40 (q, 2H), 7.59 (m, 4H), 7.71 (m, 2H), 7.81 (s, 1H), 8.12 (m, 3H), 9.51 (s, 1H), 9.21 (s, 1H), 13.95 (s, 1H).

Example 21

Preparation of ethyl 6-(4-(3-(4-chloro-3-(trifluoromethyl)phenyl)ureido)phenyl)-1H-indazole-3-carboxylate

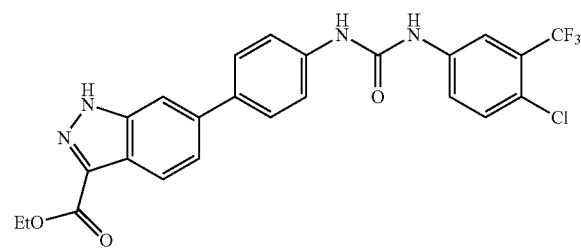 [SMILES: CCOC(=O)c1n[nH]c2cc(-c3ccc(NC(=O)Nc4ccc(Cl)c(C(F)(F)F)c4)cc3)ccc12]

The titled compound was prepared by repeating the procedure described in example 20.

$^1$H NMR (400 MHz, DMSO-d$_6$) δ 13.97 (br s, 1H), 9.65 (br s, 1H), 9.42 (br s, 1H), 8.15 (d, J=2.4 Hz, 1H), 8.10 (d, J=8.4 Hz, 1H), 7.81 (s, 1H), 7.70 (d, J=8.8 Hz, 2H), 7.66 (br s, 1H), 7.62 (br d, J=8.8 Hz, 4H), 4.41 (q, J=7.2 Hz, 2H), 1.39 (t, J=7.2 Hz, 3H).

Example 22

Preparation of ethyl 6-(4-(3-(3,5-bis(trifluoromethyl)phenyl)ureido)phenyl)-1H-indazole-3-carboxylate

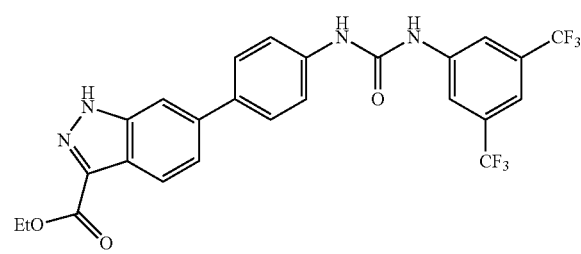 [SMILES: CCOC(=O)c1n[nH]c2cc(-c3ccc(NC(=O)Nc4cc(C(F)(F)F)cc(C(F)(F)F)c4)cc3)ccc12]

The titled compound was prepared by repeating the procedure described in example 20.

$^1$H NMR (400 MHz, DMSO-d$_6$) δ 1.39 (t, 3H), 4.40 (q, 2H), 7.34 (dd, 1H), 7.52 (d, 1H), 7.61 (m, 3H), 7.70 (dd, 2H), 7.80 (s, 1H), 7.90 (d, 1H), 8.09 (d, 1H), 9.13 (br, 2H), 13.94 (s, 1H).

Example 23

Preparation of ethyl 6-(4-(3-(3-(trifluoromethyl)phenyl)ureido)phenyl)-1H-indazole-3-carboxylate

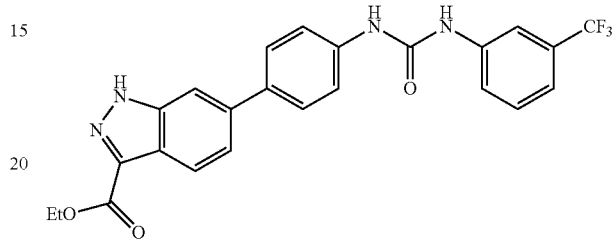

The titled compound was prepared by repeating the procedure described in example 20.

$^1$H NMR (400 MHz, DMSO-d$_6$) δ1.39 (t, 3H), 4.39 (q, 2H), 7.33 (d, 1H), 7.62 (m, 5H), 7.70 (d, 2H), 7.81 (s, 1H), 8.04 (s, 1H), 8.12 (d, 1H), 9.00 (s, 1H), 9.14 (s, 1H), 13.96 (s, 1H).

Example 24

Preparation of N-methyl-6-(4-(3-(trifluoromethyl)benzamido)phenyl)-1H-indazole-3-carboxamide Step 1: Preparation of 6-(4-(3-(trifluoromethyl)benzamido)phenyl)-1H-indazole-3-carboxylic acid

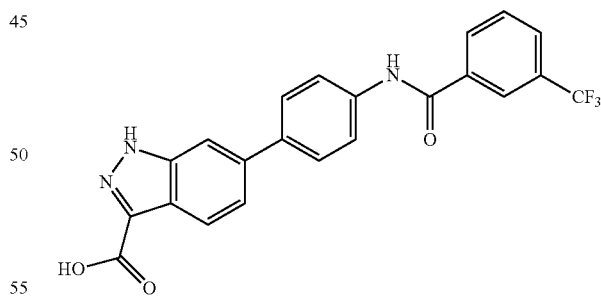

To a stirred solution of ethyl 6-(4-(3-(trifluoromethyl)benzamido)phenyl)-1H-indazole-3-carboxylate (12 mg, 25 µmol) in THF/water/methanol (10/1/1, 2.5 Ml), was added 1N aqueous sodium hydroxide solution (1.3 Ml). The mixture was stirred at 70° C. for 12 h and cooled to room temperature. The pH of solution was adjusted to 4-5 with 1N hydrochloric acid aqueous solution. The aqueous solution was extracted with ethyl acetate and the combined organic layer was washed with water, dried over magnesium sulfated, and concentrated under reduced pressure to give 6-(4-(3-(trifluoromethyl)benzamido)phenyl)-1H-indazole-3-carboxylic acid (13.5 mg), which was used in next step without purification.

Step 2: Preparation of N-methyl-6-(4-(3-(trifluoromethyl)benzamido)phenyl)-1H-indazole-3-carboxamide

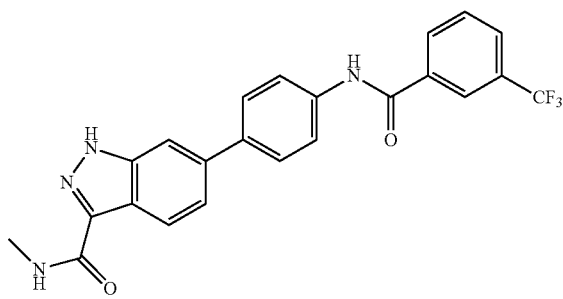 [SMILES: CNC(=O)c1n[nH]c2cc(-c3ccc(NC(=O)c4cccc(C(F)(F)F)c4)cc3)ccc12]

To a stirred solution of 6-(4-(3-(trifluoromethyl)benzamido)phenyl)-1H-indazole-3-carboxylic acid (26 mg, 61 μmol), methyl amine hydrochloride (6.2 mg, 92 μmol), HOBt (12 mg, 92 μmol), and triethylamine (43 μl, 0.3 mmol) in N,N-dimethylformamide (0.6 Ml), was added EDCI (18 mg, 92 μmol). After the mixture was stirred at 70° C. for 12 h, the mixture was cooled to room temperature, and ethyl acetate and saturated sodium bicarbonate solution were added. The aqueous layer was extracted with ethyl acetate and the combined organic layer was dried over magnesium sulfate and concentrated under reduced pressure. The residue was triturated in ethyl acetate/hexane to give N-methyl-6-(4-(3-(trifluoromethyl)benzamido)phenyl)-1H-indazole-3-carboxamide (20 mg).

$^1$H NMR (400 MHz, DMSO-d$_6$) δ13.62 (br s, 1H), 10.61 (s, 1H), 8.37 (q, J=4.8 Hz, 1H), 8.32 (s, 1H), 8.30 (d, J=7.6 Hz, 1H), 8.22 (d, J=8.4 Hz, 1H), 7.99 (d, J=8 Hz, 1H), 7.92 (d, J=8.8 Hz, 2H), 7.80 (m, 4H), 7.58 (d, J=8.8 Hz, 1H), 2.82 (d, J=4.8 Hz, 3H).

Example 25

Preparation of 6-(4-(5-(4-methoxyphenyl)furan-2-carboxamido)phenyl)-N-methyl-1H-indazole-3-carboxamide

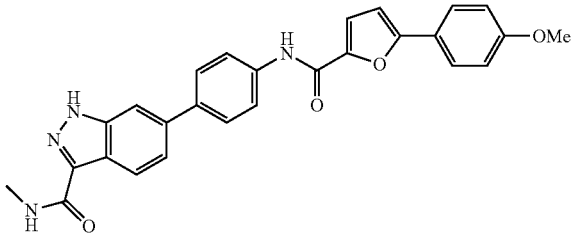 [SMILES: CNC(=O)c1n[nH]c2cc(-c3ccc(NC(=O)c4ccc(-c5ccc(OC)cc5)o4)cc3)ccc12]

The titled compound was prepared by repeating the procedure described in example 24.

$^1$H NMR (400 MHz, DMSO-d$_6$) δ 13.62 (br s, 1H), 10.26 (s, 1H), 8.39 (q, J=6 Hz, 1H), 8.22 (d, J=11.2 Hz, 1H), 7.93 (d, J=12 Hz, 2H), 7.91 (d, J=11.6 Hz, 2H), 7.80 (s, 1H), 7.79 (d, J=11.6 Hz, 2H), 7.59 (d, J=11.6 Hz, 1H), 7.42 (d, J=4.8 Hz, 1H), 7.07 (d, J=12 Hz, 2H), 7.05 (d, J=5.6 Hz, 1H), 3.83 (s, 3H), 2.83 (d, J=6.4 Hz, 3H).

Example 26

Preparation of 6-(4-(5-bromothiophene-2-carboxamido)phenyl)-N-methyl-1H-indazole-3-carboxamide

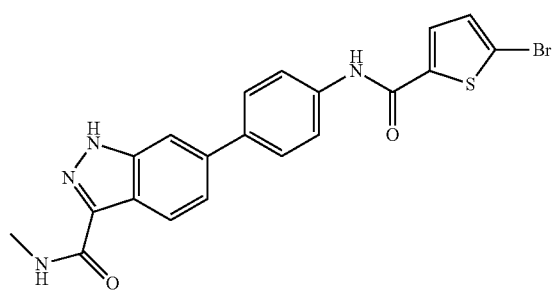 [SMILES: CNC(=O)c1n[nH]c2cc(-c3ccc(NC(=O)c4ccc(Br)s4)cc3)ccc12]

The titled compound was prepared by repeating the procedure described in example 24.

$^1$H NMR (400 MHz, DMSO-d$_6$) δ13.61 (br s, 1H), 10.42 (s, 1H), 8.38 (q, J=4.5 Hz, 1H), 8.21 (d, J=8.4 Hz, 1H), 7.90 (d, J=3.9 Hz, 1H), 7.85 (d, J=8.7 Hz, 2H), 7.79 (s, 1H), 7.77 (d, J=8.7 Hz, 2H), 7.57 (d, J=8.4 Hz, 1H), 7.39 (d, J=4.2 Hz, 1H), 2.82 (d, J=4.5 Hz, 3H).

Example 27

Preparation of 6-(4-(benzo[b]thiophene-2-carboxamido)phenyl)-N-methyl-1H-indazole-3-carboxamide

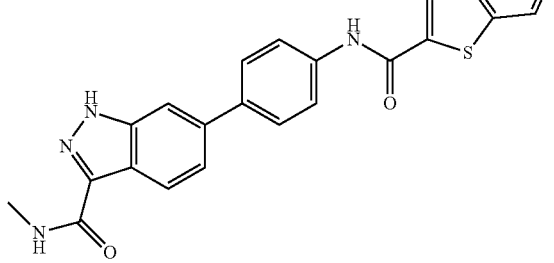

The titled compound was prepared by repeating the procedure described in example 24.

$^1$H NMR (400 MHz, DMSO-d$_6$) δ 13.62 (br s, 1H), 10.67 (s, 1H), 8.41 (s, 1H), 8.38 (m, 1H), 8.22 (d, J=8.4 Hz, 1H), 8.07-8.00 (m, 3H), 7.93 (d, J=8.7 Hz, 2H), 7.80 (d, J=8.7 Hz, 2H), 7.80 (s, 1H), 7.69 (d, J=8.4 Hz, 1H), 7.54-7.44 (m, 2H), 2.83 (d, J=4.8 Hz, 3H).

Example 28

Preparation of 6-(4-(3-(3,5-bis(trifluoromethyl)phenyl)ureido)phenyl)-N-methyl-1H-indazole-3-carboxamide

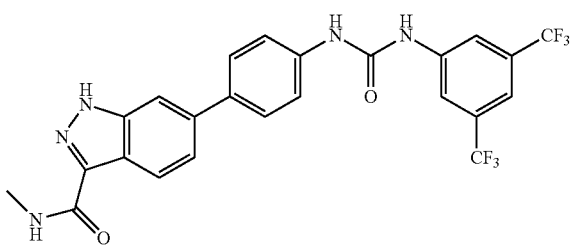 [SMILES: CNC(=O)c1n[nH]c2cc(-c3ccc(NC(=O)Nc4cc(C(F)(F)F)cc(C(F)(F)F)c4)cc3)ccc12]

The titled compound was prepared by repeating the procedure described in example 24.

$^1$H NMR (400 MHz, DMSO-d$_6$) δ2.81 (d, 3H), 7.36 (dd, 1H), 7.52 (m, 3H), 7.58 (m, 2H), 7.68 (dd, 2H), 7.74 (s, 1H), 7.90 (d, 1H), 8.18 (d, 1H), 8.35 (q, 1H), 9.20 (s, 1H), 9.30 (s, 1H), 13.94 (s, 1H) 1H), 8.09 (d, 1H), 9.13 (broad, 2H), 13.94 (s, 1H).

Example 29

Preparation of N-methyl-6-(4-(3-(3-(trifluoromethyl)phenyl)ureido)phenyl)-1H-indazole-3-carboxamide

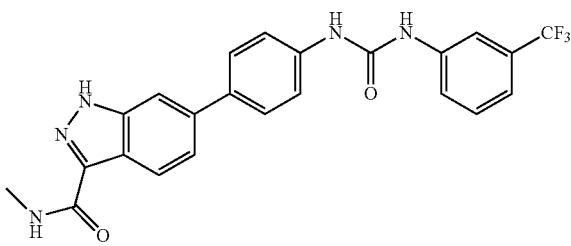 [SMILES: CNC(=O)c1n[nH]c2cc(-c3ccc(NC(=O)Nc4cccc(C(F)(F)F)c4)cc3)ccc12]

The titled compound was prepared by repeating the procedure described in example 24.

$^1$H NMR (400 MHz, DMSO-d$_6$) δ 2.83 (d, 3H), 7.30 (q, 1H), 7.52 (m, 2H), 7.60 (m, 3H), 7.69 (dd, 2H), 7.74 (s, 1H), 8.04 (s, 1H), 8.19 (d, 1H) 8.35 (q, 1H), 9.12 (s, 1H), 9.27 (s, 1H), 13.56 (s, 1H).

Example 30

Preparation of N-(2-morpholinoethyl)-6-(4-(3-(trifluoromethyl)benzamido)phenyl)-1H-indazole-3-carboxamide Step 1: Preparation of 6-(4-(3-(trifluoromethyl)benzamido)phenyl)-1H-indazole-3-carboxylic acid The titled compound was prepared by repeating the procedure described in step 1 in example 24.

Step 2: Preparation of N-(2-morpholinoethyl)-6-(4-(3-(trifluoromethyl)benzamido)phenyl)-1H-indazole-3-carboxamide To a stirred solution of 6-(4-(3-(trifluoromethyl)benzamido)phenyl)-1H-indazole-3-carboxylic acid (6 mg, 14 μmol), morpholinoethyl amine (3 μl, 17 μmol), HOBt (3 mg, 17 μmol), and triethylamine (4 μl, 28 μmol) in N,N-dimethylformamide (0.3 Ml), was added EDCI (4 mg, 21 μmol). After the mixture was stirred at 70° C. for 12 h, the mixture was cooled to room temperature, and ethyl acetate and saturated sodium bicarbonate solution were added. The aqueous layer was extracted with ethyl acetate and the combined organic layer was dried over magnesium sulfate and concentrated under reduced pressure. The residue was triturated in ethyl acetate/hexane to give N-(2-morpholinoethyl)-6-(4-(3-(trifluoromethyl)benzamido)phenyl)-1H-indazole-3-carboxamide (4 mg).

$^1$H NMR (400 MHz, DMSO-d$_6$) δ 13.61 (br s, 1H), 10.60 (s, 1H), 8.32 (s, 1H), 8.30 (d, J=7.6 Hz, 1H), 8.26 (t, J=8 Hz, 1H), 8.22 (d, J=8.4 Hz, 1H), 7.99 (d, J=8 Hz, 1H), 7.92 (d, J=8.8 Hz, 2H), 7.80 (m, 4H), 7.58 (d, J=8.8 Hz, 1H), 3.60-3.57 (m, 4H), 3.37-3.33 (m, 2H), 2.47 (m, 6H).

Example 31

Preparation of 6-(4-(5-bromothiophene-2-carboxamido)phenyl)-N-(2-morpholinoethyl)-1H-indazole-3-carboxamide

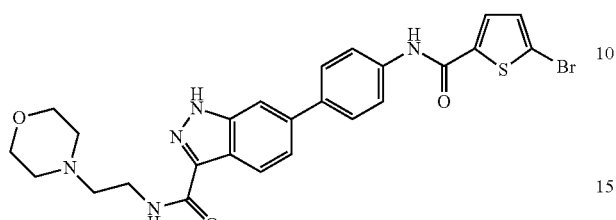

The titled compound was prepared by repeating the procedure described in example 30.

$^1$H NMR (400 MHz, DMSO-$d_6$) δ13.62 (s, 1H), 10.41 (s, 1H), 8.25 (t, J=5.6 Hz, 1H), 8.21 (d, J=8.8 Hz, 1H), 7.90 (d, J=4 Hz, 1H), 7.84 (d, J=8.8 Hz, 2H), 7.79 (s, 1H), 7.77 (d, J=8.8 Hz, 2H), 7.57 (dd, J=1.2, 8.4 Hz, 1H), 7.39 (d, J=4 Hz, 1H), 3.60-3.57 (m, 4H), 3.37-3.33 (m, 2H), 2.47 (m, 6H).

Example 32

Preparation of 6-(4-(benzo[b]thiophene-2-carboxamido)phenyl)-N-(2-morpholinoethyl)-1H-indazole-3-carboxamide

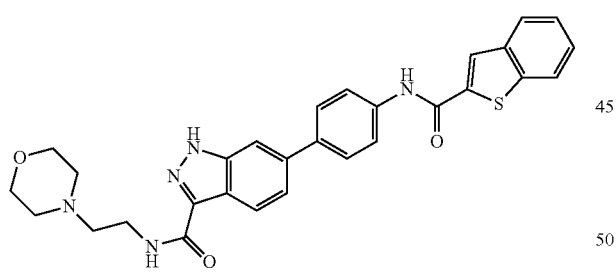

The titled compound was prepared by repeating the procedure described in example 30.

$^1$H NMR (400 MHz, DMSO-$d_6$) δ13.63 (s, 1H), 10.66 (s, 1H), 8.41 (s, 1H), 8.26 (t, J=5.6 Hz, 1H), 8.22 (d, J=8.4 Hz, 1H), 8.07 (br d, J=8.8 Hz, 2H), 8.03 (br d, J=7.2 Hz, 1H), 7.92 (d, J=8.8 Hz, 2H), 7.81 (s, 1H), 7.80 (d, J=8.8 Hz, 2H), 7.59 (br d, J=8.4 Hz, 1H), 7.52-7.48 (m, 2H), 3.59 (br t, J=4.4 Hz, 4H), 3.47-3.42 (m, 2H), 2.46-2.44 (m, 6H).

Example 33

Preparation of 6-(4-(2,5-dimethylfuran-3-carboxamido)phenyl)-N-(2-morpholinoethyl)-1H-indazole-3-carboxamide

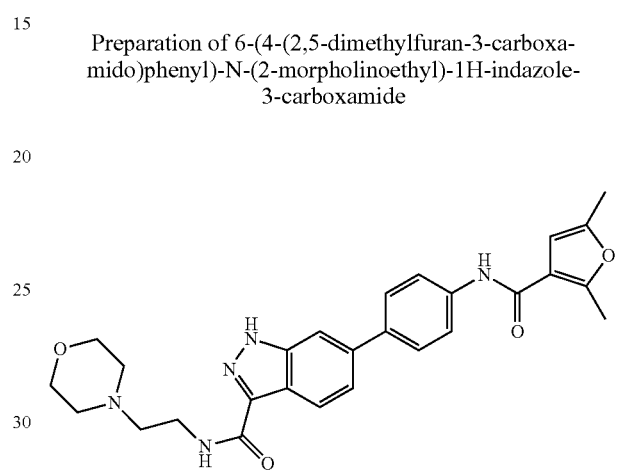

The titled compound was prepared by repeating the procedure described in example 30.

$^1$H NMR (300 MHz, DMSO-$d_6$) δ13.61 (brs, 1H), 9.72 (s, 1H), 8.26 (t, J=6 Hz, 1H), 8.21 (d, J=6.3 Hz, 1H), 7.86 (d, J=6.3 Hz, 2H), 7.78 (s, 1H), 7.73 (d, J=6.3 Hz, 2H), 7.56 (d, J=6.3 Hz, 1H), 6.69 (s, 1H), 3.58 (m, 4H), 3.45 (m, 2H), 2.52 (s, 3H), 2.45 (m, 6H), 2.28 (s, 3H).

Example 34

Preparation of 6-(4-(1-(4-methoxyphenyl)-5-(trifluoromethyl)-1H-pyrazole-4-carboxamido)phenyl)-N-(2-morpholinoethyl)-1H-indazole-3-carboxamide

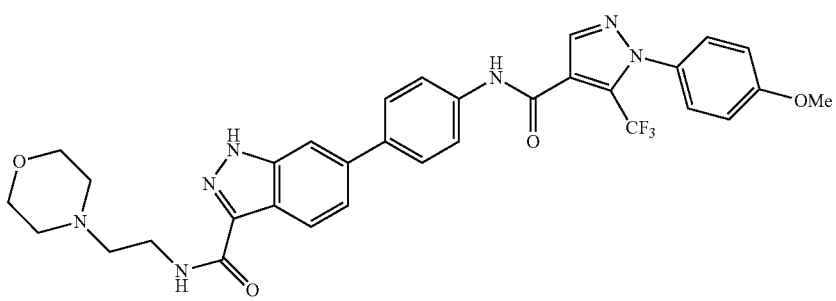 [SMILES: COc1ccc(-n2ncc(C(=O)Nc3ccc(-c4ccc5c(C(=O)NCCN6CCOCC6)n[nH]c5c4)cc3)c2C(F)(F)F)cc1]

The titled compound was prepared by repeating the procedure described in example 30.

$^1$H NMR (300 MHz, DMSO-d$_6$) δ13.67 (brs, 1H), 10.65 (s, 1H), 8.29 (s, 1H), 8.27 (t, J=5.7 Hz, 1H), 8.22 (d, J=9 Hz, 1H), 7.85 (d, J=8.7 Hz, 2H), 7.79 (s, 1H), 7.78 (d, J=8.7 Hz, 2H), 7.57 (d, J=8.4 Hz, 1H), 7.47 (d, J=8.7 Hz, 2H), 7.13 (d, J=8.7 Hz, 2H), 3.85 (s, 3H), 3.59 (m, 4H), 3.44 (m, 2H), 2.49 (m, 6H).

Example 35

Preparation of 6-(4-(5-bromothiophene-2-carboxamido)phenyl)-N-(3-(trifluoromethyl)phenyl)-1H-indazole-3-carboxamide

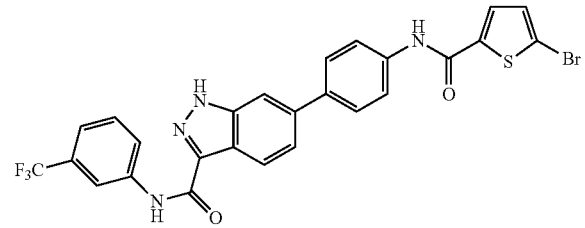 [SMILES: O=C(Nc1ccc(-c2ccc3c(C(=O)Nc4cccc(C(F)(F)F)c4)n[nH]c3c2)cc1)c1ccc(Br)s1]

The titled compound was prepared by repeating the procedure described in example 30.

$^1$H NMR (400 MHz, DMSO-d$_6$) δ13.94 (br s, 1H), 10.78 (s, 1H), 10.43 (s, 1H), 8.45 (s, 1H), 8.28 (d, J=8.4 Hz, 1H), 8.18 (br d, J=8 Hz, 1H), 7.91 (d, J=4 Hz, 1H), 7.87 (d, J=8.8 Hz, 2H), 7.86 (s, 1H), 7.81 (d, J=8.8 Hz, 2H), 7.65 (d, J=8.8 Hz, 1H), 7.60 (t, J=8 Hz, 1H), 7.45 (d, J=7.2 Hz, 1H), 7.40 (d, J=4 Hz, 1H).

Example 36

Preparation of 6-(4-(3-(3,4-dichlorophenyl)ureido)phenyl)-N-(2-morpholinoethyl)-1H-indazole-3-carboxamide

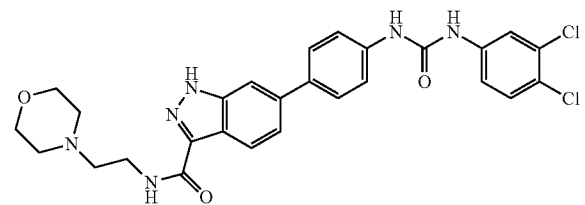 [SMILES: O=C(Nc1ccc(-c2ccc3c(C(=O)NCCN4CCOCC4)n[nH]c3c2)cc1)Nc1ccc(Cl)c(Cl)c1]

The titled compound was prepared by repeating the procedure described in example 30.

$^1$H NMR (400 MHz, DMSO-d$_6$) δ2.47 (m, 6H), 3.37-3.33 (m, 2H), 3.60-3.57 (m, 4H), 7.48 (dd, 1H), 7.67 (m, 5H), 7.75 (s, 1H), 8.18 (m, 3H), 8.24 (m, 1H), 9.63 (s, 1H), 10.00 (s, 1H), 13.59 (s, 1H).

Example 37

Preparation of N-methyl-6-(4-(pyridazine-4-carboxamido)phenyl)-1H-indazole-3-carboxamide Step 1: Preparation of 6-(4-nitrophenyl)-1H-indazole-3-carboxylic acid

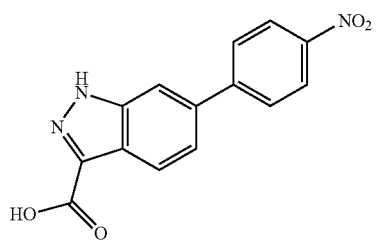 [SMILES: O=C(O)c1n[nH]c2cc(-c3ccc([N+](=O)[O-])cc3)ccc12]

To a stirred solution of ethyl 1-tert-butyl 3-ethyl 6-(4-nitrophenyl)-1H-indazole-1,3-dicarboxylate (200 mg, 0.49 mmol) in THF/water/methanol (10/1/1, 44 Ml), was added 1N aqueous sodium hydroxide solution (24 Ml). The mixture was stirred at 70° C. for 12 h and cooled to room temperature. The pH of solution was adjusted to 4-5 with 1N hydrochloric acid aqueous solution. The aqueous solution was extracted with ethyl acetate and the combined organic layer was washed with water, dried over magnesium sulfated, and concentrated under reduced pressure to give 6-(4-nitrophenyl)-1H-indazole-3-carboxylic acid (127 mg), which was used in next step without purification.

Step 2: Preparation of N-methyl-6-(4-nitrophenyl)-1H-indazole-3-carboxamide

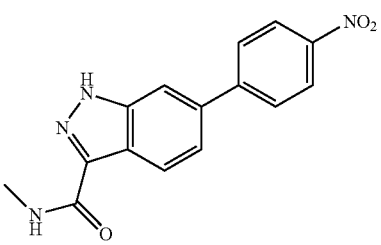 [SMILES: CNC(=O)c1n[nH]c2cc(-c3ccc([N+](=O)[O-])cc3)ccc12]

To a stirred solution of 6-(4-nitrophenyl)-1H-indazole-3-carboxylic acid (140 mg, 0.5 mmol), methyl amine hydrochloride (45 mg, 0.6 mmol), HOBt (80 mg, 0.6 mmol), and triethylamine (0.3 Ml, 2 mmol) in N,N-dimethylformamide (5 Ml), was added EDCI (142 mg, 0.7 mmol). After the mixture was stirred at 70° C. for 12 h, the mixture was cooled to room temperature, and ethyl acetate and saturated sodium bicarbonate solution were added. The aqueous layer was extracted with ethyl acetate and the combined organic layer was dried over magnesium sulfate and concentrated under reduced pressure to give N-methyl-6-(4-nitrophenyl)-1H-indazole-3-carboxamide (70 mg).

$^1$H NMR (400 MHz, DMSO-d$_6$) δ13.78 (s, 1H), 8.41 (q, J=4.8 Hz, 1H), 8.34 (d, J=8.8 Hz, 2H), 8.29 (d, J=8 Hz, 1H), 8.06 (d, J=8.8 Hz, 2H), 7.96 (s, 1H), 7.65 (dd, J=1.2, 8.8 Hz, 1H), 2.83 (d, J=4.8 Hz, 3H).

Step 3: Preparation of 6-(4-aminophenyl)-N-methyl-1H-indazole-3-carboxamide

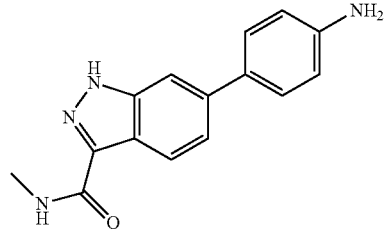

To a stirred solution of N-methyl-6-(4-nitrophenyl)-1H-indazole-3-carboxamide (154 mg, 0.52 mmol) in ethanol (10 Ml), was added SnCl$_2$ (588 mg, 2.6 mmol) and the mixture was stirred at 80° C. for 3 h. The mixture was cooled to rt and saturated sodium bicarbonate aqueous solution was added. The organic layer was extracted three times and the combined organaic layer was dried over sodium sulfate and concentrated under reduced pressure. The residue was triturated in ethyl acetate and hexane to give 6-(4-aminophenyl)-N-methyl-1H-indazole-3-carboxamide (130 mg).

$^1$H NMR (400 MHz, DMSO-d$_6$) δ 13.43 (s, 1H), 8.31 (q, J=4.8 Hz, 1H), 8.12 (d, J=8.8 Hz, 1H), 7.66 (s, 1H), 7.45 (d, J=8.4 Hz, 1H), 7.44 (d, J=8.4 Hz, 2H), 6.66 (d, J=8 Hz, 2H), 2.81 (d, J=4 Hz, 3H).

Step 4: Preparation of N-methyl-6-(4-(pyridazine-4-carboxamido)phenyl)-1H-indazole-3-carboxamide

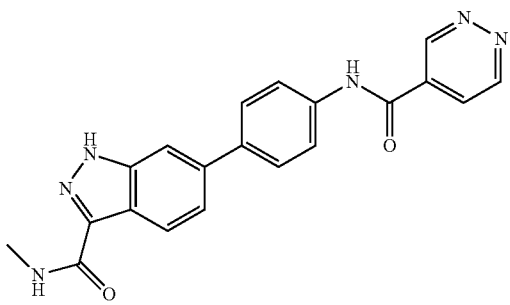 [SMILES: CNC(=O)c1n[nH]c2cc(-c3ccc(NC(=O)c4ccnnc4)cc3)ccc12]

To a stirred solution of 6-(4-aminophenyl)-N-methyl-1H-indazole-3-carboxamide (15 mg, 56 μmol), pyridazine-4-carboxylic acid (9 mg, 73 μmol), triethylamine (24 μl, 169 μmol), and HOBt (10 mg, 73 μmol) in N,N-dimethylformamide (0.6 Ml), was added EDCI (16 mg, 85 μmol). The mixture was stirred at 70° C. for 12 h. The mixture cooled to room temperature and ethyl acetate and water were added.

The mixture was extracted with ethyl acetate three times. The combined organic layer was washed with saturated sodium bicarbonate solution, dried over sodium sulfate, and concentrated under reduced pressure. The residue was triturated by ethylacetate/hexane to give N-methyl-6-(4-(pyridazine-4-carboxamido)phenyl)-1H-indazole-3-carboxamide (12 mg).

$^1$H NMR (400 MHz, DMSO-d$_6$) δ 13.61 (br s, 1H), 10.84 (br s, 1H), 9.68 (s, 1H), 9.51 (d, J=4 Hz, 1H), 8.38 (q, J=4.4 Hz, 1H), 8.22 (d, J=8.4 Hz, 1H), 8.15 (dd, J=2.4, 5.2 Hz, 1H), 7.91 (d, J=8.4 Hz, 2H), 7.81 (d, J=8.4 Hz, 2H), 7.80 (s, 1H), 7.58 (dd, J=1.2, 8.4 Hz, 1H), 2.83 (d, J=4.8 Hz, 3H).

Example 38

Preparation of 5-methyl-N-(4-(3-(methylcarbamoyl)-1H-indazol-6-yl)phenyl)isoxazole-3-carboxamide

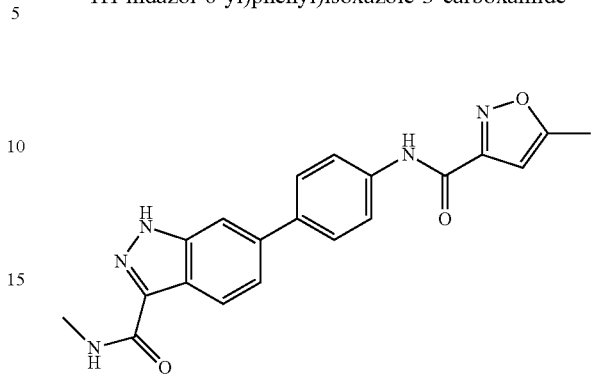

The titled compound was prepared by repeating the procedure described in example 37.

$^1$H NMR (400 MHz, DMSO-d$_6$) δ13.59 (br s, 1H), 10.78 (s, 1H), 8.37 (q, J=4.4 Hz, 1H), 8.21 (d, J=8.4 Hz, 1H), 7.92 (d, J=8.4 Hz, 2H), 7.78 (s, 1H), 7.77 (d, J=8.4 Hz, 2H), 7.56 (d, J=8.4 Hz, 1H), 6.69 (s, 1H), 2.82 (d, J=4.4 Hz, 3H), 2.51 (s, 3H)

Example 39

Preparation of N-methyl-6-(4-(3-(4-methyl-1H-imidazol-1-yl)-5-(trifluoromethyl)benzamido)phenyl)-1H-indazole-3-carboxamide

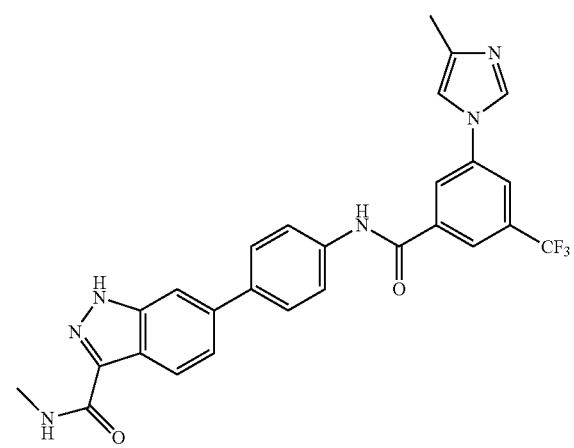 [SMILES: CNC(=O)c1n[nH]c2cc(-c3ccc(NC(=O)c4cc(-n5cnc(C)c5)cc(C(F)(F)F)c4)cc3)ccc12]

The titled compound was prepared by repeating the procedure described in example 38.

$^1$H NMR (400 MHz, DMSO-d$_6$) δ 13.58 (br s, 1H), 10.64 (s, 1H), 8.48 (s, 1H), 8.42 (s, 1H), 8.37 (q, J=4.8 Hz, 1H), 8.26 (s, 1H), 8.22 (d, J=8.4 Hz, 1H), 8.20 (s, 1H), 7.92 (d, J=8.8 Hz, 2H), 7.82 (d, J=8.8 Hz, 2H), 7.81 (s, 1H), 7.74 (s, 1H), 7.59 (d, J=8.4 Hz, 1H), 2.83 (d, J=4.8 Hz, 3H), 2.20 (s, 3H).

Example 40

Preparation of N-methyl-6-(4-(4-(1-methylpiperidin-4-yloxy)-3-(trifluoromethyl)benzamido)phenyl)-1H-indazole-3-carboxamide

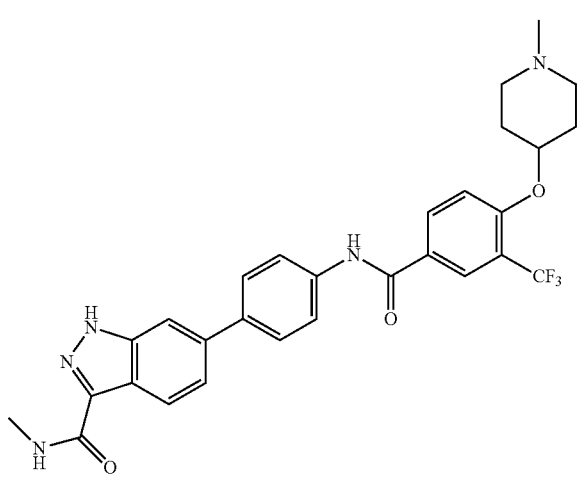 [SMILES: CNC(=O)c1n[nH]c2cc(-c3ccc(NC(=O)c4ccc(OC5CCN(C)CC5)c(C(F)(F)F)c4)cc3)ccc12]

The titled compound was prepared by repeating the procedure described in example 37.

$^{1}$H NMR (400 MHz, DMSO-$d_6$) δ13.59 (s, 1H), 10.42 (s, 1H), 8.27 (s, 1H), 8.26 (d, J=7.6 Hz, 1H), 8.22 (d, J=8 Hz, 1H), 7.90 (d, J=8.8 Hz, 2H), 7.78 (s, 1H), 7.77 (d, J=8.8 Hz, 2H), 7.57 (d, J=9.2 Hz, 1H), 7.49 (d, J=9.2 Hz, 1H), 4.79 (m, 1H), 2.83 (d, J=4.8 Hz, 3H), 2.31 (m, 4H), 2.21 (s, 3H), 1.98 (m, 2H), 1.75 (m, 2H).

Example 41

Preparation of N-(4-(3-(methylcarbamoyl)-1H-indazol-6-yl)phenyl)thiazole-4-carboxamide

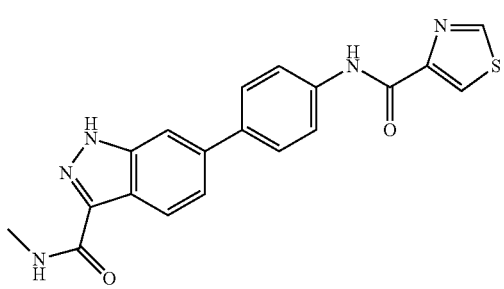 [SMILES: CNC(=O)c1n[nH]c2cc(-c3ccc(NC(=O)c4cscn4)cc3)ccc12]

The titled compound was prepared by repeating the procedure described in example 37.

$^{1}$H NMR (400 MHz, DMSO-$d_6$) δ13.61 (br s, 1H), 10.50 (s, 1H), 9.29 (d, J=2 Hz, 1H), 8.53 (d, J=1.6 Hz, 1H), 8.38 (q, J=4.4 Hz, 1H), 8.21 (d, J=8.4 Hz, 1H), 8.00 (d, J=8.8 Hz, 2H), 7.79 (s, 1H), 7.76 (d, J=8.4 Hz, 2H), 7.57 (dd, J=1.6, 8.4 Hz, 1H), 2.82 (d, J=4.8 Hz, 3H).

Example 42

Preparation of methyl 5-(4-aminophenyl)-1H-indazole-3-carboxylate

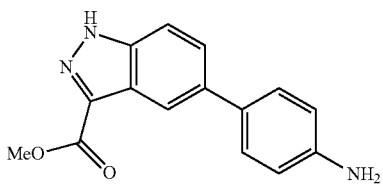

The titled compound was prepared by repeating the procedure described in example 1.

$^{1}$H NMR (400 MHz, DMSO-$d_6$) δ 13.88 (s, 1H), 8.11 (s, 1H), 7.65 (s, 2H), 7.38 (d, J=8.4 Hz, 2H), 6.67 (d, J=8.4 Hz, 2H), 5.23 (s, 2H), 3.93 (s, 3H).

Example 43

Preparation of methyl 5-(4-(3-(4-chloro-3-(trifluoromethyl)phenyl)ureido)phenyl)-1H-indazole-3-carboxylate

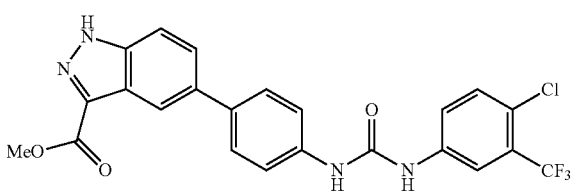 [SMILES: COC(=O)c1n[nH]c2ccc(-c3ccc(NC(=O)Nc4ccc(Cl)c(C(F)(F)F)c4)cc3)cc12]

The titled compound was prepared by repeating the procedure described in example 20.

$^{1}$H NMR (400 MHz, DMSO-$d_6$) δ13.97 (s, 1H), 9.26 (s, 1H), 9.08 (s, 1H), 8.45 (d, J=8 Hz, 1H), 8.42 (d, J=2.4 Hz, 1H), 8.36 (s, 1H), 8.18 (d, J=8.4 Hz, 1H), 8.14 (s, 1H), 8.04 (d, J=8 Hz, 1H), 7.75 (d, J=8.8 Hz, 1H), 7.65 (m, 3H), 4.05 (s, 3H).

Example 44

Preparation of ethyl 6-(3-aminophenyl)-1H-indazole-3-carboxylate

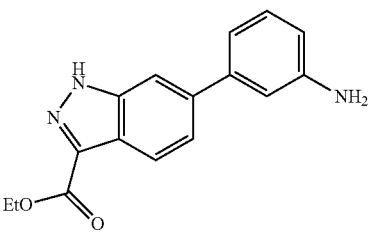 [SMILES: CCOC(=O)c1n[nH]c2cc(-c3cccc(N)c3)ccc12]

The titled compound was prepared by repeating the procedure described in example 1.

$^{1}$H NMR (400 MHz, DMSO-$d_6$) δ 13.80 (s, 1H), 8.03 (d, J=8.4 Hz, 1H), 7.66 (s, 1H), 7.53 (dd, J=1.2, 8.4 Hz, 1H), 7.44 (d, J=8.4 Hz, 2H), 6.67 (d, J=8.4 Hz, 1H), 5.30 (s, 2H), 4.39 (q, J=7.2 Hz, 2H), 1.38 (t, J=7.2 Hz, 3H).

Example 45

Preparation of ethyl 6-(3-(3-(trifluoromethyl)benzamido)phenyl)-1H-indazole-3-carboxylate

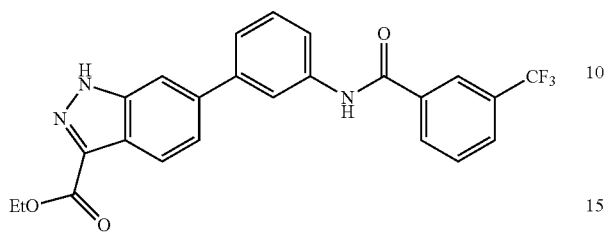

The titled compound was prepared by repeating the procedure described in example 2.

$^1$H NMR (400 MHz, DMSO-d$_6$) δ0.60 (s, 1H), 8.34 (s, 1H), 8.30 (d, J=8.8 Hz, 1H), 8.18 (s, 1H), 8.16 (d, J=8.4 Hz, 1H), 7.97 (d, J=7.2 Hz, 1H), 7.86-7.79 (m, 3H), 7.63 (d, J=8.8 Hz, 1H), 7.52 (m, 2H), 4.43 (q, J=7.2 Hz, 2H), 1.39 (t, J=7.2 Hz, 3H).

Example 46

Preparation of ethyl 6-(3-(5-methylisoxazole-3-carboxamido)phenyl)-1H-indazole-3-carboxylate

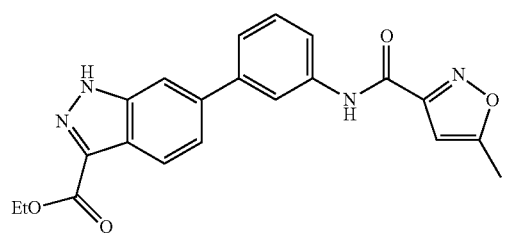 [SMILES: CCOC(=O)c1n[nH]c2cc(-c3cccc(NC(=O)c4cc(C)on4)c3)ccc12]

The titled compound was prepared by repeating the procedure described in example 2.

$^1$H NMR (400 MHz, DMSO-d$_6$) δ 14.02 (s, 1H), 10.76 (s, 1H), 8.21 (s, 1H), 8.15 (d, J=8.8 Hz, 1H), 7.83 (s, 1H), 7.62 (d, J=8.4 Hz, 1H), 7.51 (m, 3H), 6.69 (s, 1H), 4.40 (q, J=7.2 Hz, 2H), 2.51 (s, 3H), 1.39 (t, J=7.2 Hz, 3H).

Example 47

Preparation of ethyl 6-(3-(benzo[b]thiophene-2-carboxamido)phenyl)-1H-indazole-3-carboxylate

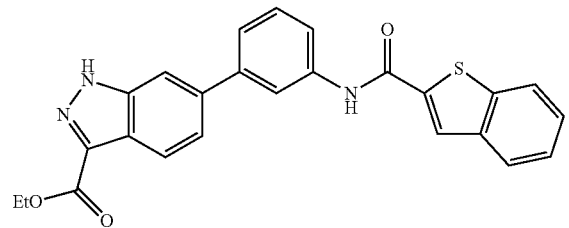 [SMILES: CCOC(=O)c1n[nH]c2cc(-c3cccc(NC(=O)c4cc5ccccc5s4)c3)ccc12]

The titled compound was prepared by repeating the procedure described in example 2.

$^1$H NMR (400 MHz, DMSO-d$_6$) δ14.03 (s, 1H), 10.66 (s, 1H), 8.41 (s, 1H), 8.20 (s, 1H), 8.17 (d, J=8.4 Hz, 1H), 8.07 (d, J=6.8 Hz, 1H), 8.03 (d, J=6.8 Hz, 1H), 7.86 (s, 1H), 7.83 (m, 1H), 7.64 (d, J=9.6 Hz, 1H), 7.50 (m, 4H), 4.42 (q, J=6.8 Hz, 2H), 1.40 (t, J=6.8 Hz, 3H).

Example 48

Preparation of ethyl 6-(3-(2-(3,4-dimethoxyphenyl)acetamido)phenyl)-1H-indazole-3-carboxylate

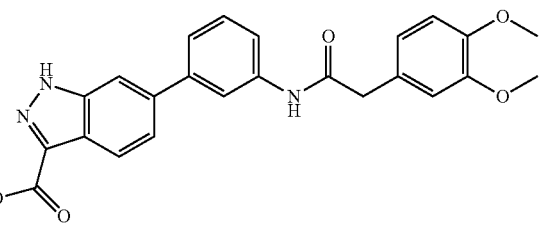

The titled compound was prepared by repeating the procedure described in example 2.

$^1$H NMR (400 MHz, DMSO-d$_6$) δ 13.98 (s, 1H), 10.25 (s, 1H), 8.13 (d, J=8.4 Hz, 1H), 8.02 (s, 1H), 7.78 (s, 1H), 7.57 (d, J=8.4 Hz, 1H), 7.42 (d, J=5.2 Hz, 2H), 6.96 (s, 1H), 6.89 (t, J=8.4 Hz, 1H), 6.86 (d, J=8.4 Hz, 1H), 4.41 (q, J=7.2 Hz, 2H), 3.75 (s, 3H), 3.72 (s, 3H), 3.59 (s, 2H), 1.39 (t, J=7.2 Hz, 3H).

Example 49

Preparation of ethyl 6-(3-(5-bromothiophene-2-carboxamido)phenyl)-1H-indazole-3-carboxylate

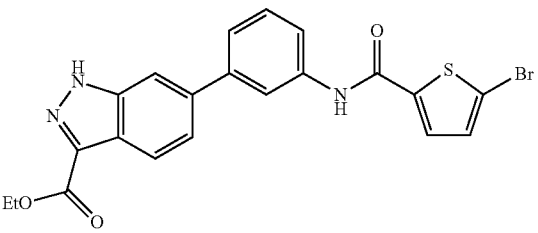 [SMILES: CCOC(=O)c1n[nH]c2cc(-c3cccc(NC(=O)c4ccc(Br)s4)c3)ccc12]

The titled compound was prepared by repeating the procedure described in example 2.

$^1$H NMR (400 MHz, DMSO-d$_6$) δ14.01 (s, 1H), 10.42 (s, 1H), 8.15 (d, J=8.4 Hz, 1H), 8.11 (s, 1H), 7.91 (d, J=4.4 Hz, 1H), 7.83 (s, 1H), 7.76 (br d, J=4.8 Hz, 1H), 7.62 (br d, J=8.8 Hz, 1H), 7.51 (m, 2H), 7.40 (d, J=4 Hz, 1H), 4.41 (q, J=7.2 Hz, 2H), 1.39 (t, J=7.2 Hz, 3H).

Example 50

Preparation of N-(2-morpholinoethyl)-6-(3-(3-(trifluoromethyl)benzamido)phenyl)-1H-indazole-3-carboxamide

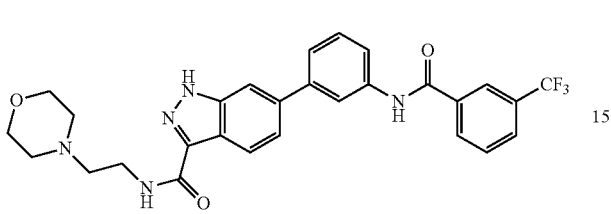

The titled compound was prepared by repeating the procedure described in example 2.

$^1$H NMR (400 MHz, DMSO-$d_6$) δ 13.67 (s, 1H), 10.48 (s, 1H), 8.29-8.24 (m, 2H), 8.15 (s, 1H), 7.84 (br d, J=7.2 Hz, 1H), 7.79 (s, 1H), 7.76 (s, 1H), 7.69 (s, 1H), 7.57-7.52 (m, 2H), 7.41 (s, 1H), 3.78 (m, 4H), 3.58 (m, 4H), 3.44 (m, 2H), 3.32 (m, 4H), 2.43 (m, 6H).

Example 51

Preparation of methyl 6-(3-aminophenyl)-1H-indazole-3-carboxylate

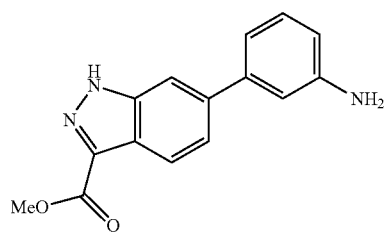 [SMILES: COC(=O)c1n[nH]c2cc(-c3cccc(N)c3)ccc12]

The titled compound was prepared by repeating the procedure described in example 1.

$^1$H NMR (400 MHz, DMSO-$d_6$) δ 13.95 (s, 1H), 8.09 (d, J=8.4 Hz, 1H), 7.71 (s, 1H), 7.53 (dd, J=1.6, 8.8 Hz, 1H), 7.13 (t, J=8 Hz, 1H), 6.91 (br s, 1H), 6.85 (d, J=8.4 Hz, 1H), 6.60 (br d, J=7.2 Hz, 1H), 5.22 (br s, 2H), 3.93 (s, 3H).

Example 52

Preparation of methyl 6-(3-(3-morpholino-5-(trifluoromethyl)benzamido)phenyl)-1H-indazole-3-carboxylate The titled compound was prepared by repeating the procedure described in example 2.

$^1$H NMR (300 MHz, DMSO-$d_6$) δ 14.05 (br s, 1H), 10.50 (s, 1H), 8.16 (d, J=8.7 Hz, 1H), 8.15 (s, 1H), 7.85 (br s, 2H), 7.76 (s, 1H), 7.69 (s, 1H), 7.64 (d, J=8.7 Hz, 1H), 7.50 (m, 2H), 7.41 (s, 1H), 3.94 (s, 3H), 3.77 (m, 4H), 3.31 (m, 4H).

Example 53

Preparation of ethyl 6-(5-amino-2-methylphenyl)-1H-indazole-3-carboxylate

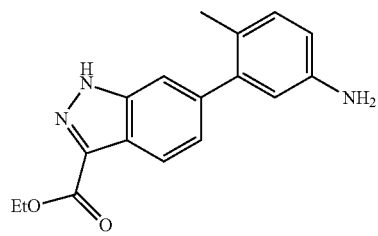 [SMILES: CCOC(=O)c1n[nH]c2cc(-c3cc(N)ccc3C)ccc12]

The titled compound was prepared by repeating the procedure described in example 1.

$^1$H NMR (400 MHz, DMSO-$d_6$) δ13.89 (s, 1H), 8.06 (d, J=8.4 Hz, 1H), 7.46 (s, 1H), 7.24 (d, J=8.4 Hz, 1H), 6.95 (d, J=8 Hz, 1H), 6.51 (d, J=8 Hz, 1H), 6.50 (s, 1H), 4.96 (br s, 1H), 4.40 (q, J=7.2 Hz, 2H), 2.05 (s, 3H), 1.38 (t, J=7.2 Hz, 3H).

Example 54

Preparation of ethyl 6-(3-(3-(2,3-dichlorophenyl)ureido)phenyl)-1H-indazole-3-carboxylate

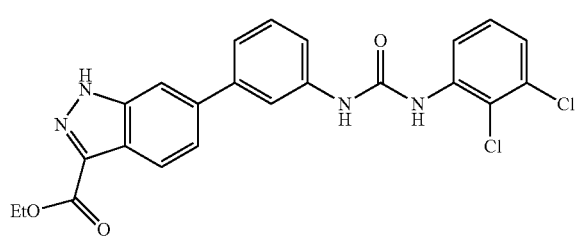 [SMILES: CCOC(=O)c1n[nH]c2cc(-c3cccc(NC(=O)Nc4cccc(Cl)c4Cl)c3)ccc12]

The titled compound was prepared by repeating the procedure described in example 20.

$^1$H NMR (400 MHz, DMSO-d$_6$) δ 13.99 (s, 1H), 9.67 (s, 1H), 8.54 (s, 1H), 8.19 (dd, J=1.6, 8 Hz, 1H), 8.14 (d, J=8.8 Hz, 1H), 7.93 (s, 1H), 7.82 (s, 1H), 7.60 (d, J=8.8 Hz, 1H), 7.45-7.29 (m, 5H), 4.41 (q, J=7.2 Hz, 2H), 1.39 (t, J=7.2 Hz, 3H).

Example 55

Preparation of ethyl 6-(3-(3-(3,4-dichlorophenyl)ureido)phenyl)-1H-indazole-3-carboxylate

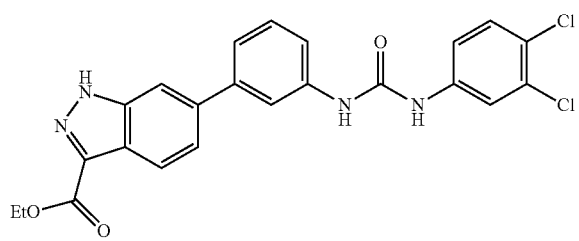 [SMILES: CCOC(=O)c1n[nH]c2cc(-c3cccc(NC(=O)Nc4ccc(Cl)c(Cl)c4)c3)ccc12]

The titled compound was prepared by repeating the procedure described in example 20.

$^1$H NMR (400 MHz, DMSO-d$_6$) δ13.97 (s, 1H), 9.14 (s, 1H), 9.03 (s, 1H), 8.15 (d, J=8.4 Hz, 1H), 7.93 (d, J=8.8 Hz, 2H), 7.82 (s, 1H), 7.60 (d, J=8.4 Hz, 1H), 7.53 (d, J=8.8 Hz, 1H), 7.37 (m, 4H), 4.41 (q, J=7.2 Hz, 2H), 1.41 (t, J=7.2 Hz, 3H).

Example 56

Preparation of methyl 6-(3-(3-(2,4-dimethylphenyl)ureido)phenyl)-1H-indazole-3-carboxylate

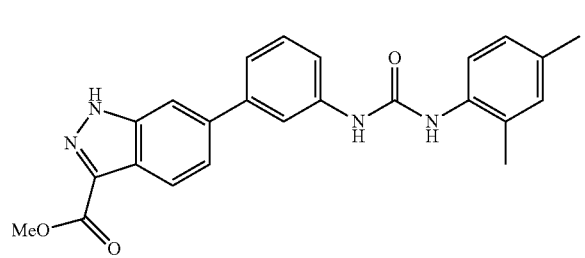 [SMILES: COC(=O)c1n[nH]c2cc(-c3cccc(NC(=O)Nc4ccc(C)cc4C)c3)ccc12]

The titled compound was prepared by repeating the procedure described in example 20.

$^1$H NMR (400 MHz, DMSO-d$_6$) δ 14.04 (br s, 1H), 9.13 (s, 1H), 8.13 (d, J=8.4 Hz, 1H), 7.92 (s, 2H), 7.81 (s, 1H), 7.67 (d, J=8 Hz, 1H), 7.60 (d, J=8.8 Hz, 1H), 7.41 (s, 1H), 7.40 (t, J=8 Hz, 1H), 6.99 (s, 1H), 6.95 (d, J=8 Hz, 1H), 3.94 (s, 3H), 2.23 (s, 3H), 2.21 (s, 3H).

Example 57

Preparation of ethyl 6-(5-(3-(4-chloro-3-(trifluoromethyl)phenyl)ureido)-2-methylphenyl)-1H-indazole-3-carboxylate

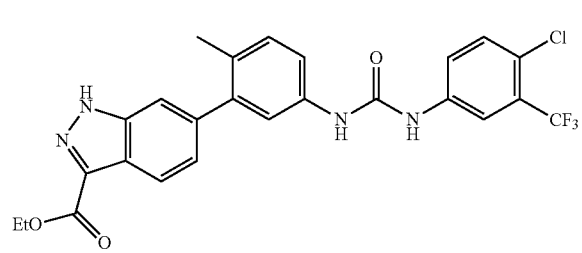 [SMILES: CCOC(=O)c1n[nH]c2cc(-c3cc(NC(=O)Nc4ccc(Cl)c(C(F)(F)F)c4)ccc3C)ccc12]

The titled compound was prepared by repeating the procedure described in example 20.

$^1$H NMR (400 MHz, DMSO-d$_6$) δ13.95 (s, 1H), 9.17 (s, 1H), 8.86 (s, 1H), 8.11 (d, J=8 Hz, 1H), 8.10 (s, 1H), 7.62-7.58 (m, 2H), 7.54 (s, 1H), 7.46 (d, J=2 Hz, 1H), 7.36 (dd, J=2.4, 8.4 Hz, 1H), 7.30 (d, J=8.4 Hz, 1H), 7.24 (d, J=8.4 Hz, 1H), 4.41 (q, J=7.2 Hz, 2H), 2.18 (s, 3H), 1.39 (t, J=7.2 Hz, 3H).

Example 58

Preparation of 6-(3-(3-(4-chloro-3-(trifluoromethyl)phenyl)ureido)phenyl)-N-(2-morpholinoethyl)-1H-indazole-3-carboxamide

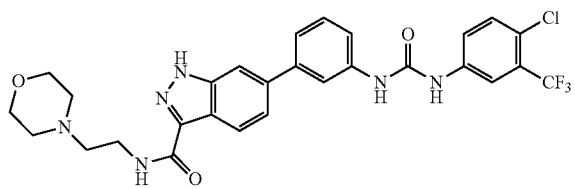 [SMILES: O=C(Nc1cccc(-c2ccc3c(C(=O)NCCN4CCOCC4)n[nH]c3c2)c1)Nc1ccc(Cl)c(C(F)(F)F)c1]

The titled compound was prepared by repeating the procedure described in example 30.

$^1$H NMR (400 MHz, DMSO-d$_6$) δ13.61 (s, 1H), 8.25-8.22 (m, 2H), 8.16 (s, 1H), 7.96 (s, 1H), 7.75 (s, 1H), 7.70 (d, J=11.2 Hz, 1H), 7.60 (d, J=8.8 Hz, 1H), 7.52 (d, J=8.4 Hz, 1H), 7.46 (d, J=8 Hz, 1H), 7.41 (d, J=7.6 Hz, 1H), 7.36 (t, J=7.6 Hz, 1H), 3.58 (m, 4H), 3.36 (m, 2H), 2.40 (m, 6H).

Example 59

Preparation of 6-(3-(3-morpholino-5-(trifluoromethyl)benzamido)phenyl)-N-(2-morpholinoethyl)-1H-indazole-3-carboxamide

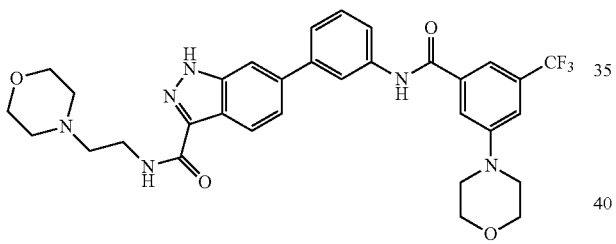

The titled compound was prepared by repeating the procedure described in example 30.

$^1$H NMR (400 MHz, DMSO-d$_6$) δ13.67 (s, 1H), 10.48 (s, 1H), 8.29-8.24 (m, 2H), 8.15 (s, 1H), 7.84 (br d, J=7.2 Hz, 1H), 7.79 (s, 1H), 7.76 (s, 1H), 7.56 (br d, J=8.1 Hz, 1H), 7.52 (s, 1H), 7.51 (d, J=7.6 Hz, 1H), 7.41 (s, 1H), 3.78 (m, 4H), 3.58 (m, 4H), 3.44 (m, 2H), 3.33 (m, 4H), 2.43 (m, 6H).

Example 60

Preparation of 6-(3-(3-(2,3-dichlorophenyl)ureido)phenyl)-N-(2-morpholinoethyl)-1H-indazole-3-carboxamide

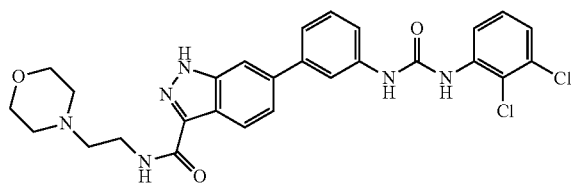 [SMILES: O=C(Nc1cccc(-c2ccc3c(C(=O)NCCN4CCOCC4)n[nH]c3c2)c1)Nc1cccc(Cl)c1Cl]

The titled compound was prepared by repeating the procedure described in example 30.

$^1$H NMR (400 MHz, DMSO-d$_6$) δ13.98 (s, 1H), 9.66 (s, 1H), 8.54 (s, 1H), 8.19 (dd, J=1.6, 8 Hz, 1H), 8.14 (d, J=8.8 Hz, 1H), 7.93 (s, 1H), 7.82 (s, 1H), 7.61 (d, J=8.8 Hz, 1H), 7.45-7.30 (m, 5H), 4.41 (q, J=7.2 Hz, 2H), 1.39 (t, J=7.2 Hz, 3H).

Example 61

Preparation of 6-(3-(3-(2,3-dichlorophenyl)ureido)phenyl)-N-ethyl-1H-indazole-3-carboxamide

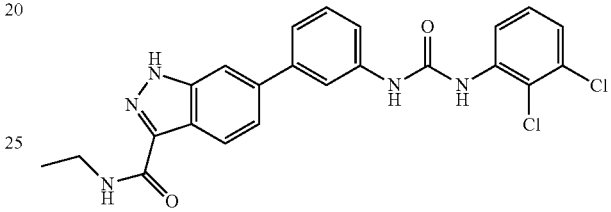

The titled compound was prepared by repeating the procedure described in example 30.

$^1$H NMR (400 MHz, DMSO-d$_6$) δ 13.61 (s, 1H), 9.65 (s, 1H), 8.53 (s, 1H), 8.43 (br s, 1H), 8.23 (m, 2H), 7.93 (s, 1H), 7.76 (s, 1H), 7.53-7.28 (m, 5H), 6.86 (s, 1H), 3.60 (br s, 2H), 1.13 (br s, 3H).

Example 62

Preparation of 6-(3-(3-(3,4-dichlorophenyl)ureido)phenyl)-N-ethyl-1H-indazole-3-carboxamide

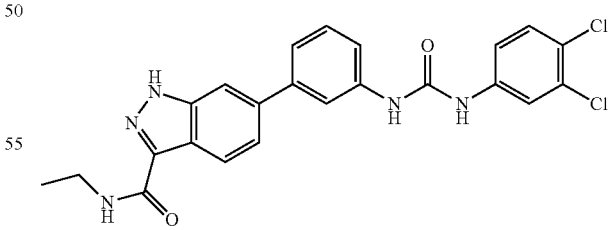

The titled compound was prepared by repeating the procedure described in example 30.

$^1$H NMR (400 MHz, DMSO-d$_6$) δ13.60 (s, 1H), 9.25 (br s, 1H), 9.13 (br s, 1H), 8.43 (br t, J=5.2 Hz, 1H), 8.26 (d, J=9.2 Hz, 1H), 7.93 (br d, J=7.2 Hz, 2H), 7.75 (s, 1H), 7.52 (br d, J=8.4 Hz, 2H), 7.38 (m, 4H), 3.31 (q, J=7.2 Hz, 2H), 1.15 (t, J=7.2 Hz, 3H).

Example 63

Preparation of 6-(3-(3-(2,4-dimethylphenyl)ureido)phenyl)-N-ethyl-1H-indazole-3-carboxamide

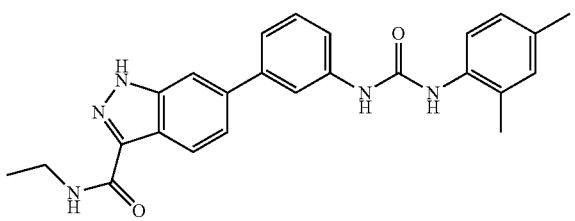 [SMILES: CCNC(=O)c1n[nH]c2cc(-c3cccc(NC(=O)Nc4ccc(C)cc4C)c3)ccc12]

The titled compound was prepared by repeating the procedure described in example 30.

$^1$H NMR (400 MHz, DMSO-$d_6$) δ 13.72 (br s, 1H), 9.15 (s, 1H), 8.42 (t, J=6 Hz, 1H), 8.22 (d, J=8.4 Hz, 1H), 7.99 (br s, 1H), 7.92 (s, 1H), 7.74 (s, 1H), 7.67 (d, J=8.4 Hz, 1H), 7.51 (d, J=8.8 Hz, 1H), 7.38 (m, 2H), 7.29 (br s, 1H), 6.96 (s, 1H), 6.93 (d, J=8.8 Hz, 1H), 3.33 (br q, J=7.2 Hz, 2H), 2.23 (s, 3H), 2.21 (s, 3H), 1.15 (t, J=7.2 Hz, 3H).

Example 64

Preparation of 6-(5-(3-(4-chloro-3-(trifluoromethyl)phenyl)ureido)-2-methylphenyl)-N-(2-morpholinoethyl)-1H-indazole-3-carboxamide

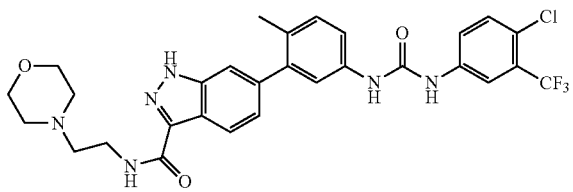 [SMILES: Cc1ccc(NC(=O)Nc2ccc(Cl)c(C(F)(F)F)c2)cc1-c1ccc2c(C(=O)NCCN3CCOCC3)n[nH]c2c1]

The titled compound was prepared by repeating the procedure described in example 30.

$^1$H NMR (400 MHz, DMSO-$d_6$) δ13.57 (s, 1H), 9.16 (s, 1H), 8.85 (s, 1H), 8.27 (br t, J=5.6 Hz, 1H), 8.20 (d, J=8.4 Hz, 1H), 8.10 (d, J=2.8 Hz, 1H), 7.62 (d, J=2 Hz, 1H), 7.60 (s, 1H), 7.49 (s, 1H), 7.45 (d, J=3 Hz, 1H), 7.35 (dd, J=2, 8 Hz, 1H), 7.24 (d, J=8.4 Hz, 1H), 7.21 (dd, J=1.6, 8.4 Hz, 1H), 3.58 (br t, J=4.4 Hz, 4H), 3.45 (m, 2H), 2.46 (m, 6H), 2.18 (s, 3H).

Example 65

Preparation of 6-(5-(3-(4-chloro-3-(trifluoromethyl)phenyl)ureido)-2-methylphenyl)-N-(2-(dimethylamino)ethyl)-1H-indazole-3-carboxamide

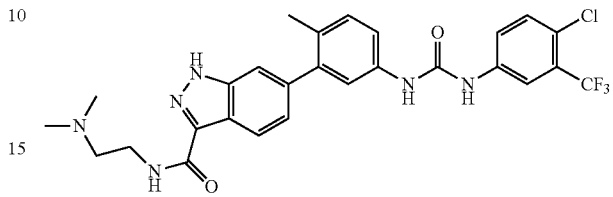

The titled compound was prepared by repeating the procedure described in example 30.

$^1$H NMR (400 MHz, DMSO-$d_6$) δ13.58 (s, 1H), 9.25 (s, 1H), 8.93 (s, 1H), 8.18 (m, 2H), 8.10 (d, J=2 Hz, 1H), 7.62 (m, 2H), 7.49 (s, 1H), 7.45 (d, J=2.5 Hz, 1H), 7.35 (dd, J=2.4, 8.4 Hz, 1H), 7.23 (d, J=9.6 Hz, 1H), 7.21 (dd, J=1.5, 8.4 Hz, 1H), 3.41 (q, J=6.8 Hz, 2H), 2.44 (t, J=6.8 Hz, 2H), 2.20 (s, 6H), 2.18 (s, 3H).

Example 66

Preparation of 6-(5-(3-(4-chloro-3-(trifluoromethyl)phenyl)ureido)-2-methylphenyl)-N-cyclopropyl-1H-indazole-3-carboxamide The titled compound was prepared by repeating the procedure described in example 30.

$^1$H NMR (400 MHz, DMSO-$d_6$) δ 13.57 (s, 1H), 9.18 (s, 1H), 8.86 (s, 1H), 8.44 (d, J=4.4 Hz, 1H), 8.19 (d, J=8.4 Hz, 1H), 8.10 (s, 1H), 7.61 (m, 2H), 7.47 (s, 1H), 7.44 (s, 1H), 7.35 (d, J=8.8 Hz, 1H), 7.23 (d, J=9.6 Hz, 1H), 7.21 (d, J=9.2 Hz, 1H), 3.32 (m, 1H), 2.18 (s, 3H), 1.23 (m, 1H), 0.64 (m, 3H).

Example 67

Preparation of 6-(2-methyl-5-(3-(trifluoromethyl)benzamido)phenyl)-N-(2-morpholinoethyl)-1H-indazole-3-carboxamide

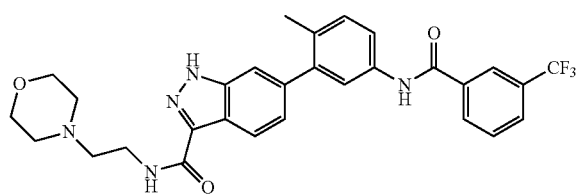 [SMILES: Cc1ccc(NC(=O)c2cccc(C(F)(F)F)c2)cc1-c1ccc2c(C(=O)NCCN3CCOCC3)n[nH]c2c1]

The titled compound was prepared by repeating the procedure described in example 30.

¹H NMR (400 MHz, DMSO-d₆) δ 13.70 (s, 1H), 10.48 (s, 1H), 8.30 (s, 1H), 8.26 (d, J=8 Hz, 1H), 7.96 (d, J=7.6 Hz, 1H), 7.78 (t, J=8 Hz, 1H), 7.73 (s, 2H), 7.52 (s, 1H), 7.33 (d, J=8.4 Hz, 1H), 7.24 (d, J=8.8 Hz, 1H), 3.59 (br s, 4 J), 2.44 (m, 2.23 (s, 3H).

Example 68

Preparation of ethyl 6-(3-(3-(trifluoromethyl)phenylsulfonamido)phenyl)-1H-indazole-3-carboxylate

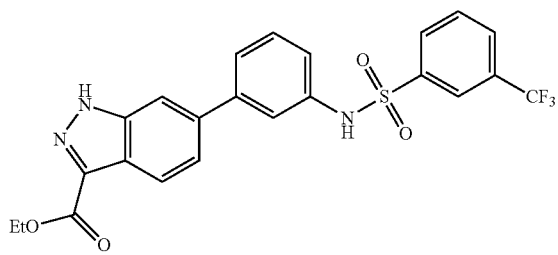 [SMILES: CCOC(=O)c1n[nH]c2cc(-c3cccc(NS(=O)(=O)c4cccc(C(F)(F)F)c4)c3)ccc12]

To a stirred solution of ethyl 6-(3-aminophenyl)-1H-indazole-3-carboxylate (10 mg) in pyridine (1 Ml), was added 3-trifluoromethylbenzenesulfonyl chloride (6.3 µl) at room temperature. After 3 h, pyridine was removed by evaporation. Ethyl acetate and water were added and the aqueous layer was extracted with ethyl acetate three times. The combined organic layer was dried over magnesium sulfate and concentrated under reduced pressure. The residue was triturated in ethyl acetate/hexane to give ethyl 6-(3-(3-(trifluoromethyl)phenylsulfonamido)phenyl)-1H-indazole-3-carboxylate (8.6 mg).

¹H NMR (400 MHz, DMSO-d₆) δ14.11 (s, 1H), 10.64 (s, 1H), 8.08 (m, 4H), 7.83 (t, J=8 Hz, 1H), 7.43 (m, 4H), 7.12 (d, J=8.4 Hz, 1H), 4.40 (q, J=7.2 Hz, 2H), 1.39 (t, J=7.2 Hz, 3H).

Example 69

Preparation of ethyl6-(3-(3-(4-((4-ethylpiperazin-1-yl)methyl)-3-(trifluoromethyl)phenyl)ureido)phenyl)-1H-indazole-3-carboxylate

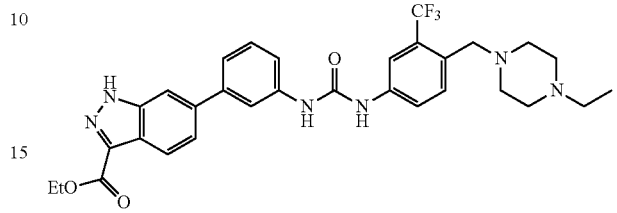

To a stirred solution of 4-((4-ethylpiperazin-1-yl)methyl)-3-(trifluoromethyl)benzeneamine (30.6 mg) in 1,4-dioxane (1 Ml), was added 4-nitrophenylchloroformate (21.6 mg) at room temperature. After 60° C. at 1 h, them mixture was cooled to rt and ethyl 6-(3-aminophenyl)-1H-indazole-3-carboxylate (30 mg) was added. The mixture was stirred at 90° C. for 12 h. Ethyl acetate and water were added and the aqueous layer was extracted with ethyl acetate three times. The combined organic layer was dried over magnesium sulfate and concentrated under reduced pressure. The residue was triturated in ethyl acetate/hexane to give 6-(3-(3-(4-((4-ethylpiperazin-1-yl)methyl)-3-(trifluoromethyl)phenyl)ureido)phenyl)-1H-indazole-3-carboxylate (16.2 mg).

¹H NMR (400 MHz, DMSO-d₆) δ13.98 (s, 1H), 9.09 (s, 1H), 8.93 (s, 1H), 8.15 (8.4 Hz, 1H), 7.99 (s, 1H), 7.93 (s, 1H), 7.81 (s, 1H), 7.62 (m, 3H), 7.43 (br d, J=4.4 Hz, 2H), 7.28 (m, 1H), 4.41 (q, J=7.2 Hz, 2H), 3.54 (s, 2H), 2.49 (m, 10H), 1.39 (t, J=7.2 Hz, 3H).

Example 70

Preparation of methyl 6-(3-(3-(4-(4-methylpiperazin-1-yl)-3-(trifluoromethyl)phenyl)ureido)phenyl)-1H-indazole-3-carboxylate

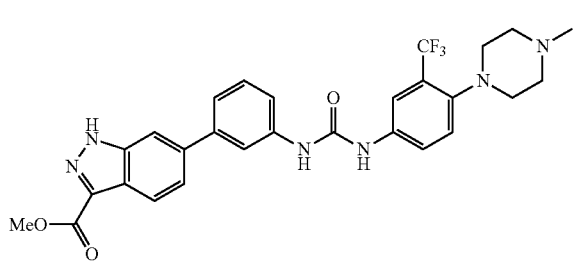 [SMILES: COC(=O)c1n[nH]c2cc(-c3cccc(NC(=O)Nc4ccc(N5CCN(C)CC5)c(C(F)(F)F)c4)c3)ccc12]

The titled compound was prepared by repeating the procedure described in example 69.

¹H NMR (300 MHz, DMSO-d₆) δ14.01 (s, 1H), 9.32 (br s, 1H), 9.21 (br s, 1H), 8.14 (d, J=8.4 Hz, 1H), 7.93 (s, 1H), 7.81 (s, 1H), 7.59 (br d, J=8.4 Hz, 1H), 7.52-7.23 (m, 4H), 6.86 (s, 1H), 3.94 (s, 3H), 3.61 (br s, 4H), 2.81 (br s, 4H), 2.21 (s, 3H).

Example 71

Preparation of ethyl 6-(2-methyl-5-(3-(4-(4-methylpiperazin-1-yl)-3-(trifluoromethyl)phenyl)ureido)phenyl)-1H-indazole-3-carboxylate

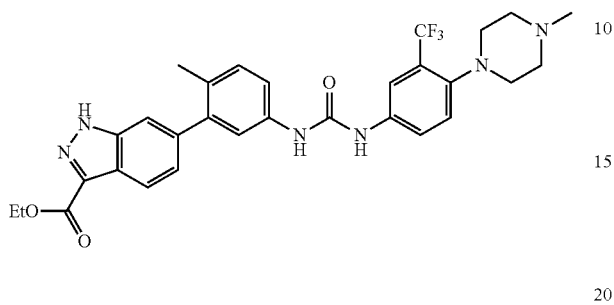

The titled compound was prepared by repeating the procedure described in example 69.

$^1$H NMR (300 MHz, DMSO-d$_6$) δ13.95 (s, 1H), 8.93 (s, 1H), 8.74 (s, 1H), 8.11 (m, 1H), 7.89 (d, J=2.4 Hz, 1H), 7.56 (dd, 1H), 7.48 (d, J=8.8 Hz, 1H), 7.46 (d, J=2.4 Hz, 1H), 7.34 (dd, J=2.4, 8.4 Hz, 1H), 7.30 (dd, J=1.2, 8.4 Hz, 1H), 7.23 (d, J=8.4 Hz, 1H), 6.92 (d, J=9.2 Hz, 1H), 4.41 (q, J=7.2 Hz, 2H), 2.80 (m, 4H), 2.44 (m, 4H), 2.22 (s, 3H), 2.17 (s, 3H), 1.39 (t, J=7.2 Hz, 3H).

Example 72

Preparation of 5-(4-(3-(4-chloro-3-(trifluoromethyl)phenyl)ureido)phenyl)-N-(2-morpholinoethyl)-1H-indazole-3-carboxamide

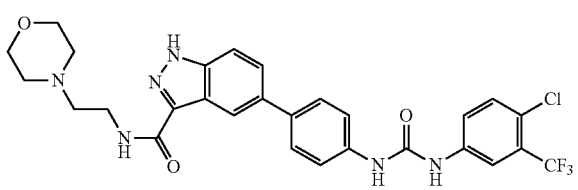 [SMILES: O=C(Nc1ccc(-c2ccc3[nH]nc(C(=O)NCCN4CCOCC4)c3c2)cc1)Nc1ccc(Cl)c(C(F)(F)F)c1]

The titled compound was prepared by repeating the procedure described in example 30.

$^1$H NMR (400 MHz, DMSO-d$_6$) δ13.60 (s, 1H), 9.20 (s, 1H), 8.98 (s, 1H), 8.36 (s, 1H), 8.27 (br t, J=6 Hz, 1H), 8.14 (d, J=2.4 Hz, 1H), 7.72-7.52 (m, 8H), 3.58 (br t, J=4.4 Hz, 4H), 3.44 (m, 2H), 2.44 (m, 6H), 1.98 (s, 3H).

Example 73

Preparation of N-methyl-6-(2-methyl-5-(3-(4-methyl-1H-imidazol-1-yl)-5-(trifluoromethyl)benzamido)phenyl)-1H-indazole-3-carboxamide

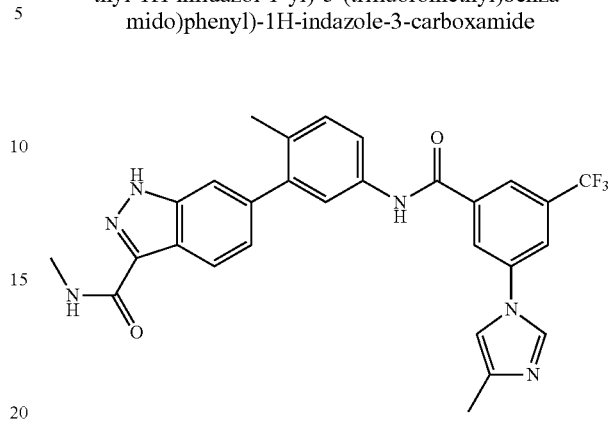

The titled compound was prepared by repeating the procedure described in example 24.

$^1$H NMR (300 MHz, DMSO-d$_6$) δ13.92 (s, 1H), 10.54 (s, 1H), 8.46 (s, 1H), 8.39 (m, 2H), 8.23 (s, 1H), 8.20 (s, 1H), 8.17 (s, 1H), 7.78 (d, J=9.3 Hz, 1H), 7.71 (br s, 2H), 7.51 (s, 1H), 7.35 (d, J=8.4 Hz, 1H), 7.24 (d, J=8.4 Hz, 1H), 2.83 (d, J=4.5 Hz, 3H), 2.24 (s, 3H), 2.18 (s, 3H).

Example 74

Preparation of ethyl 6-(2-methyl-5-(3-(3-(4-methyl-1H-imidazol-1-yl)-5-(trifluoromethyl)phenyl)ureido)phenyl)-1H-indazole-3-carboxylate

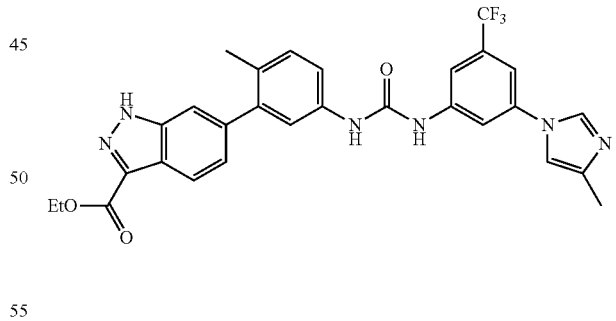

The titled compound was prepared by repeating the procedure described in example 69.

$^1$H NMR (400 MHz, DMSO-d$_6$) δ13.94 (s, 1H), 9.17 (s, 1H), 8.98 (s, 1H), 8.18 (s, 1H), 8.11 (d, J=8.4 Hz, 1H), 7.83 (br s, 2H), 7.55 (s, 2H), 7.49 (d, J=2.4 Hz, 1H), 7.47 (s, 1H), 7.36 (dd, J=2, 8.4 Hz, 1H), 7.30 (d, J=8.4 Hz, 1H), 7.25 (d, J=8 Hz, 1H), 4.42 (q, J=7.2 Hz, 2H), 2.18 (s, 3H), 2.16 (s, 3H), 1.39 (t, J=7.2 Hz, 3H).

Example 75

Preparation of N-methyl-6-(2-methyl-5-(3-(3-(4-methyl-1H-imidazol-1-yl)-5-(trifluoromethyl)phenyl)ureido)phenyl)-1H-indazole-3-carboxamide

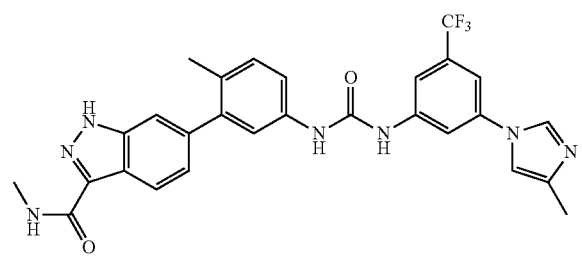 [SMILES: CNC(=O)c1n[nH]c2cc(-c3cc(NC(=O)Nc4cc(-n5cnc(C)c5)cc(C(F)(F)F)c4)ccc3C)ccc12]

The titled compound was prepared by repeating the procedure described in example 24.

¹H NMR (400 MHz, DMSO-d₆) δ13.57 (s, 1H), 9.21 (s, 1H), 9.01 (s, 1H), 8.38 (m, 1H), 8.20 (m, 2H), 7.84 (s, 2H), 7.55 (s, 1H), 7.48 (m, 3H), 7.37 (d, J=8.4 Hz, 1H), 7.23 (m, 2H), 6.86 (s, 1H), 2.82 (d, J=4.8 Hz, 3H), 2.18 (s, 3H), 2.16 (s, 3H).

Example 76

Preparation of ethyl 6-(3-(3-(4-hydroxypiperidin-1-yl)-5-(trifluoromethyl)benzamido)phenyl)-1H-indazole-3-carboxylate

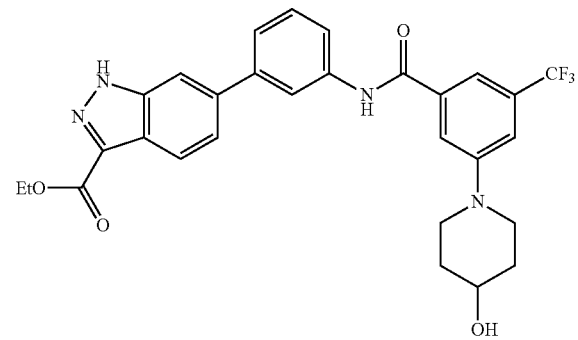 [SMILES: CCOC(=O)c1n[nH]c2cc(-c3cccc(NC(=O)c4cc(N5CCC(O)CC5)cc(C(F)(F)F)c4)c3)ccc12]

The titled compound was prepared by repeating the procedure described in example 2.

¹H NMR (400 MHz, DMSO-d₆) δ10.49 (s, 1H), 8.15 (m, 2H), 7.85 (br s, 2H), 7.74 (s, 1H), 7.63 (m, 2H), 7.51 (m, 2H), 7.36 (s, 1H), 3.68 (m, 1H), 1.98 (m, 4H), 1.41 (m, 4H).

Example 77

Preparation of 6-(3-(3-(4-hydroxypiperidin-1-yl)-5-(trifluoromethyl)benzamido)phenyl)-N-(2-morpholinoethyl)-1H-indazole-3-carboxamide

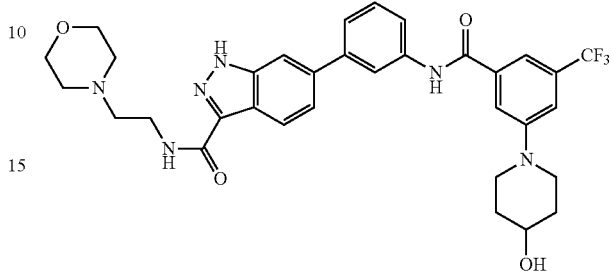

The titled compound was prepared by repeating the procedure described in example 2.

¹H NMR (400 MHz, DMSO-d₆) δ 13.66 (s, 1H), 10.45 (s, 1H), 8.27 (m, 2H), 8.15 (s, 1H), 7.83 (d, J=7.2 Hz, 1H), 7.79 (s, 1H), 7.74 (s, 1H), 7.60-7.49 (m, 4H), 7.36 (s, 1H), 3.71 (m, 4H), 3.67 (m, 1H), 3.45 (m, 2H), 2.44 (m, 6H), 1.83 (m, 4H), 1.47 (m, 4H).

Example 78

Preparation of methyl 6-(3-(4-(1-methylpiperidin-4-yloxy)-3-(trifluoromethyl)benzamido)phenyl)-1H-indazole-3-carboxylate

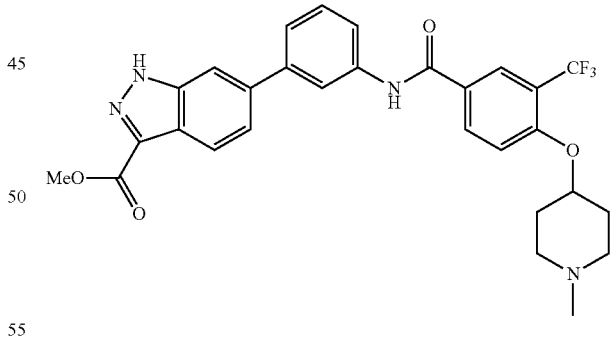

The titled compound was prepared by repeating the procedure described in example 2.

¹H NMR (400 MHz, DMSO-d₆) δ13.99 (s, 1H), 10.43 (s, 1H), 8.28 (m, 2H), 8.16 (br s, 2H), 7.84 (br s, 2H), 7.63 (m, 1H), 7.47 (m, 3H), 4.79 (m, 1H), 3.95 (s, 3H), 2.31 (m, 4H), 2.17 (s, 3H), 1.94 (m, 4H).

Example 79

Preparation of 1-(4-chloro-3-(trifluoromethyl)phenyl)-3-(3-(3-(hydroxymethyl)-1H-indazol-6-yl)phenyl)urea

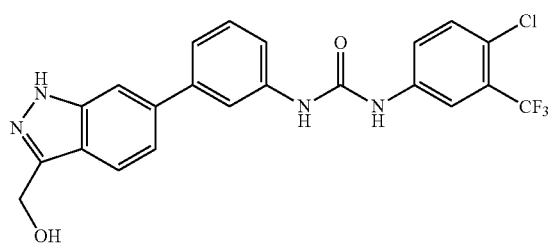 [SMILES: O=C(Nc1cccc(-c2ccc3c(CO)n[nH]c3c2)c1)Nc1ccc(Cl)c(C(F)(F)F)c1]

To a stirred solution of ethyl 6-(3-(3-(4-chloro-3-(trifluoromethyl)phenyl)ureido)phenyl)-1H-indazole-3-carboxylate (73.7 mg) in tetrahydrofuran (5 Ml), was added lithium borohydride (0.44 Ml; LiBH$_4$) at room temperature then, the mixture was stirred at 70° C. for 12 h. Saturated sodium bicarbonate solution and ethyl acetate were added. The aqueous layer was extracted with ethyl acetate and the combined organic layer was dried over magnesium sulfate, and concentrated under reduced pressure. The residue was purified by flash column chromatography to give 1-(4-chloro-3-(trifluoromethyl)phenyl)-3-(3-(3-(hydroxymethyl)-1H-indazol-6-yl)phenyl)urea (32.1 mg).

$^1$H NMR (400 MHz, DMSO-d$_6$) δ12.85 (s, 1H), 9.32 (s, 1H), 9.09 (s, 1H), 8.12 (s, 1H), 7.92 (m, 2H), 7.69-7.61 (m, 3H), 7.41-7.36 (m, 4H), 5.26 (t, J=6 Hz, 1H), 4.79 (d, J=6 Hz, 2H).

Example 80

Preparation of ethyl 6-(5-(3-(trifluoromethyl)phenylcarbamoyl)thiophen-3-yl)-1H-indazole-3-carboxylate

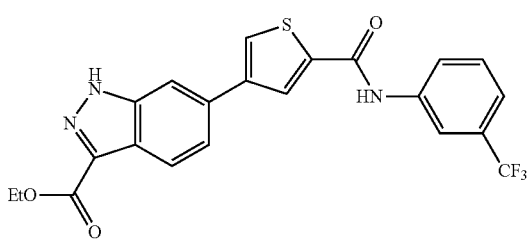 [SMILES: CCOC(=O)c1n[nH]c2cc(-c3csc(C(=O)Nc4cccc(C(F)(F)F)c4)c3)ccc12]

The titled compound was prepared by repeating the procedure described in example 2.

$^1$H NMR (400 MHz, DMSO-d$_6$) δ 10.64 (s, 1H), 8.60 (s, 1H), 8.36 (m, 1H), 8.20 (s, 1H), 8.05 (d, J=8 Hz, 1H), 7.94 (s, 2H), 7.85 (s, 1H), 7.65 (t, J=8 Hz, 1H), 7.49 (d, J=5.6 Hz, 1H), 4.39 (q, J=7.2 Hz, 2H), 1.39 (t, J=7.2 Hz, 3H).

Example 81

Preparation of 6-(4-(2,5-dimethylfuran-3-carboxamido)phenyl)-N-(2-morpholinoethyl)-1H-indaxole-3-carboxamide hydrochloride

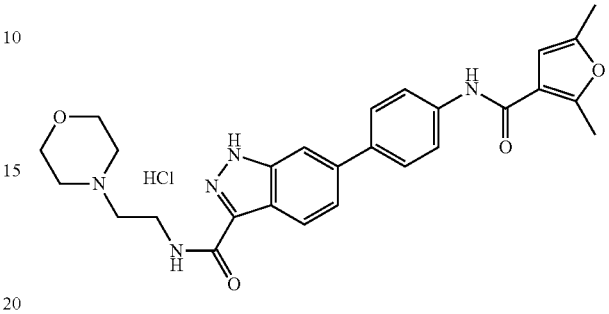

To a stirred solution of 6-(4-(2,5-dimethylfuran-3-carboxamido)phenyl)-N-(2-morpholinoethyl)-1H-indazole-3-carboxamide (38 mg, 78 umol) in tetrahydrofuran (1 Ml), 4N hydrochloric acid solution in dioxane (20 μl) was added at room temperature. After 30 min, the resulting solid was filtered and dried to give 6-(4-(2,5-dimethylfuran-3-carboxamido)phenyl)-N-(2-morpholinoethyl)-1H-indazole-3-carboxamide hydrochloride (35 mg).

$^1$H NMR (300 MHz, DMSO-d$_6$) δ13.79 (s, 1H), 10.26 (br s, 1H), 9.74 (s, 1H), 8.77 (t, J=5.6 Hz, 1H), 8.21 (d, J=8.8 Hz, 1H), 7.87 (d, J=8.8 Hz, 2H), 7.80 (s, 1H), 7.73 (d, J=8.8 Hz, 2H), 7.59 (d, J=8.8 Hz, 1H), 6.71 (s, 1H), 3.98 (br d, J=8.0 Hz, 2H), 3.73 (m, 4H), 3.59 (m, 2H), 3.15 (m, 4H), 2.52 (s, 3H), 2.27 (s, 3H).

Experimental Example 1

B-Raf Kinase Enzyme Assay

<1-1> Activation of MAP Kinase 2/Erk2 by B-raf

10 μl magnesium chloride/ATP solution (500 uM ATP, 75 mM magnesium chloride) was seeded in eppendorf tube. 2.5 μl B-Raf-V600E was seed (final conc. 1 ng) in eppendorf tube and treated with 1.6 μl deactivated MEK1 (final conc. 0.4 μg). The mixture was treated with 4 μl deactivated MAP kinase 2/Erk2 (final conc. 1.0 ug). And the mixture was treated with 1 μl example solution (10 mM) dissolved in dimethyl sulfoxide which was orderly diluted. Then, assay dilution buffer I (ADBI I) was added thereto (final vol. 38 μl) to make the final volume of 38 μl, and made it reacted at 30° C. for 30 min. 5 μl of resulting solution was used for the following experiment.

<1-2> Phosphorylation of Myelin basic protein (MBP)

5 μl of the above resulting solution was treated with 10 μl assay dilution buffer, and then treated with 10 μl Myelin basic protein (MBP, 2 mg/Ml). The mixture solution was treated with 10 μl of diluted (1/10) [γ$^{32}$P] ATP (100 uCi/vial) which is diluted at 30° C. for 10 min. 25 μl of the mixture solution was spotted onto a P81 paper, and the paper was washed four times with 0.75% phosphoric acid for 10 min and once with acetone for 5 min in scintillation vial. After 5 Ml of scintillation cocktail solution was added in the scintillation vial, signals were analyzed by scintillation counter. The said compounds of examples have inhibitory activity of B-Raf-V600E kinase, and the range of IC$_{50}$ is 0.035-20 uM. The kinase activities of representative examples on B-Raf-V600E kinase are shown in the table 1 below.

TABLE 1

| Example | b-raf-V600Ekinase inhibitory activity ($IC_{50}$, uM) |
|---|---|
| Example 8 | <10 |
| Example 17 | <10 |
| Example 21 | <10 |
| Example 24 | <10 |
| Example 48 | <10 |
| Example 50 | <10 |
| Example 54 | <10 |
| Example 57 | <10 |
| Example 58 | <10 |
| Example 64 | <10 |
| Example 79 | <10 |

Also, as mentioned above we tested kinase activities of the representative compounds of the examples using Kinase activity profiling service (Millipore UK Ltd Gemini Crescent, Dundee Technology Park, Dundee DD2 1SW, UK). The results are shown in the table 2 below.

TABLE 2

| Example | Kinase inhibitory activity ($IC_{50}$, uM) | | | | | |
|---|---|---|---|---|---|---|
| | c-RAF (h) | Fms (h) | KDR (h) | Ret (h) | SAPK2a (h) | Tie2 (h) |
| Example 64 | 137 | 141 | 332 | 603 | 167 | 1511 |

Experimental Example 2

Anti-Proliferative Activity on A375P Cell Line (Malignant Melanoma)

A375P cells were purchased from American Type Culture Collection (ATCC, Rockville, Md., US) and maintained in DMEM medium (Welgene, Daegu, Korea) supplemented with 10% FBS (Welgene) and 1% penicillin/streptomycin (Welgene) in a humidified atmosphere with 5% $CO_2$ at 37° C. The A375P cells were taken from culture substrate with 0.05% trypsin-0.02% EDTA and plated at a density of $5\times10^3$ cells/well in 96 well plates and then incubated at 37° C. for 24 h in a humidified atmosphere with 5% $CO_2$ prior to treatment of various concentration (three fold serial dilution, 12 points) of test compounds. The A357P cell viability was assessed by the conventional 3-(4,5-dimethylthiazol-2-yl)-2,5-diphenyltetrazolium bromide (MTT) reduction assay. MTT assays were carried out with CellTiter 96 (Promega) according to the manufacturer's instructions.

After 1 day, 0.5 μl the representative compounds of the examples were added thereto. The representative compounds of the examples were prepared by three fold serial dilution of 10 mM stock solution in DMSO, 12 point (final conc. DMSO 0.5%). Then, 15 μl dye was added in each well. After 2 h, 100 μl stop solution was added each well. After 24 h, absorbance was measured. The absorbance at 590 nm was recorded using EnVision2103 (PerkinElmer; Boston, Mass., US). The $IC_{50}$ value was calculated using GraphPad Prism 4.0 software.

The compounds in this invention showed a $GI_{50}$ value in the range of 1 nM to 10 uM on A375P, human melanoma cell line in which b-raf-V600E mutant species are over-expressed.

The anti-proliferative activities of representative examples on A375P is shown in the table 3 below.

TABLE 3

| Example | A375P anti-proliferative activity ($GI_{50}$, uM) |
|---|---|
| Example 2 | <10 |
| Example 8 | <10 |
| Example 10 | <10 |
| Example 11 | <10 |
| Example 13 | <10 |
| Example 15 | <10 |
| Example 16 | <10 |
| Example 19 | <10 |
| Example 20 | <10 |
| Example 21 | <10 |
| Example 22 | <10 |
| Example 23 | <10 |
| Example 24 | <10 |
| Example 25 | <10 |
| Example 26 | <10 |
| Example 27 | <10 |
| Example 30 | <10 |
| Example 31 | <10 |
| Example 32 | <10 |
| Example 33 | <10 |
| Example 34 | <10 |
| Example 35 | <10 |
| Example 36 | <10 |
| Example 39 | <10 |
| Example 40 | <10 |
| Example 43 | <10 |
| Example 46 | <10 |
| Example 47 | <10 |
| Example 48 | <10 |
| Example 49 | <10 |
| Example 52 | <10 |
| Example 54 | <10 |
| Example 55 | <10 |
| Example 56 | <10 |
| Example 57 | <10 |
| Example 58 | <10 |
| Example 59 | <10 |
| Example 60 | <10 |
| Example 61 | <10 |
| Example 62 | <10 |
| Example 63 | <10 |
| Example 64 | <10 |
| Example 65 | <10 |
| Example 66 | <10 |
| Example 67 | <10 |
| Example 68 | <10 |
| Example 69 | <10 |
| Example 70 | <10 |
| Example 71 | <10 |
| Example 72 | <10 |
| Example 73 | <10 |
| Example 75 | <10 |
| Example 76 | <10 |
| Example 77 | <10 |
| Example 78 | <10 |
| Example 79 | <10 |

Experimental Example 3

Western Blotting

Western blotting was performed with the compound of the example 64 of the present invention. A375P cell line was lysed by using RIPA buffer solution (50 mM tris pH 7.4, 150 mM NaCl, 1 mM EDTA, 1% NP-40, 0.25% sodium deoxycholate) containing phosphatase inhibitor (Phosphatase inhibitor cocktail I & II) and protease inhibitor (Complete, Mini, EDTA-free; Roche Applied Science), and centrifuged at 13000 rpm for 10 min. Whole protein was stained with Bio-Rad agent (bio-rad #500-0006) and quantitated by comparing with BSA (positive control). 12% gel was prepared by using 30% acrylamide, 1.5 M Tris (pH 8.8), 10% SDS solution, 10% PAS solution and TEMED. After loading 100 ug of protein per one lane of gel, proteins were isolated by sodium-dodecylsulfate polyacrylamide gel electrophoresis (SDS-PAGE, 250 mM Tris base, 2.5 M Glycine, 0.1% SDS, 140V, electrophoresis for 2 h), and transferred to nitrocellulose filter at 200 mA for 2 h. The results are weakly reacted with an antibody[Rabbit anti-Map Kinase (Zymed #61-7400) and phosphor-p44/42 MAP kinase (Thr202/Tyr204) (Cell signaling #9101)] at 4° C. for a day. Further, it is washed with TBST buffer solution containing 0.05% tween20 at 4 times every 5 minutes. The results are weakly reacted with secondary antibody[anti-rabbit IgG (Amersham #NA934V)] for one hour at room temperature, and washed by the same manner. Protein bands were identified with imaging apparatus (Gelliance). The results is shown in FIG. 1.

The invention claimed is:

1. An indazole derivative represented by the following Chemical Formula 1 or a pharmaceutically acceptable salt thereof:

[Chemical Formula 1]

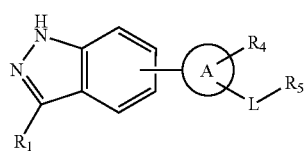

wherein, $R_1$ is $HOCH_2$— or

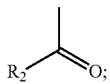

$R_2$ is hydrogen, hydroxy, $C_1$-$C_3$ alkoxy or $R_3$—$(CH_2)_n$—NH—;

$R_3$ is hydrogen, dimethylamine, morpholine, phenyl, phenyl which is substituted with $CF_3$, or $C_3$-$C_6$ cycloalkyl;

A is 5-6 membered aryl or heteroaryl which is substituted with $R_4$ and $LR_5$;

$R_4$ is hydrogen or $C_1$-$C_3$ alkyl;

L is —NH— or —C(O)NH—;

$R_5$ is hydrogen, —C(O)—$R_6$, —C(O)NH—$R_6$ or —SO$_2$—$R_6$;

$R_6$ is one selected from a group consisting of phenyl, benzyl, 5 or 6 membered heteroaryl, naphthalenyl and benzothienyl, wherein each one is substituted with one or two substituents selected from a group consisting of hydrogen, —$CH_3$, —$CF_3$, —$OCH_3$, —Br, —Cl, —$NO_2$,

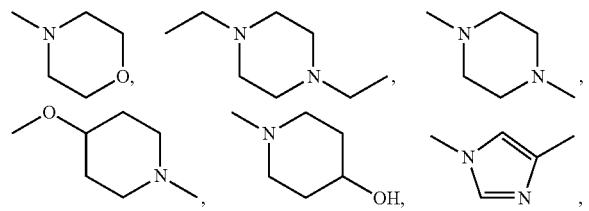

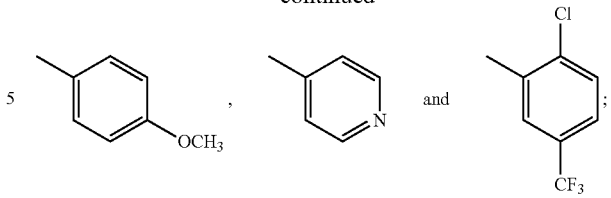

and n is 0, 1 or 2.

2. The indazole derivative according to claim 1, wherein the $R_2$ is hydrogen, hydroxy, methoxy, ethoxy or $R_3$—$(CH_2)_n$—NH—.

3. The indazole derivative according to claim 1, wherein the $R_3$ is hydrogen, dimethylamine, morpholine, phenyl, phenyl which is substituted with $CF_3$, or cyclopropyl.

4. The indazole derivative according to claim 1, wherein the A is phenyl or thienyl which is substituted with $R_4$ and —$NHR_5$.

5. The indazole derivative according to claim 1, wherein the $R_4$ is hydrogen or methyl.

6. The indazole derivative according to claim 1, wherein the 5 or 6 membered heteroaryl of $R_6$ is thienyl, furanyl, oxazolyl, isoxazolyl, thiazolyl, pyrazolyl, isothiazolyl, pyridyl, pyridazinyl or pyrazinyl.

7. The indazole derivative according to claim 1, wherein the $R_6$ is phenyl, (trifluoromethyl)phenyl, 4-nitro-3-(trifluoromethyl)phenyl, 3-(4-methyl-1H-imidazole-1-yl)-5-(trifluoromethyl)phenyl, 4-(1-methylpiperidine-4-yloxy)-3-(trifluoromethyl)phenyl, 3,4-dichlorophenyl, 4-chloro-3-(trifluoromethyl)phenyl, 3,5-bis(trifluoromethyl)phenyl, 3,4-dimethoxyphenyl, 3-morpholino-5-(trifluoromethyl)phenyl, 2,3-dichlorophenyl, 2,4-dimethylphenyl, 4-((4-ethylpiperazin-1-yl)methyl)-3-(trifluoromethyl)phenyl, 4-(4-methylpiperazin-1-yl)-3-(trifluoromethyl)phenyl, 3-(4-hydroxypiperadin-1-yl)-5-(trifluoromethyl)phenyl, 4-(1-methylpiperadin-4-yloxy)-3-(trifluoromethyl)phenyl, benzyl, 3,4-dimethoxybenzyl, thienyl, 5-bromothienyl, pyrazinyl, furanyl, 2,5-dimethylfuranyl, 5-(4-methoxypenyl)furanyl, 5-(2-chloro-5-(trifluoromethyl)phenyl)furanyl, isoxazolyl, 5-methyl isoxazolyl, pyrazolyl, 1-(4-methoxyphenyl)-5-(trifluoromethyl)-1H-pyrazolyl, pyridazinyl, pyridinyl, 3-chloropyridinyl, thiazolyl, 4-(2-(pyridin-4-yl)thiazolyl, naphthalenyl, 4,7-dimethoxynaphthalenyl, benzo[b]thiophenyl, pyrimidinyl, imidazolyl, pyrrolyl, dihydropyrrolyl, oxazolyl, triazolyl, thiadiazolyl, benzimidazolyl, quinolinyl, tetrahydroquinolinyl, benzothiazolyl, benzothiazophenyl, benzodioxolyl, indazolyl, indolyl, indylyl, dihydroindylyl or dihyrobenzofuranyl.

8. The indazole derivative according to claim 1, being selected from a group consisting of:

1) ethyl 6-(4-aminophenyl)-1H-indazole-3-carboxylate;
2) ethyl 6-(4-(3-(trifluoromethyl)benzamido)phenyl)-1H-indazole-3-carboxylate;
3) ethyl 6-(4-(5-bromothiophene-2-carboxamido)phenyl)-1H-indazole-3-carboxylate;
4) ethyl 6-(4-(pyrazine-2-carboxamido)phenyl)-1H-indazole-3-carboxylate;
5) ethyl 6-(4-(benzo[b]thiophene-2-carboxamido)phenyl)-1H-indazole-3-carboxylate;
6) ethyl 6-(4-(2,5-dimethylfuran-3-carboxamido)phenyl)-1H-indazole-3-carboxylate;
7) ethyl 6-(4-(5-methylisoxazole-3-carboxamido)phenyl)-1H-indazole-3-carboxylate;

8) ethyl 6-(4-(1-(4-methoxyphenyl)-5-(trifluoromethyl)-1H-pyrazole-4-carboxamido)phenyl)-1H-indazole-3-carboxylate;
9) ethyl 6-(4-(4-nitro-3-(trifluoromethyl)benzamido)phenyl)-1H-indazole-3-carboxylate;
10) ethyl 6-(4-(pyridazine-4-carboxamido)phenyl)-1H-indazole-3-carboxylate;
11) ethyl 6-(4-(2-(3,4-dimethoxyphenyl)acetamido)phenyl)-1H-indazole-3-carboxylate;
12) ethyl 6-(4-(5-(4-methoxyphenyl)furan-2-carboxamido)phenyl)-1H-indazole-3-carboxylate;
13) ethyl 6-(4-(3-chloroisonicotinamido)phenyl)-1H-indazole-3-carboxylate;
14) ethyl 6-(4-(thiazole-4-carboxamido)phenyl)-1H-indazole-3-carboxylate;
15) ethyl 6-(4-(4,7-dimethoxy-1-naphthamido)phenyl)-1H-indazole-3-carboxylate;
16) ethyl 6-(4-(5-(2-chloro-5-(trifluoromethyl)phenyl)furan-2-carboxamido)phenyl)-1H-indazole-3-carboxylate;
17) ethyl 6-(4-(2-(pyridin-4-yl)thiazole-4-carboxamido)phenyl)-1H-indazole-3-carboxylate;
18) ethyl 6-(4-(3-(4-methyl-1H-imidazol-1-yl)-5-(trifluoromethyl)benzamido)phenyl)-1H-indazole-3-carboxylate;
19) ethyl 6-(4-(4-(1-methylpiperidin-4-yloxy)-3-(trifluoromethyl)benzamido)phenyl)-1H-indazole-3-carboxylate;
20) ethyl 6-(4-(3-(3,4-dichlorophenyl)ureido)phenyl)-1H-indazole-3-carboxylate;
21) ethyl 6-(4-(3-(4-chloro-3-(trifluoromethyl)phenyl)ureido)phenyl)-1H-indazole-3-carboxylate;
22) ethyl 6-(4-(3-(3,5-bis(trifluoromethyl)phenyl)ureido)phenyl)-1H-indazole-3-carboxylate;
23) ethyl 6-(4-(3-(3-(trifluoromethyl)phenyl)ureido)phenyl)-1H-indazole-3-carboxylate;
24) N-methyl-6-(4-(3-(trifluoromethyl)benzamido)phenyl)-1H-indazole-3-carboxamide;
25) 6-(4-(5-(4-methoxyphenyl)furan-2-carboxamido)phenyl)-N-methyl-1H-indazole-3-carboxamide;
26) 6-(4-(5-bromothiophene-2-carboxamido)phenyl)-N-methyl-1H-indazole-3-carboxamide;
27) 6-(4-(benzo[b]thiophene-2-carboxamido)phenyl)-N-methyl-1H-indazole-3-carboxamide;
28) 6-(4-(3-(3,5-bis(trifluoromethyl)phenyl)ureido)phenyl)-N-methyl-1H-indazole-3-carboxamide;
29) N-methyl-6-(4-(3-(3-(trifluoromethyl)phenyl)ureido)phenyl)-1H-indazole-3-carboxamide;
30) N-(2-morpholinoethyl)-6-(4-(3-(trifluoromethyl)benzamido)phenyl)-1H-indazole-3-carboxamide;
31) 6-(4-(5-bromothiophene-2-carboxamido)phenyl)-N-(2-morpholinoethyl)-1H-indazole-3-carboxamide;
32) 6-(4-(benzo[b]thiophene-2-carboxamido)phenyl)-N-(2-morpholinoethyl)-1H-indazole-3-carboxamide;
33) 6-(4-(2,5-dimethylfuran-3-carboxamido)phenyl)-N-(2-morpholinoethyl)-1H-indazole-3-carboxamide;
34) 6-(4-(1-(4-methoxyphenyl)-5-(trifluoromethyl)-1H-pyrazole-4-carboxamido)phenyl)-N-(2-morpholinoethyl)-1H-indazole-3-carboxamide;
35) 6-(4-(5-bromothiophene-2-carboxamido)phenyl)-N-(3-(trifluoromethyl)phenyl)-1H-indazole-3-carboxamide;
36) 6-(4-(3-(3,4-dichlorophenyl)ureido)phenyl)-N-(2-morpholinoethyl)-1H-indazole-3-carboxamide;
37) N-methyl-6-(4-(pyridazine-4-carboxamido)phenyl)-1H-indazole-3-carboxamide;
38) 5-methyl-N-(4-(3-(methylcarbamoyl)-1H-indazol-6-yl)phenyl)isoxazole-3-carboxamide;
39) N-methyl-6-(4-(3-(4-methyl-1H-imidazol-1-yl)-5-(trifluoromethyl)benzamido)phenyl)-1H-indazole-3-carboxamide;
40) N-methyl-6-(4-(4-(1-methylpiperidin-4-yloxy)-3-(trifluoromethyl)benzamido)phenyl)-1H-indazole-3-carboxamide;
41) N-(4-(3-(methylcarbamoyl)-1H-indazol-6-yl)phenyl)thiazole-4-carboxamide;
42) methyl 5-(4-aminophenyl)-1H-indazole-3-carboxylate;
43) methyl 5-(4-(3-(4-chloro-3-(trifluoromethyl)phenyl)ureido)phenyl)-1H-indazole-3-carboxylate;
44) ethyl 6-(3-aminophenyl)-1H-indazole-3-carboxylate;
45) ethyl 6-(3-(3-(trifluoromethyl)benzamido)phenyl)-1H-indazole-3-carboxylate;
46) ethyl 6-(3-(5-methylisoxazole-3-carboxamido)phenyl)-1H-indazole-3-carboxylate;
47) ethyl 6-(3-(benzo[b]thiophene-2-carboxamido)phenyl)-1H-indazole-3-carboxylate;
48) ethyl 6-(3-(2-(3,4-dimethoxyphenyl)acetamido)phenyl)-1H-indazole-3-carboxylate;
49) ethyl 6-(3-(5-bromothiophene-2-carboxamido)phenyl)-1H-indazole-3-carboxylate;
50) N-(2-morpholinoethyl)-6-(3-(3-(trifluoromethyl)benzamido)phenyl)-1H-indazole-3-carboxamide;
51) methyl 6-(3-aminophenyl)-1H-indazole-3-carboxylate;
52) methyl 6-(3-(3-morpholino-5-(trifluoromethyl)benzamido)phenyl)-1H-indazole-3-carboxylate;
53) ethyl 6-(5-amino-2-methylphenyl)-1H-indazole-3-carboxylate;
54) ethyl 6-(3-(3-(2,3-dichlorophenyl)ureido)phenyl)-1H-indazole-3-carboxylate;
55) ethyl 6-(3-(3-(3,4-dichlorophenyl)ureido)phenyl)-1H-indazole-3-carboxylate;
56) methyl 6-(3-(3-(2,4-dimethylphenyl)ureido)phenyl)-1H-indazole-3-carboxylate;
57) ethyl 6-(5-(3-(4-chloro-3-(trifluoromethyl)phenyl)ureido)-2-methylphenyl)-1H-indazole-3-carboxylate;
58) 6-(3-(3-(4-chloro-3-(trifluoromethyl)phenyl)ureido)phenyl)-N-(2-morpholinoethyl)-1H-indazole-3-carboxamide;
59) 6-(3-(3-morpholino-5-(trifluoromethyl)benzamido)phenyl)-N-(2-morpholinoethyl)-1H-indazole-3-carboxamide;
60) 6-(3-(3-(2,3-dichlorophenyl)ureido)phenyl)-N-(2-morpholinoethyl)-1H-indazole-3-carboxamide;
61) 6-(3-(3-(2,3-dichlorophenyl)ureido)phenyl)-N-ethyl-1H-indazole-3-carboxamide;
62) 6-(3-(3-(3,4-dichlorophenyl)ureido)phenyl)-N-ethyl-1H-indazole-3-carboxamide;
63) 6-(3-(3-(2,4-dimethylphenyl)ureido)phenyl)-N-ethyl-1H-indazole-3-carboxamide;
64) 6-(5-(3-(4-chloro-3-(trifluoromethyl)phenyl)ureido)-2-methylphenyl)-N-(2-morpholinoethyl)-1H-indazole-3-carboxamide;
65) 6-(5-(3-(4-chloro-3-(trifluoromethyl)phenyl)ureido)-2-methylphenyl)-N-(2-(dimethylamino)ethyl)-1H-indazole-3-carboxamide;
66) 6-(5-(3-(4-chloro-3-(trifluoromethyl)phenyl)ureido)-2-methylphenyl)-N-cyclopropyl-1H-indazole-3-carboxamide;
67) 6-(2-methyl-5-(3-(trifluoromethyl)benzamido)phenyl)-N-(2-morpholinoethyl)-1H-indazole-3-carboxamide;

68) ethyl 6-(3-(3-(trifluoromethyl)phenylsulfonamido)phenyl)-1H-indazole-3-carboxylate;
69) ethyl 6-(3-(3-(4-((4-ethylpiperazin-1-yl)methyl)-3-(trifluoromethyl)phenyl)ureido)phenyl)-1H-indazole-3-carboxylate;
70) methyl 6-(3-(3-(4-(4-methylpiperazin-1-yl)-3-(trifluoromethyl)phenyl)ureido)phenyl)-1H-indazole-3-carboxylate;
71) ethyl 6-(2-methyl-5-(3-(4-(4-methylpiperazin-1-yl)-3-(trifluoromethyl)phenyl)ureido)phenyl)-1H-indazole-3-carboxylate;
72) 5-(4-(3-(4-chloro-3-(trifluoromethyl)phenyl)ureido)phenyl)-N-(2-morpholinoethyl)-1H-indazole-3-carboxamide;
73) N-methyl-6-(2-methyl-5-(3-(4-methyl-1H-imidazol-1-yl)-5-(trifluoromethyl)benzamido)phenyl)-1H-indazole-3-carboxamide;
74) ethyl 6-(2-methyl-5-(3-(3-(4-methyl-1H-imidazol-1-yl)-5-(trifluoromethyl)phenyl)ureido)phenyl)-1H-indazole-3-carboxylate;
75) N-methyl-6-(2-methyl-5-(3-(3-(4-methyl-1H-imidazol-1-yl)-5-(trifluoromethyl)phenyl)ureido)phenyl)-1H-indazole-3-carboxamide;
76) ethyl 6-(3-(3-(4-hydroxypiperidin-1-yl)-5-(trifluoromethyl)benzamido)phenyl)-1H-indazole-3-carboxylate;
77) 6-(3-(3-(4-hydroxypiperidin-1-yl)-5-(trifluoromethyl)benzamido)phenyl)-N-(2-morpholinoethyl)-1H-indazole-3-carboxamide;
78) methyl 6-(3-(4-(1-methylpiperidin-4-yloxy)-3-(trifluoromethyl)benzamido)phenyl)-1H-indazole-3-carboxylate;
79) 1-(4-chloro-3-(trifluoromethyl)phenyl)-3-(3-(3-(hydroxymethyl)-1H-indazol-6-yl)phenyl)urea;
80) ethyl-6-(5-(3-(trifluoromethyl)phenylcarbamoyl)thiophen-3-yl)-1H-indazole-3-carboxylate; or
81) 6-(4-(2,5-dimethylfuran-3-carboxamido)phenyl)-N-(2-morpholinoethyl)-1H-indazole-3-carboxamide hydrochloride.

\* \* \* \* \*